(12) United States Patent
Gerke et al.

(10) Patent No.: US 7,098,178 B2
(45) Date of Patent: Aug. 29, 2006

(54) SILICIC ACID ESTER MIXTURES

(75) Inventors: Thomas Gerke, Neuss (GB);
Ulf-Armin Schaper, Krefeld (GB);
Werner Faber, Willich (GB)

(73) Assignee: Henkel Kommanditgesellschaft Auf Aktien (Henkel KGAA), Duesseldorf (DE)

( * ) Notice: Subject to any disclaimer, the term of this patent is extended or adjusted under 35 U.S.C. 154(b) by 0 days.

(21) Appl. No.: 10/221,890

(22) PCT Filed: Mar. 8, 2001

(86) PCT No.: PCT/EP01/02593

§ 371 (c)(1),
(2), (4) Date: Sep. 17, 2002

(87) PCT Pub. No.: WO01/68037

PCT Pub. Date: Sep. 20, 2001

(65) Prior Publication Data
US 2004/0072704 A1     Apr. 15, 2004

(30) Foreign Application Priority Data
Mar. 16, 2000  (DE) ............... 100 12 949

(51) Int. Cl.
*A61K 7/00* (2006.01)
(52) U.S. Cl. .................... 510/466; 512/25
(58) Field of Classification Search ........... 510/101, 510/466; 512/25
See application file for complete search history.

(56) References Cited

U.S. PATENT DOCUMENTS

| 2,547,944 | A | 4/1951 | Iler ............... 556/457 |
| 3,158,615 | A | 11/1964 | Dunn et al. |
| 3,215,719 | A | 11/1965 | Allen et al. |
| 3,234,258 | A | 2/1966 | Morris |
| 3,779,932 | A | 12/1973 | Jaggers et al. |
| 3,849,326 | A | 11/1974 | Jaggers et al. |
| 4,062,647 | A | 12/1977 | Storm et al. |
| 4,130,530 | A | 12/1978 | Mark et al. ............ 524/261 |
| 4,209,644 | A | 6/1980 | Ichikawa et al. |
| 4,237,253 | A | 12/1980 | Jacquet et al. |
| 4,524,009 | A | 6/1985 | Valenty |
| 4,524,018 | A | 6/1985 | Yemoto et al. |
| 4,639,325 | A | 1/1987 | Valenty et al. |
| 4,737,306 | A | 4/1988 | Wichelhaus et al. |
| 4,814,101 | A | 3/1989 | Schieferstein et al. |
| 4,816,553 | A | 3/1989 | Baur et al. |
| 4,820,439 | A | 4/1989 | Rieck |
| 4,925,587 | A | 5/1990 | Schenker et al. |
| 4,985,553 | A | 1/1991 | Fuertes et al. |
| 4,994,266 | A | 2/1991 | Wells |
| 5,075,041 | A | 12/1991 | Lutz |
| 5,081,111 | A | 1/1992 | Akimoto et al. |
| 5,266,592 | A | 11/1993 | Grub et al. |
| 5,378,468 | A | 1/1995 | Suffis et al. |
| 5,382,377 | A | 1/1995 | Raehse et al. |
| 5,431,780 | A | 7/1995 | Raehse et al. |
| 5,494,488 | A | 2/1996 | Arnoldi et al. |
| 5,501,814 | A | 3/1996 | Engelskirchen et al. |
| 5,519,948 | A | 5/1996 | Raehse et al. |
| 5,536,430 | A | 7/1996 | Fues et al. |
| 5,537,759 | A | 7/1996 | Raehse et al. |
| 5,541,316 | A | 7/1996 | Engelskirchen et al. |
| 5,544,427 | A | 8/1996 | Raehse et al. |
| 5,580,941 | A | 12/1996 | Krause et al. |
| 5,637,560 | A | 6/1997 | Raehse et al. |
| 5,780,420 | A | 7/1998 | Breuer et al. |
| 5,821,360 | A | 10/1998 | Engelskirchen et al. |
| 5,830,956 | A | 11/1998 | Stockhausen et al. |

(Continued)

FOREIGN PATENT DOCUMENTS

CA     2 053 900 A1    10/1990

(Continued)

OTHER PUBLICATIONS

Steinmann, et al., "Umalkoxylierung in der siliciumorganischen Chemie," Z. Chem. 3, pp. 89-92, (1977).

(Continued)

*Primary Examiner*—John R. Hardee
(74) *Attorney, Agent, or Firm*—Woodcock Washburn LLP

(57) ABSTRACT

The invention relates to silicic acid ester mixtures containing silicic acid esters of formulae (I) and (II), all 'R's being selected, independently of each other, from the following group: H, the straight-chained or branched, saturated or unsaturated, substituted or unsubstituted C1–6-hydrocarbon radicals and fragrance alcohol radicals and biocide alcohol radicals, m taking on values of 1 to 20 and n taking on values from 2 to 100. These esters of oligosilicic acid with fragrance alcohols or biocide alcohols are characterised by a good hydrolysis stability and can also be used in aqueous media or in processes for producing granulates without undergoing excessive losses of activity

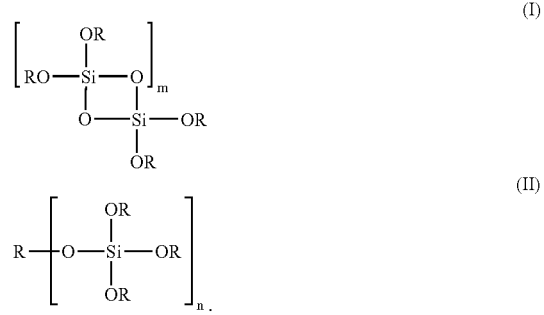

44 Claims, No Drawings

U.S. PATENT DOCUMENTS

| | | | |
|---|---|---|---|
| 5,959,101 A | 9/1999 | Engelskirchen et al. | |
| 5,981,465 A * | 11/1999 | Ramachandran et al. | ... 510/466 |
| 6,187,055 B1 | 2/2001 | Kottwitz et al. | |
| 6,336,977 B1 | 1/2002 | Menke et al. | |

FOREIGN PATENT DOCUMENTS

| | | |
|---|---|---|
| CA | 2 066 226 | 3/1991 |
| CA | 2 147 744 | 4/1994 |
| CA | 2 324 075 | 9/1999 |
| DE | 21 50 557 | 6/1972 |
| DE | 23 34 899 | 1/1974 |
| DE | 28 17 369 A1 | 10/1978 |
| DE | 28 44 789 A1 | 4/1979 |
| DE | 30 03 494 A1 | 8/1980 |
| DE | 35 26 405 A1 | 2/1987 |
| DE | 37 08 451 A1 | 10/1988 |
| DE | 38 16 842 A1 | 11/1989 |
| DE | 39 29 973 A1 | 3/1991 |
| DE | 40 30 688 A1 | 4/1992 |
| DE | 42 04 035 A1 | 8/1993 |
| DE | 42 04 090 A1 | 8/1993 |
| DE | 42 06 050 A1 | 9/1993 |
| DE | 42 06 051 A1 | 9/1993 |
| DE | 42 06 495 A1 | 9/1993 |
| DE | 42 08 773 A1 | 9/1993 |
| DE | 42 09 432 A1 | 9/1993 |
| DE | 42 21 381 C1 | 2/1994 |
| DE | 42 34 376 A1 | 4/1994 |
| DE | 44 00 024 A1 | 7/1995 |
| DE | 44 17 734 A1 | 11/1995 |
| DE | 43 03 320 C2 | 12/1995 |
| DE | 195 20 145 A1 | 12/1996 |
| DE | 43 00 772 C2 | 3/1997 |
| DE | 195 40 086 A1 | 4/1997 |
| DE | 196 00 018 A1 | 7/1997 |
| DE | 37 23 323 C2 | 3/1998 |
| DE | 197 50 706 A1 | 5/1998 |
| DE | 197 10 254 A1 | 9/1998 |
| DE | 197 15 872 C2 | 4/1999 |
| DE | 198 11 386 A1 | 9/1999 |
| DE | 197 09 991 C1 | 12/1999 |
| DE | 198 41 147 A1 | 3/2000 |
| DE | 198 56 529 A1 | 6/2000 |
| DE | 199 48 667 A1 | 4/2001 |
| EP | 0 026 529 A1 | 4/1981 |
| EP | 0 150 930 A2 | 8/1985 |
| EP | 0 164 514 A1 | 12/1985 |
| EP | 0 232 202 A2 | 8/1987 |
| EP | 0 280 223 A2 | 8/1988 |
| EP | 0 427 349 A2 | 5/1991 |
| EP | 0 472 042 A1 | 2/1992 |
| EP | 0 522 506 A2 | 1/1993 |
| EP | 0 542 496 A1 | 5/1993 |
| EP | 0 486 592 B1 | 6/1994 |
| EP | 0 738 700 A1 | 10/1996 |
| EP | 0 727 448 B1 | 6/1998 |
| EP | 0 703 292 B1 | 4/2001 |
| EP | 0 977 548 B1 | 8/2004 |
| GB | 1 368 495 | 9/1974 |
| GB | 2007703 * | 5/1979 |
| GB | 2 041 964 A | 9/1980 |
| GB | 2 319 572 A | 5/1998 |
| GB | 2319527 * | 5/1998 |
| JP | 58/217598 A | 12/1983 |
| JP | 93/339896 A | 12/1993 |
| WO | WO 90/13533 A1 | 11/1990 |
| WO | WO 92/18542 A1 | 10/1992 |
| WO | WO 93/02176 A1 | 2/1993 |
| WO | WO 93/08251 A1 | 4/1993 |
| WO | WO93/16110 A1 | 8/1993 |
| WO | WO 94/09111 A1 | 4/1994 |
| WO | WO 94/22800 A1 | 10/1994 |
| WO | WO 94/28030 A1 | 12/1994 |
| WO | WO 95/04809 | 2/1995 |
| WO | WO 95/07303 A1 | 3/1995 |
| WO | WO 95/07331 A1 | 3/1995 |
| WO | WO 96/12001 A1 | 4/1995 |
| WO | WO 95/12619 A1 | 5/1995 |
| WO | WO 95/16660 | 6/1995 |
| WO | WO 95/20029 A1 | 7/1995 |
| WO | WO 95/20608 A1 | 8/1995 |
| WO | WO 96/04358 A1 | 2/1996 |
| WO | WO 96/14827 | 5/1996 |
| WO | WO 96/38528 | 12/1996 |
| WO | WO 97/34578 | 9/1997 |
| WO | WO 98/07405 | 2/1998 |
| WO | WO 98/12299 A1 | 3/1998 |
| WO | WO 98/40463 A1 | 9/1998 |
| WO | WO 00/14091 A1 | 3/2000 |

OTHER PUBLICATIONS

Falbe, et al., "Römpp Chemie Lexikon," 9th Edition, vol. 6, p. 4440, Verlag Stuttgart New York, (1992).

Voigt, "Lehrbuch der pharmazeutischen Technologie," 6th Edition, pp. 182-184 (1987).

Lewis, S.Z., et al., "Akloxysilane chemistry and stone conservation," *Actes—Congr. Int. Alternation Conserv. Pierre,* 5th, 1985, 2, 831-844, Accession No. 1986:460054.

Marsmann, H. C. et al., "Cyclische Kieselsäurederivate," *Z. Anorg. Allg. Chem.*, 1987, 548, 193-203.

Ozerenko, E.A., et al., "Structure of products of the aqueous ethanolysis of silicon tetrachloride," *Translated from Zhurnal Obshchei Khimii,* 1990, 60(2), 394-399.

Söger, N., et al., "Hydrolysis and condensation of $Si(OEt)_4$: separation and characterization of intermediates by mass spectrometry," *Z. Anorg. Allg. Chem.*, 2003, 629, 232-238 (English Abstract).

Von Duftstoffen, K.F., "Kontrollierte Freisetzung von Duftstoffen zur erzielung bestimmter producktcharakteristika," *SöFW Journal*, 2005, 1-3 (no English Abstract available).

* cited by examiner

SILICIC ACID ESTER MIXTURES

CROSS-REFERENCE TO RELATED APPLICATIONS

This application is a U.S. National Stage application filed under 35 U.S.C. § 371, claiming priority of International Application No. PCT/EP01/02593, filed Mar. 8, 2001 in the European Patent Office, and DE 100 12 949.8, filed Mar. 16, 2000 in the German Patent Office, under 35 U.S.C. §§ 119 and 365.

BACKGROUND OF THE INVENTION

This invention relates to mixtures of oligomeric silicic acid esters which contain residues of perfume alcohols or biocide alcohols and which may be used, for example, for perfuming detergents because they release the perfume alcohols through hydrolysis.

The controlled release of ingredients in various preparations is the subject of numerous publications and patent applications. In the field of detergents, the accelerated or delayed release of ingredients from the group of bleaching agents, bleach activators, surfactants, etc. is of particular interest. The release of perfumes is of paramount importance in this field because both the product and the wash liquor and the articles treated therewith are intended to be intensively and lastingly perfumed. Besides applying perfumes to carrier materials and coating the perfumed carriers or encapsulating perfumes or incorporating them in compounds (for example cyclodextrin/perfume complexes), perfumes can be chemically bound to carrier media, the chemical bond being slowly broken and the perfume being released. This principle has been put into practice, for example, in the esterification of perfume alcohols, a broad prior art being available on this group of substances.

It is known from the prior art that perfume alcohols can be bound to nonvolatile siloxanes from which they are slowly released by hydrolysis. Although a broad prior art also exists on the subject of siloxane esters of perfume alcohols, problems arise where the compounds mentioned are used in detergents. Thus, many of the known compounds cannot be used in water-containing detergents and cleaners because they hydrolyze in the product itself so that the delayed release no longer occurs. This is all the more the case as conventional detergents often have pH values which further intensify the hydrolysis process. However, known siloxane esters cannot be incorporated in powder-form detergents either. Under typical production conditions for compacted particle mixtures, such as granulation or press agglomeration, the siloxane esters also tend to release the perfume alcohol during the actual production process, i.e. prematurely. Accordingly, there is a need to provide perfumes in supply forms which perfume the product and the wash liquor and substrates treated with the products, the perfume being intended to persist for a long time on textiles in particular.

Monomeric orthosilicic acid esters of perfume alcohols are described, for example, in U.S. Pat. No. 3,215,719 (Dan River Mills). This document also mentions the delayed release of perfuming alcohols from mixed esters such as, for example, bis(eugenoxy)diethoxysilane or bis(cinnamoyloxy)-diethoxysilane, the central Si atom not necessarily having to be bound to oxygen only. Oligomeric siloxane esters are not mentioned in this document.

Powder-form or granular detergent compositions which contain "perfuming" silicon compounds are described in DE 28 44 789 (Dow Corning). The mono-, oligo- and polymeric silicon compounds disclosed in this document do not have to contain a central Si atom surrounded by four oxygen atoms. Oligomeric Si compounds containing more than one perfume alcohol ester group are also not mentioned in this document.

Liquid or paste-form soap compositions containing "perfuming" silicon compounds are described in DE 30 03 494 (Dow Corning). Oligomeric Si compounds containing more than one perfume alcohol ester group are also not described in this document.

Perfuming, nonvolatile siloxanes with the general formula $M_a M'_{a'} D_b D'_{b'} T_c T'_{c'} Q_d$ where M and $M'=R^1 R^2 R^3 SiO_{1/2}$, D and $D'=R^4 R^5 SiO_{2/2}$, T and $T'=R^6 SiO_{3/2}$ and $Q=SiO_{4/2}$, where $R^1$ to $R^6$ independently of one another are selected from $C_{1-40}$ alkyl or alkoxy and $C_{1-40}$ aryl or aryloxy groups and the indices a, a' are positive and one or more of the indices b,b',c,c' and d are positive or 0, are described in DE-A-197 50 706 (General Electric). Formally, oligomeric silicon compounds containing four perfume alcohol ester groups are also covered by the general formula although the document in question explicitly discloses only those compounds in which at least two carbon atoms are directly attached to an Si atom. The use of the perfuming siloxanes in detergents is not mentioned in this document either.

Accordingly, there was still a need to provide more hydrolysis-resistant siloxane esters of perfume alcohols which could even be incorporated in water-containing detergents without showing excessive signs of hydrolysis in the product itself. Another requirement to be satisfied by the compounds in question was that they should lend themselves to incorporation in granular detergent compositions without decomposing in the production process. The compounds to be produced would impart a pleasant and long-lasting perfume to the substrates treated with the solution.

Silicic acid esters corresponding to the formula:

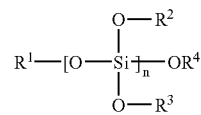

in which $R^1$ and $R^4$ independently of one another are selected from the group of linear or branched, saturated or unsaturated, substituted or unsubstituted $C_{1-6}$ hydrocarbon radicals and perfume alcohol radicals, each $R^2$ and $R^3$ independently of one another is selected from the group of perfume alcohol radicals and n assumes a value of 2 to 20, are described for this purpose in earlier, hitherto unpublished German patent application DE 19841147.2.

It has now been found that mixtures of esters of other oligosilicic acids with perfume alcohols meet the requirements stated above. In studies of these substances, it was also surprisingly found that, in combination with typical perfumes, they also provide the perfumes not esterified with the oligosilicic acids with a relatively long-lasting effect. Irrespective of the chemical composition of the perfumes, therefore, the compounds according to the invention can also be used in perfume mixtures to provide the perfume composition as a whole with prolonged perfume release. It has also been found that this release principle can thus also be applied to biocide alcohols.

DESCRIPTION OF THE INVENTION

The present invention relates to silicic acid ester mixtures containing silicic acid esters corresponding to the following formulae:

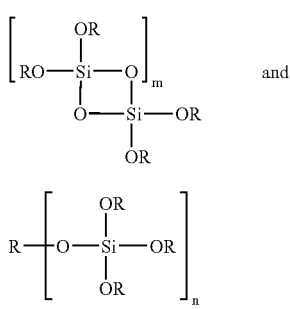

in which all the R's independently of one another are selected from the group consisting of H, linear or branched, saturated or unsaturated, substituted or unsubstituted $C_{1-6}$ hydrocarbon radicals and the perfume alcohols and biocide alcohols and m assumes a value of 1 to 20 and n a value of 2 to 100.

The compounds mentioned are produced by simple transesterification of oligosilicic acid esters of lower alcohols with perfume alcohols or biocide alcohols, for which purpose both individual perfume or biocide alcohols and mixtures of perfume or biocide alcohols may be used. Depending on the reaction time and conditions, the lower alcohols are eliminated and the perfume or biocide alcohols are bound, the alcohols along Si—O—Si chains or rings being more readily exchanged than the terminal alcohols. Transesterifications such as these may be carried out, for example, as described in the article by H. Steinmann, G. Tschernko and H. Hamann in Z. Chem. 3, 1977, pp. 89–92. The content of that article is specifically regarded as disclosure of the present invention for the production of silicic acid esters. Commercially available silicic acid esters are normally used as educts. The ethanol ester obtainable, for example, from Wacker, Burghausen, is particularly mentioned in this connection. The transesterification reaction may be controlled solely by increasing the temperature and distilling off the readily volatile secondary products. However, catalysts are preferably used for the transesterification. The catalysts used are typically Lewis acids, preferably aluminium tetraisopropylate, titanium tetraisopropylate, silicon tetrachloride or basic catalysts or even preparations, for example of aluminium chloride with potassium fluoride. The oligomeric silicic acid esters thus formed then at least partly contain perfume alcohol radicals and/or biocide alcohol radicals or a combination of the two. However, the resulting esters normally also contain residues of lower alcohols. If small quantities of water or other H-acidic compounds are present during the production of the silicic acid esters, alcohol radicals are replaced by OH groups. Accordingly, the silicic acid ester mixtures according to the invention normally also partly contain hydrogen as the substituent R.

Oligosilicic acid esters of lower alcohols are commercially obtainable. methanol, ethanol, n-propanol, isopropanol, n-butanol, isobutanol and tert.butanol being used for the esterification. The preparation of oligosilicic acid esters incompletely transesterified with perfume alcohols leads to silicic acid ester mixtures in which the substituents R are partly selected from the group consisting of methyl, ethyl, n-propyl, isopropyl, n-butyl, isobutyl and tert.butyl. Such compounds are preferred for the purposes of the present invention.

If incompletely transesterified oligosilicic acid esters are produced, the other substituents R are preferably selected from the group of perfume alcohol radicals or biocide alcohol radicals.

"Perfume alcohols" in the context of the invention are understood to be perfumes containing free hydroxyl groups which are esterifiable irrespective of the further structure of the molecule. Thus, salicylic acid esters may also be used as perfume alcohols. From the large group of perfume alcohols, it is possible to name preferred representatives so that preferred silicic acid esters for the purpose of the invention are those in which $R^2$ and $R^3$ independently of one another are each selected from the group of following radicals: 10-undecen-1-ol, 2,6-dimethylheptan-2-ol, 2-methylbutanol, 2-methylpentanol, 2-phenoxyethanol, 2-phenylpropanol, 2-tert.butyl cyclohexanol, 3,5,5-trimethylcyclohexanol, 3-hexanol, 3-methyl-5-phenyl pentanol, 3-octanol, 3-phenylpropanol, 4-heptenol, 4-isopropyl cyclohexanol, 4-tert.butyl cyclohexanol, 6,8-dimethyl-2-nonanol, 6-nonen-1-ol, 9-decen-1-ol, α-methyl benzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethyl benzyl carbinol, dimethyl heptanol, dimethyl octanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-methan-7-ol, phenyl ethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, cinnamyl alcohol.

Biocide alcohols in the context of the present invention are understood to be any compounds which contain at least one alcohol group and which at least inhibit germ growth. Examples of such compounds are alcohols which also act as perfume alcohols. These are, in particular, citronellol, eugenol, farnesol, thymol and geraniol. Other biocide alcohols are phenoxyethanol, 1,2-propylene glycol, glycerol, citric acid and esters thereof, lactic acid and esters thereof, salicylic acid and esters thereof, 2-benzyl-4-chlorophenol and 2,2'-methylene-bis-(6-bromo-4-chlorophenol). The lower alcohols mentioned in the foregoing as typical residues of the silicic acid esters do not count as biocide alcohols in the context of the present invention. Explicitly, methyl, ethyl, n-propyl, isopropyl, n-butyl, isobutyl and tert.butyl alcohol are not regarded as biocide alcohols in the context of the present invention. By contrast, conventional biocides with alcohol functions are expressly regarded as biocide alcohols in the context of the invention even though their effect is attributable to other functional groups. Various bromphenols and biphenylol and quaternary ammonium compounds containing at least one long alkyl chain and at least one alkyl group bearing a hydroxy group are mentioned by way of example in this regard.

The completely transesterified oligosilicic acid esters are particularly preferred for the purposes of the present invention. These are products in which each substituent R is a perfume alcohol or a biocide alcohol. In a particularly preferred embodiment, these esters contain only a single substituent R, i.e. only a single perfume alcohol or biocide alcohol.

The degrees of oligomerization "n" of the silicic acid esters according to the invention are between 2 and 20. In preferred compounds, n assumes a value of 2 to 15, preferably one of 2 to 12, more particularly one of 3 to 10 and, in a particularly preferred embodiment, a value of 4, 5, 6, 7 or 8.

Since, for economic reasons, the starting compounds for the production of the compounds according to the invention are preferably not pure compounds, but instead technical mixtures of oligosilicic acid esters of lower alcohols with different degrees of oligomerization, a distribution of the degree of oligomerization which can correspond to the starting material or which is modified by the reaction conditions is also to be found in the esters according to the invention.

Silicic acid rings as indicated in formula I are often also formed by secondary reactions during the esterification process. In particular, rings containing 3 or 4 silicon atoms are preferably formed. Accordingly, silicic acid ester mixtures containing silicic acid esters corresponding to the following formulae:

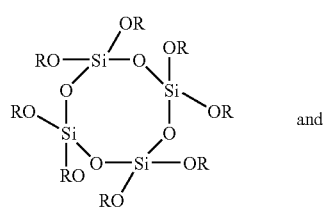
(III)

and

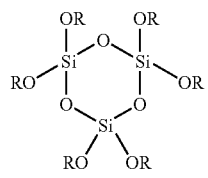
(IV)

are preferred for the purposes of the invention.

The silicic acid esters according to the invention are distinguished by high hydrolysis stability and may even be used in aqueous media or in production processes for granules without undergoing excessive losses of activity. Accordingly, liquid detergent and cleaning compositions, such as liquid detergents, fabric softeners, manual dishwashing detergents, cleaning compositions for hard surfaces, floor cleaners etc. are as conceivable as solid detergent and cleaning compositions, for example granular laundry detergents, dishwasher detergents or scouring compositions. The silicic acid esters according to the invention may also be used in cosmetic skin and hair care preparations. These may again be both liquid preparations, for example shower baths, deodorants and hair shampoos, and solid preparations, for example bar soaps.

By virtue of the outstanding suitability of the compounds according to the invention for use in detergent and cleaning compositions, the present invention also relates to the use of silicic acid ester mixtures containing silicic acid esters corresponding to the following formulae:

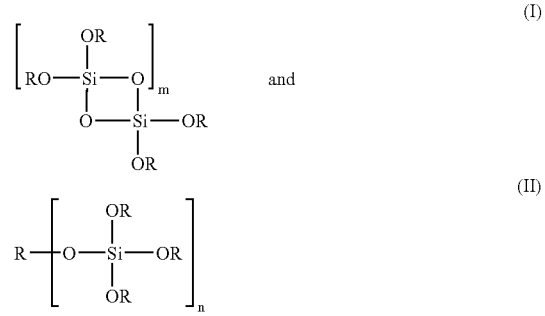

in which all the R's independently of one another are selected from the group consisting of H, linear or branched, saturated or unsaturated, substituted or unsubstituted $C_{1-6}$ hydrocarbon radicals and the perfume alcohol and biocide alcohol radicals and m assumes a value of 1 to 20 and n a value of 2 to 100, as a perfume in liquid or solid detergent and cleaning compositions.

The silicic acid esters are also eminently suitable for use in cosmetic preparations. Accordingly, the present invention also relates to the use of silicic acid ester mixtures containing silicic acid esters corresponding to the following formulae:

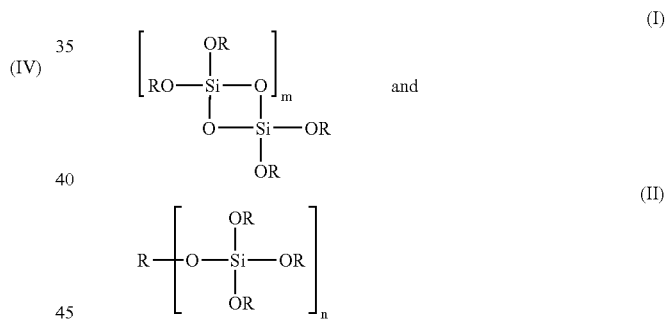

in which all the R's independently of one another are selected from the group consisting of H, linear or branched, saturated or unsaturated, substituted or unsubstituted $C_{1-6}$ hydrocarbon radicals and the perfume alcohols and biocide alcohols and m assumes a value of 1 to 20 and n a value of 2 to 100, as a perfume in cosmetic skin and hair care preparations.

The silicic acid esters according to the invention may be introduced in varying quantities according to the nature of and application envisaged for the compositions to be perfumed. The silicic acid esters corresponding to formulae I and II are normally introduced in quantities of 0.001 to 10% by weight, preferably in quantities of 0.01 to 5% by weight, more preferably in quantities of 0.02 to 3% by weight and, in one particular embodiment, in quantities of 0.05 to 2% by weight, based on the particular composition.

The silicic acid esters according to the invention may be used as sole perfume although it is also possible to use perfume mixtures which consist only partly of the silicic acid esters according to the invention. Such mixtures have the advantage that even those constituents of the perfume mixture which are not present as esterified perfume alcohols are improved in regard to the persistence of the perfume impression. More particularly, it is possible to use perfume mixtures containing 1 to 50% by weight, preferably 5 to 40% by weight and more particularly at most 30% by weight of silicic acid ester. In other embodiments where, above all, the delayed perfume effect of the esterified perfume alcohols is to be utilized, advantageously at least 30% by weight, preferably at least 40% by weight and more particularly at least 50% by weight of the total perfume present in the composition are introduced through the silicic acid esters according to the invention used in accordance with the invention while the remaining 70% by weight, preferably 60% by weight and more particularly 50% by weight of the total perfume present in the composition is sprayed on in the usual way or otherwise introduced into the composition. Accordingly, the use according to the invention may advantageously be characterized in that the silicic acid esters corresponding to formulae I and II are used together with other perfumes.

By dividing the total perfume content of the compositions into perfume present in the silicic acid esters and conventionally incorporated perfume, it is possible to achieve a number of product features which are only possible through the use according to the invention. For example, the total perfume content of the compositions can be divided into two portions x and y, portion x consisting of firmly adhering perfume oils, i.e. less volatile perfume oils, and portion y consisting of more volatile perfume oils.

Now, it is possible to produce detergent/cleaning compositions where the percentage of perfume introduced into the detergent through the silicic acid esters is mainly made up of firmly adhering perfumes. In this way, firmly adhering perfumes which are intended to perfume the treated articles, more especially textiles, are "retained" in the product and thus develop their effect primarily on the treated laundry. By contrast, the more readily volatile perfumes contribute towards more intensive perfuming of the detergent/cleaning compositions per se. In this way, it is also possible to produce detergent/cleaning compositions which, as compositions, have a perfume that differs from the perfume of the treated articles. There are virtually no limits in this regard to the creativity of perfumists because almost limitless possibilities for perfuming the compositions and—through the compositions—the articles treated with them exist on the one hand through the choice of the perfumes and on the other hand through the choice of the method used to incorporate them in the compositions.

The principle described above can of course also be reversed by incorporating the more readily volatile perfumes in the silicic acid esters and spraying the less volatile firmly adhering perfumes onto the compositions. In this way, the loss of the more readily volatile perfumes from the pack in storage and in transit is minimized while the perfume characteristic of the detergents is determined by the more firmly adhering perfumes.

The only limiting aspect of this procedure is that the perfumes to be introduced via the silicic acid esters according to the invention emanate from the group of perfume alcohols. The perfumes conventionally incorporated in the detergent/cleaning compositions are not subject to any limitations. Thus, the perfume oils or perfumes used may be individual perfume compounds, for example synthetic products of the ester, ether, aldehyde, ketone, alcohol and hydrocarbon type. Examples of perfume compounds of the ester type are benzyl acetate, phenoxyethyl isobutyrate, p-tert.butyl cyclohexyl acetate, linalyl acetate, dimethyl benzyl carbinyl acetate (DMBCA), phenyl ethyl acetate, benzyl acetate, ethyl methyl phenyl glycinate, allyl cyclohexyl propionate, styrallyl propionate, benzyl salicylate, cyclohexyl salicylate, floramat, melusate and jasmecyclate. The ethers include, for example, benzyl ethyl ether and Ambroxan; the aldehydes include, for example, linear alkanals containing 8 to 18 carbon atoms, citral, citronellal, citronellyloxy acetaldehyde, cyclamen aldehyde, lilial and bourgeonal; the ketones include, for example, ionones, α-isomethyl ionone and methyl cedryl ketone; the alcohols include anethol, citronellol, eugenol, geraniol, linalool, phenyl ethyl alcohol and terpineol while the hydrocarbons include, above all, terpenes, such as limonene and pinene. However, mixtures of different perfumes which together produce an attractive perfume note are preferably used.

Perfume oils such as these may also contain natural perfume mixtures obtainable from vegetable sources, for example pine, citrus, jasmine, patchouli, rose or ylang-ylang oil. Also suitable are clary oil, camomile oil, clove oil, melissa oil, mint oil, cinnamon leaf oil, lime blossom oil, juniper berry oil, vetiver oil, olibanum oil, galbanum oil and ladanum oil and orange blossom oil, neroli oil, orange peel oil and sandalwood oil.

The general description of the perfumes suitable for use in accordance with the invention (see above) represents the various classes of perfumes in general terms. In order to be noticeable, a perfume has to be volatile, its molecular weight being an important factor along with the nature of the functional groups and the structure of the chemical compound. Thus, most perfumes have molecular weights of up to about 200 dalton, molecular weights of 300 dalton and higher being more the exception. In view of the differences in volatility of perfumes, the odor of a perfume or fragrance composed of several perfumes changes during the evaporation process, the odor impressions being divided into the top note, the middle note or body and the end note or dry out. Since odor perception is also based to a large extent on odor intensity, the top note of a perfume or fragrance does not consist solely of readily volatile compounds whereas the end note or dry out consists largely of less volatile, i.e. firmly adhering, perfumes. In the composition of perfumes, more readily volatile perfumes may be fixed, for example, to certain "fixatives", which prevents them from vaporizing too rapidly. The above-described embodiment of the present invention, in which the more readily volatile perfumes or fragrances are incorporated in the silicic acid esters according to the invention, is one such method of fixing a perfume. Accordingly, in the following classification of perfumes into "readily volatile" and "firmly adhering" perfumes, nothing is said about the odor impression or about whether the corresponding perfume is perceived as a top note or middle note.

Firmly adhering perfumes suitable for use in accordance with the present invention are, for example, the essential oils, such as angelica root oil, aniseed oil, arnica flowers oil, basil oil, bay oil, champax blossom oil, silver fir oil, silver fir cone oil, elemi oil, eucalyptus oil, fennel oil, pine needle oil, galbanum oil, geranium oil, ginger grass oil, guaiac wood oil, Indian wood oil, helichrysum oil, ho oil, ginger oil, iris oil, cajeput oil, sweet flag oil, camomile oil, camphor oil, canaga oil, cardamom oil, cassia oil, Scotch fir oil, copaiba balsam oil, coriander oil, spearmint oil, caraway oil, cumin oil, lavender oil, lemon grass oil, limette oil, mandarin oil, melissa oil, amber seed oil, myrrh oil, clove oil, neroli oil, niaouli oil, olibanum oil, orange oil, origanum oil, palmarosa oil, patchouli oil, Peru balsam oil, petit grain oil, pepper oil, peppermint oil, pimento oil, pine oil, rose oil, rosemary oil, sandalwood oil, celery seed oil, lavender spike oil, Japanese anise oil, turpentine oil, thuja oil, thyme oil, verbena oil, vetiver oil, juniper berry oil, wormwood oil, wintergreen oil, ylang-ylang oil, ysop oil, cinnamon oil, cinnamon leaf oil, citronella oil, citrus oil and cypress oil. However, relatively high-boiling or solid perfumes of natural or synthetic origin may also be used in accordance with the invention as firmly adhering perfumes or perfume mixtures. These compounds include those mentioned in the following and mixtures thereof: ambrettolide, α-amyl cinnamaldehyde, anethole, anisaldehyde, anisalcohol, anisole, methyl anthranilate, acetophenone, benzyl acetone, benzaldehyde, ethyl benzoate, benzophenone, benzyl alcohol, benzyl acetate, benzyl benzoate, benzyl formate, benzyl valerate, borneol, bornyl acetate, Boisambrene forte, α-bromostyrene, n-decyl aldehyde, n-dodecyl aldehyde, eugenol, eugenol methyl ether, eucalyptol, farnesol, fenchone, fenchyl acetate, geranyl acetate, geranyl formiate, heliotropin, methyl heptyne carboxylate, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarin, p-methoxyacetophenone, methyl-n-amyl ketone, methyl anthranilic acid methyl ester, p-methyl acetophenone, methyl chavicol, p-methyl quinoline, methyl-β-naphthyl ketone, methyl-n-nonyl acetaldehyde, methyl-n-nonyl ketone, muskone, β-naphthol ethyl ether, β-naphthol methyl ether, nerol, n-nonyl aldehyde, nonyl alcohol, n-octyl aldehyde, p-oxyacetophenone, pentadecanolide, β-phenyl ethyl alcohol, phenyl acetaldehyde dimethyl acetal, phenyl acetic acid, pulegone, safrol, isoamyl salicylate, methyl salicylate, hexyl salicylate, cyclohexyl salicylate, santalol, sandelice, scatol, terpineol, thymene, thymol, troenan, γ-undecalactone, vanillin, veratrum aldehyde, cinnamaldehyde, cinnamyl alcohol, cinnamic acid, ethyl cinnamate, benzyl cinnamate.

The more readily volatile perfumes include, in particular, the relatively low-boiling perfumes of natural or synthetic origin which may be used either individually or in the form of mixtures. Examples of more readily volatile perfumes are diphenyl oxide, limonene, linalool, linalyl acetate and propionate, melusate, menthol, menthone, methyl-nheptenone, pinene, phenyl acetaldehyde, terpinyl acetate, citral, citronellal.

The fact that not only the chemically bound perfume alcohols, but also the perfumes merely present in admixture with the silicic acid esters according to the invention are released with delay and hence persist for longer is surprising. Accordingly, the present invention also relates to the use of silicic acid ester mixtures containing silicic acid esters corresponding to the following formulae:

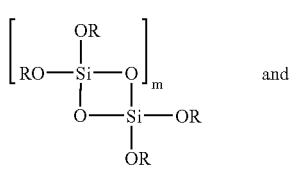

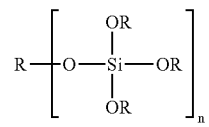

in which all the R's independently of one another are selected from the group consisting of H, linear or branched, saturated or unsaturated, substituted or unsubstituted $C_{1-6}$ hydrocarbon radicals and the perfume alcohols and biocide alcohols and m assumes a value of 1 to 20 and n a value of 2 to 100, for prolonging the perfume effect of other perfumes.

The present invention also relates to the use of silicic acid ester mixtures containing silicic acid esters corresponding to the following formulae:

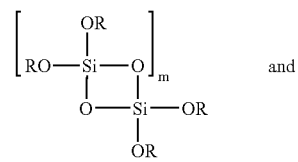

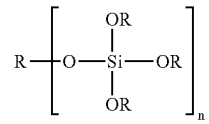

in which all the R's independently of one another are selected from the group consisting of H, linear or branched, saturated or unsaturated, substituted or unsubstituted $C_{1-6}$ hydrocarbon radicals and the perfume alcohols and biocide alcohols and m assumes a value of 1 to 20 and n a value of 2 to 100, as a biocide in liquid or solid detergent and cleaning compositions.

The biocide alcohol/silicic acid esters are also eminently suitable for use in cosmetic preparations. Accordingly, the present invention also relates to the use of silicic acid ester mixtures containing silicic acid esters corresponding to the following formulae:

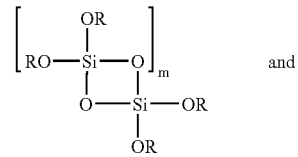

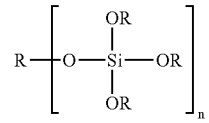

in which all the R's independently of one another are selected from the group consisting of H, linear or branched, saturated or unsaturated, substituted or unsubstituted $C_{1-6}$ hydrocarbon radicals and the perfume alcohols and biocide alcohols and m assumes a value of 1 to 20 and n a value of 2 to 100, as a biocide in cosmetic skin and hair care preparations.

The silicic acid esters according to the invention may be introduced in varying quantities according to the nature of and application envisaged for the compositions. The silicic acid esters corresponding to formulae I and II are normally introduced in quantities of 0.001 to 10% by weight, preferably in quantities of 0.01 to 5% by weight, more preferably in quantities of 0.02 to 3% by weight and, in one particular embodiment, in quantities of 0.05 to 2% by weight, based on the particular composition. The exact quantities depend in particular on whether the biocides are merely intended to develop a preserving effect for the composition or whether they are intended to be germicidal in use. It is not a problem for the biocide expert to find a dosage appropriate to the particular application.

If the biocides are to be used for preservation purposes, the use of the silicic acid esters according to the invention is of particular advantage because the biocide component is uniformly released in small quantities over a long period through the slow hydrolysis of the esters which takes place under the influence of moisture. For example, skin creams can thus be preserved with extremely low doses of biocide.

However, where they are used in detergents in particular, the germicidal effect of the biocides can also be of paramount importance in the practical application of the detergent. It has been found in this connection that, as with the perfumes, the biocide alcohol/silicic acid esters improve the absorption of the biocides onto the fabric and hence lead to an increased effect for the same quantity of biocide used.

Accordingly, the present invention also relates to detergent and cleaning compositions which contain silicic acid ester mixtures containing silicic acid esters corresponding to the following formulae:

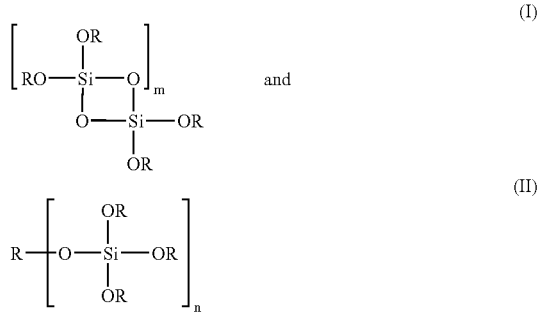

in which all the R's independently of one another are selected from the group consisting of H, linear or branched, saturated or unsaturated, substituted or unsubstituted $C_{1-6}$ hydrocarbon radicals and the perfume alcohols and biocide alcohols and m assumes a value of 1 to 20 and n a value of 2 to 100. The compositions contain silicic acid esters corresponding to formulae I and II in quantities of 0.001 to 10% by weight, preferably 0.01 to 5% by weight, more preferably 0.02 to 3% by weight and, in one particular embodiment, in quantities of 0.05 to 2% by weight, based on the detergent/cleaning composition. As mentioned above, the compositions may contain other perfumes or biocides besides these silicic acid esters.

Apart from the perfumes and biocides, the detergent/cleaning compositions may of course also contain ingredients typical of such compositions. Surfactants, builders and bleaching agents, enzymes and other active substances are particularly mentioned in this regard. Key ingredients of detergent/cleaning compositions are in particular surfactants.

The surfactant content selected for the compositions according to the invention will be relatively high or relatively low according to the intended application. The surfactant content of laundry detergents is normally between 10 and 40% by weight, preferably between 12.5 and 30% by weight and more particularly between 15 and 25% by weight whereas dishwasher detergents contain between 0.1 and 10% by weight, preferably between 0.5 and 7.5% by weight and more particularly between 1 and 5% by weight of surfactants.

These surface-active substances emanate from the group of anionic, nonionic, zwitterionic or cationic surfactants, anionic surfactants being much preferred for economic reasons and for their performance spectrum in washing and cleaning.

The anionic surfactants used are, for example, those of the sulfonate and sulfate type. Preferred surfactants of the sulfonate type are $C_{9-13}$ alkyl benzenesulfonates, olefin sulfonates, i.e. mixtures of alkene and hydroxyalkane sulfonates, and the disulfonates obtained, for example, from $C_{12-18}$ monoolefins with an internal or terminal double bond by sulfonation with gaseous sulfur trioxide and subsequent alkaline or acidic hydrolysis of the sulfonation products. Other suitable surfactants of the sulfonate type are the alkane sulfonates obtained from $C_{12-18}$ alkanes by sulfochlorination or sulfoxidation and subsequent hydrolysis or neutralization. The esters of α-sulfofatty acids (ester sulfonates), for example the α-sulfonated methyl esters of hydrogenated coconut oil, palm kernel oil or tallow fatty acids, are also suitable.

Other suitable anionic surfactants are sulfonated fatty acid glycerol esters, i.e. the monoesters, diesters and triesters and mixtures thereof which are obtained where production is carried out by esterification by a monoglycerol with 1 to 3 moles of fatty acid or in the transesterification of triglycerides with 0.3 to 2 moles of glycerol. Preferred sulfonated fatty acid glycerol esters are the sulfonation products of saturated $C_{6-22}$ fatty acids, for example caproic acid, caprylic acid, capric acid, myristic acid, lauric acid, palmitic acid, stearic acid or behenic acid.

Preferred alk(en)yl sulfates are the alkali metal salts and, in particular, the sodium salts of the sulfuric acid semiesters of $C_{12-18}$ fatty alcohols, for example coconut alcohol, tallow alcohol, lauryl, myristyl, cetyl or stearyl alcohol, or $C_{10-20}$ oxoalcohols and the corresponding semiesters of secondary alcohols with the same chain length. Other preferred alk(en)yl sulfates are those with the chain length mentioned which contain a synthetic, linear alkyl chain based on a petrochemical and which are similar in their degradation behavior to the corresponding compounds based on oleochemical raw materials. $C_{12-16}$ alkyl sulfates and $C_{12-15}$ alkyl sulfates and also $C_{14-15}$ alkyl sulfates alkyl sulfates are particularly preferred from the washing performance perspective. Other suitable anionic surfactants are 2,3-alkyl sulfates which may be produced, for example, in accordance with U.S. Pat. No. 3,234,258 or U.S. Pat. No. 5,075,041 and which are commercially obtainable as products of the Shell Oil Company under the name of DAN®.

The sulfuric acid monoesters of linear or branched $C_{7-21}$ alcohols ethoxylated with 1 to 6 moles of ethylene oxide, such as 2-methyl-branched $C_{9-11}$ alcohols containing on average 3.5 moles of ethylene oxide (EO) or $C_{12-18}$ fatty alcohols containing 1 to 4 EO, are also suitable. In view of their high foaming capacity, they are normally used in only relatively small quantities, for example in quantities of 1 to 5% by weight, in dishwashing detergents.

Other suitable anionic surfactants are the salts of alkyl sulfosuccinic acid which are also known as sulfosuccinates or as sulfosuccinic acid esters and which represent monoesters and/or diesters of sulfosuccinic acid with alcohols, preferably fatty alcohols and, more particularly, ethoxylated fatty alcohols. Preferred sulfosuccinates contain $C_{8-18}$ fatty alcohol molecules or mixtures thereof. Particularly preferred sulfosuccinates contain a fatty alcohol molecule derived from ethoxylated fatty alcohols which, considered in isolation, represent nonionic surfactants (for a description, see below). Of these sulfosuccinates, those of which the fatty alcohol molecules are derived from narrow-range ethoxylated fatty alcohols are particularly preferred. Alk(en)yl succinic acid preferably containing 8 to 18 carbon atoms in the alk(en)yl chain or salts thereof may also be used.

Other suitable anionic surfactants are, in particular, soaps. Suitable soaps are, in particular, saturated fatty acid soaps, such as the salts of lauric acid, myristic acid, palmitic acid, stearic acid, hydrogenated erucic acid and behenic acid, and soap mixtures derived in particular from natural fatty acids, for example coconut, palm kernel or tallow fatty acids.

The anionic surfactants, including the soaps, may be present in the form of their sodium, potassium or ammonium salts and as soluble salts of organic bases, such as mono-, di- or triethanolamine. The anionic surfactants are preferably present in the form of their sodium, potassium or magnesium salts and, more preferably, in the form of their sodium salts.

So far as the choice of anionic surfactants is concerned, there are no basic requirements to restrict the freedom of formulation. However, preferred detergent compositions do have a soap content in excess of 0.2% by weight, based on the total weight of the granules produced in step d). Preferred anionic surfactants are alkyl benzenesulfonates and fatty alcohol sulfates, preferred detergent tablets containing 2 to 20% by weight, preferably 2.5 to 15% by weight and more preferably 5 to 10% by weight of fatty alcohol sulfate(s), based on the weight of the granules.

Preferred nonionic surfactants are alkoxylated, advantageously ethoxylated, more especially primary alcohols preferably containing 8 to 18 carbon atoms and, on average, 1 to 12 mol of ethylene oxide (EO) per mol of alcohol, in which the alcohol component may be linear or, preferably, methyl-branched in the 2-position or may contain linear and methyl-branched residues in the form of the mixtures typically present in oxoalcohol residues. However, alcohol ethoxylates containing linear residues of alcohols of native origin with 12 to 18 carbon atoms, for example coconut oil, palm oil, tallow fatty or oleyl alcohol, and on average 2 to 8 EO per mol of alcohol are particularly preferred. Preferred ethoxylated alcohols include, for example, $C_{12-14}$ alcohols containing 3 EO or 4 EO, $C_{9-11}$ alcohol containing 7 EO, $C_{13-15}$ alcohols containing 3 EO, 5 EO, 7 EO or 8 EO, $C_{12-18}$ alcohols containing 3 EO, 5 EO or 7 EO and mixtures thereof, such as mixtures of $C_{12-14}$ alcohol containing 3 EO and $C_{12-18}$ alcohol containing 5 EO. The degrees of ethoxylation mentioned represent statistical mean values which, for a special product, can be a whole number or a broken number. Preferred alcohol ethoxylates have a narrow homolog distribution (narrow range ethoxylates, NRE). In addition to these nonionic surfactants, fatty alcohols containing more than 12 EO may also be used, examples including tallow fatty alcohol containing 14 EO, 25 EO, 30 EO or 40 EO.

Another class of preferred nonionic surfactants which may be used either as sole nonionic surfactant or in combination with other nonionic surfactants are alkoxylated, preferably ethoxylated or ethoxylated and propoxylated, fatty acid alkyl esters preferably containing 1 to 4 carbon atoms in the alkyl chain, more especially the fatty acid methyl esters which are described, for example, in Japanese patent application JP 58/217598 or which are preferably produced by the process described in International patent application WO-A-90/13533.

Another class of nonionic surfactants which may advantageously be used are the alkyl polyglycosides (APGs). Suitable alkyl polyglycosides correspond to the general formula $RO(G)_z$ where R is a linear or branched, more particularly 2-methyl-branched, saturated or unsaturated aliphatic radical containing 8 to 22 and preferably 12 to 18 carbon atoms and G stands for a glycose unit containing 5 or 6 carbon atoms, preferably glucose. The degree of glycosidation z is between 1.0 and 4.0, preferably between 1.0 and 2.0 and more preferably between 1.1 and 1.4.

Linear alkyl polyglycosides, i.e. alkyl polyglycosides in which the polyglycosyl component is a glucose unit and the alkyl component is an n-alkyl group, are preferably used.

The surfactant granules may advantageously contain alkyl polyglycosides, APG contents of more than 0.2% by weight, based on the tablet as a whole, being preferred. Particularly preferred detergent tablets contain APGs in quantities of 0.2 to 10% by weight, preferably in quantities of 0.2 to 5% by weight and more preferably in quantities of 0.5 to 3% by weight.

Nonionic surfactants of the amine oxide type, for example N-cocoalkyl-N,N-dimethylamine oxide and N-tallowalkyl-N,N-dihydroxyethylamine oxide, and the fatty acid alkanolamide type are also suitable. The quantity in which these nonionic surfactants are used is preferably no more than the quantity in which the ethoxylated fatty alcohols are used and, more preferably, no more than half that quantity.

Other suitable surfactants are polyhydroxyfatty acid amides corresponding to formula (V):

(V)

in which RCO is an aliphatic acyl group containing 6 to 22 carbon atoms, $R^1$ is hydrogen, an alkyl or hydroxyalkyl group containing 1 to 4 carbon atoms and [Z] is a linear or branched polyhydroxyalkyl group containing 3 to 10 carbon atoms and 3 to 10 hydroxyl groups. The polyhydroxyfatty acid amides are known substances which may normally be obtained by reductive amination of a reducing sugar with ammonia, an alkylamine or an alkanolamine and subsequent acylation with a fatty acid, a fatty acid alkyl ester or a fatty acid chloride.

The group of polyhydroxyfatty acid amides also includes compounds corresponding to formula (VI):

$$\begin{array}{c} R^1\!-\!O\!-\!R^2 \\ | \\ R\!-\!CO\!-\!N\!-\![Z] \end{array} \quad (VI)$$

in which R is a linear or branched alkyl or alkenyl group containing 7 to 12 carbon atoms, $R^1$ is a linear, branched or cyclic alkyl group or an aryl group containing 2 to 8 carbon atoms and $R^2$ is a linear, branched or cyclic alkyl group or an aryl group or an oxyalkyl group containing 1 to 8 carbon atoms, $C_{1-4}$ alkyl or phenyl groups being preferred, and [Z] is a linear polyhydroxyalkyl group, of which the alkyl chain is substituted by at least two hydroxyl groups, or alkoxylated, preferably ethoxylated or propoxylated, derivatives of that group.

[Z] is preferably obtained by reductive amination of a reduced sugar, for example glucose, fructose, maltose, lactose, galactose, mannose or xylose. The N-alkoxy- or N-aryloxy-substituted compounds may then be converted into the required polyhydroxyfatty acid amides by reaction with fatty acid methyl esters in the presence of an alkoxide as catalyst, for example in accordance with the teaching of International patent application WO-A-95/07331.

Another significant group of detergent ingredients are the builders. This class of substances is understood to encompass both organic and inorganic builders. These are compounds which may both perform a carrier function in the granules according to the invention and act as a water-softening substance in use.

Useful organic builders are, for example, the polycarboxylic acids usable, for example, in the form of their sodium salts (polycarboxylic acids in this context being understood to be carboxylic acids carrying more than one acid function). Examples include citric acid, adipic acid, succinic acid, glutaric acid, malic acid, tartaric acid, maleic acid, fumaric acid, sugar acids, aminocarboxylic acids, nitrilotriacetic acid (NTA), providing its use is not ecologically unsafe, and mixtures thereof. Preferred salts are the salts of the polycarboxylic acids, such as citric acid, adipic acid, succinic acid, glutaric acid, tartaric acid, sugar acids and mixtures thereof.

The acids per se may also be used. Besides their builder effect, the acids typically have the property of an acidifying component and, accordingly, are also used to establish a lower and more mild pH value in laundry or dishwashing detergents. Citric acid, succinic acid, glutaric acid, adipic acid, gluconic acid and mixtures thereof are particularly mentioned in this regard.

Other suitable builders are polymeric polycarboxylates such as, for example, the alkali metal salts of polyacrylic acid or polymethacrylic acid, for example those having a relative molecular weight of 500 to 70,000 g/mole. This class of substances is described in detail in the foregoing. The (co)polymeric polycarboxylates may be used either in powder form or as an aqueous solution. The content of (co)polymeric polycarboxylates in the granules is preferably 0.5 to 20% by weight and more particularly 3 to 10% by weight.

In order to improve their solubility in water, the polymers may also contain allyl sulfonic acids, for example allyloxybenzenesulfonic acid and methallyl sulfonic acid (cf. for example EP-B-0 727 448), as monomer. Biodegradable polymers of more than two different monomer units are also particularly preferred, examples including those which contain salts of acrylic acid and maleic acid and vinyl alcohol or vinyl alcohol derivatives as monomers (DE-A-43 00 772) or those which contain salts of acrylic acid and 2-alkylallyl sulfonic acid and sugar derivatives as monomers (DE-C-42 21 381). Other preferred copolymers are those described in German patent applications DE-A-43 03 320 and DE-A-44 17 734 which preferably contain acrolein and acrylic acid/acrylic acid salts or acrolein and vinyl acetate as monomers. Other preferred builders are polymeric aminodicarboxylic acids, salts or precursors thereof. Polyaspartic acids or salts and derivatives thereof which, according to German patent application DE-A-195 40 086, have a bleach-stabilizing effect in addition to their co-builder properties are particularly preferred.

Other suitable builders are polyacetals which may be obtained by reaction of dialdehydes with polyol carboxylic acids containing 5 to 7 carbon atoms and at least three hydroxyl groups, for example as described in European patent application EP-A-0 280 223. Preferred polyacetals are obtained from dialdehydes, such as glyoxal, glutaraldehyde, terephthalaldehyde and mixtures thereof and from polyol carboxylic acids, such as gluconic acid and/or glucoheptonic acid.

Other suitable organic builders are dextrins, for example oligomers or polymers of carbohydrates which may be obtained by partial hydrolysis of starches. The hydrolysis may be carried out by standard methods, for example acid- or enzyme-catalyzed methods. The end products are preferably hydrolysis products with average molecular weights of 400 to 500,000 g/mol. A polysaccharide with a dextrose equivalent (DE) of 0.5 to 40 and, more particularly, 2 to 30 is preferred, the DE being an accepted measure of the reducing effect of a polysaccharide by comparison with dextrose which has a DE of 100. Both maltodextrins with a DE of 3 to 20 and dry glucose syrups with a DE of 20 to 37 and also so-called yellow dextrins and white dextrins with relatively high molecular weights of 2,000 to 30,000 g/mol may be used. A preferred dextrin is described in British patent application 94 19 091. The oxidized derivatives of such dextrins are their reaction products with oxidizing agents which are capable of oxidizing at least one alcohol function of the saccharide ring to the carboxylic acid function. Dextrins thus oxidized and processes for their production are known, for example, from European patent applications EP-A-0 232 202, EP-A-0 427 349, EP-A-0 472 042 and EP-A-0 542 496 and from International patent applications WO 92/18542, WO-A-93/08251, WO-A-93/16110, WO-A-94/28030, WO-A-95/07303, WO-A-95/12619 and WO-A-95/20608. An oxidized oligosaccharide according to German patent application DE-A-196 00 018 is also suitable. A product oxidized at $C_6$ of the saccharide ring can be particularly advantageous.

Other suitable co-builders are oxydisuccinates and other derivatives of disuccinates, preferably ethylenediamine disuccinate. Ethylenediamine-N,N'-disuccinate (EDDS), of which the synthesis is described, for example, in U.S. Pat. No. 3,158,615, is preferably used in the form of its sodium or magnesium salts. Glycerol disuccinates and glycerol trisuccinates as described, for example, in U.S. Pat. Nos. 4,524,009 and 4,639,325, in European patent application EP-A-0 150 930 and in Japanese patent application JP 93/339896 are also particularly preferred in this connection. The quantities used in zeolite-containing and/or silicate-containing formulations are from 3 to 15% by weight.

Other useful organic co-builders are, for example, acetylated hydroxycarboxylic acids and salts thereof which may optionally be present in lactone form and which contain at least 4 carbon atoms, at least one hydroxy group and at most two acid groups. Co-builders such as these are described, for example, in International patent application WO-A-95/20029.

Another class of substances with co-builder properties are the phosphonates, more particularly hydroxyalkane and aminoalkane phosphonates. Among the hydroxyalkane phosphonates, 1-hydroxyethane-1,1-diphosphonate (HEDP) is particularly important as a co-builder. It is preferably used in the form of a sodium salt, the disodium salt showing a neutral reaction and the tetrasodium salt an alkaline ration (pH 9). Preferred aminoalkane phosphonates are ethylenediamine tetramethylene phosphonate (EDTMP), diethylenetriamine pentamethylene phosphonate (DTPMP) and higher homologs thereof. They are preferably used in the form of the neutrally reacting sodium salts, for example as the hexasodium salt of EDTMP and as the hepta- and octasodium salt of DTPMP. Within the class of phosphonates, HEDP is preferably used as builder. The aminoalkane phosphonates also show a pronounced heavy metal binding capacity. Accordingly, it can be of advantage, particularly where the detergents also contain bleaching agents, to use aminoalkane phosphonates, more especially DTPMP, or mixtures of the phosphonates mentioned.

In addition, any compounds capable of forming complexes with alkaline earth metal ions may be used as co-builders.

A preferred inorganic builder is finely crystalline, synthetic zeolite containing bound water, preferably zeolite A, X and/or P. A particularly preferred zeolite P is, for example, zeolite MAP (for example Doucil® A24, a product of Crosfield). Also suitable, however, are zeolite X and mixtures of A, X and/or P, for example a co-crystallizate of zeolite A and zeolite X which is marketed under the name of VEGOBOND AX® (by Condea Augusta S.p.A.). The zeolite may be used as a spray-dried powder or even as an undried stabilized suspension still moist from its production. Where the zeolite is used in the form of a suspension, the suspension may contain small additions of nonionic surfactants as stabilizers, for example 1 to 3% by weight, based on zeolite, of ethoxylated $C_{12-18}$ fatty alcohols containing 2 to 5 ethylene oxide groups, $C_{12-14}$ fatty alcohols containing 4 to 5 ethylene oxide groups or ethoxylated isotridecanols. Suitable zeolites have a mean particle size of less than 10 µm (volume distribution, as measured by the Coulter Counter method) and contain preferably 18 to 22% by weight and, more preferably, 20 to 22% by weight of bound water. In preferred embodiments, the premix contains zeolites in quantities of 10 to 94.5% by weight and, in particularly preferred embodiments, in quantities of 20 to 70% by weight and more particularly 30 to 60% by weight.

Suitable substitutes or partial substitutes for the zeolite are layer silicates of natural and synthetic origin. Layer silicates such as these are known, for example, from patent applications DE-A-23 34 899, EP-A-0 026 529 and DE-A-35 36 405. Their suitability is not confined to a particular composition or structural formula, although smectites and especially bentonites are preferred. Crystalline layer-form sodium silicates corresponding to the general formula NaMSi$_x$O$_{2x+1}$ yH$_2$O, where M is sodium or hydrogen, x is a number of 1.9 to 4 and y is a number of 0 to 20, preferred values for x being 2, 3 or 4, are also suitable substitutes for zeolites and phosphates. Crystalline layer silicates such as these are described, for example, in European patent application EP-A-0 164 514. Preferred crystalline layer silicates corresponding to the above formula are those in which M is sodium and x assumes the value 2 or 3. Both β- and δ-sodium disilicates Na$_2$Si$_2$O$_5$ yH$_2$O are particularly preferred.

Other preferred builders are amorphous sodium silicates with a modulus (Na$_2$O:SiO$_2$ ratio) of 1:2 to 1:3.3, preferably 1:2 to 1:2.8 and more preferably 1:2 to 1:2.6 which dissolve with delay and exhibit multiple wash cycle properties. The delay in dissolution in relation to conventional amorphous sodium silicates can have been obtained in various ways, for example by surface treatment, compounding, compacting or by overdrying. In the context of the invention, the term "amorphous" is also understood to encompass "X-ray amorphous". In other words, the silicates do not produce any of the sharp X-ray reflexes typical of crystalline substances in X-ray diffraction experiments, but at best one or more maxima of the scattered X-radiation which have a width of several degrees of the diffraction angle. Particularly good builder properties may even be achieved where the silicate particles produce crooked or even sharp diffraction maxima in electron diffraction experiments. This may be interpreted to mean that the products have microcrystalline regions between 10 and a few hundred nm in size, values of up to at most 50 nm and, more particularly, up to at most 20 nm being preferred. So-called X-ray amorphous silicates such as these, which also dissolve with delay in relation to conventional waterglasses, are described for example in German patent application DE-A-44 00 024. Compacted amorphous silicates, compounded amorphous silicates and overdried X-ray-amorphous silicates are particularly preferred, the overdried silicates in particular preferably also occurring as carriers in the granules according to the invention or being used as carriers in the process according to the invention.

The generally known phosphates may of course also be used as builders providing their use is not ecologically problematical. The sodium salts of orthophosphates, pyrophosphates and, in particular, tripolyphosphates are particularly suitable. Their content is generally no more than 25% by weight and preferably no more than 20% by weight, based on the final detergent. In some cases, it has been found that tripolyphosphates in particular, even in small quantities of up to at most 10% by weight, based on the final detergent, produce a synergistic improvement in multiple wash cycle performance in combination with other builders.

Besides the constituents mentioned, the detergents according to the invention may additionally contain one or more substances from the group of bleaching agents, bleach activators, enzymes, pH adjusters, fluorescers, dyes, foam inhibitors, silicone oils, redeposition inhibitors, optical brighteners, discoloration inhibitors, dye transfer inhibitors, corrosion inhibitors and silver protectors. These components are described in the following.

Among the compounds yielding H$_2$O$_2$ in water which serve as bleaching agents, sodium perborate tetrahydrate, sodium perborate monohydrate-and sodium percarbonate are particularly important. Other useful bleaching agents are, for example, peroxypyrophosphates, citrate perhydrates and H$_2$O$_2$-yielding peracidic salts or peracids, such as perbenzoates, peroxophthalates, diperazelaic acid, phthaloiminoperacid or diperdodecane dioic acid. Even where bleaching agents are used, it is possible to leave out surfactants and/or builders so that pure bleach tablets can be produced. If such bleach tablets are to be used for washing laundry, a combination of sodium percarbonate with sodium sesquicarbonate is preferably used irrespective of what other ingredients the tablets contain. If detergent or bleach tablets for dishwashing machines are being produced, bleaching agents from the group of organic bleaches may also be used. Typical organic bleaching agents are diacyl peroxides, such as dibenzoyl peroxide for example. Other typical organic bleaching agents are the peroxy acids, of which alkyl peroxy acids and aryl peroxy acids are particularly mentioned as examples. Preferred representatives are (a) peroxybenzoic acid and ring-substituted derivatives thereof, such as alkyl peroxybenzoic acids, but also peroxy-α-naphthoic acid and magnesium monoperphthalate, (b) aliphatic or substituted aliphatic peroxy acids, such as peroxylauric acid, peroxystearic acid, ε-phthalimidoperoxycaproic acid [phthaloiminoperoxyhexanoic acid (PAP)], o-carboxybenzamidoperoxycaproic acid, N-nonenylamidoperadipic acid and N-nonenylamidopersuccinates and (c) aliphatic and araliphatic peroxydicarboxylic acids, such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyl-di(6-aminopercaproic acid).

Other suitable bleaching agents in dishwashing detergents are chlorine- and bromine-releasing substances. Suitable chlorine- or bromine-releasing materials are, for example, heterocyclic N-bromamides and N-chloramides, for example trichloroisocyanuric acid, tribromoisocyanuric acid, dibromoisocyanuric acid and/or dichloroisocyanuric acid (DICA) and/or salts thereof with cations, such as potassium and sodium. Hydantoin compounds, such as 1,3-dichloro-5,5-dimethyl hydantoin, are also suitable.

In order to obtain an improved bleaching effect where washing is carried out at temperatures of 60° C. or lower, bleach activators may be incorporated in detergents according to the invention. The bleach activators may be compounds which form aliphatic peroxocarboxylic acids containing preferably 1 to 10 carbon atoms and more preferably 2 to 4 carbon atoms and/or optionally substituted perbenzoic acid under perhydrolysis conditions. Substances bearing O- and/or N-acyl groups with the number of carbon atoms mentioned and/or optionally substituted benzoyl groups are suitable. Preferred bleach activators are polyacylated alkylenediamines, more particularly tetraacetyl ethylenediamine (TAED), acylated triazine derivatives, more particularly 1,5-diacetyl-2,4-dioxohexahydro-1,3,5-triazine (DADHT), acylated glycolurils, more particularly tetraacetyl glycoluril (TAGU), N-acylimides, more particularly N-nonanoyl succinimide (NOSI), acylated phenol sulfonates, more particularly n-nonanoyl or isononanoyloxybenzenesulfonate (n- or iso-NOBS), carboxylic anhydrides, more particularly phthalic anhydride, acylated polyhydric alcohols, more particularly triacetin, ethylene glycol diacetate and 2,5-diacetoxy-2,5-dihydrofuran.

In addition to or instead of the conventional bleach activators mentioned above, so-called bleach catalysts may also be present. Bleach catalysts are bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and cobalt-, iron-, copper- and ruthenium-ammine complexes may also be used as bleach catalysts.

Suitable enzymes are those from the class of proteases, lipases, amylases, cellulases or mixtures thereof. Enzymes obtained from bacterial strains or fungi, such as *Bacillus subtilis, Bacillus licheniformis* and *Streptomyces griseus*, are particularly suitable. Proteases of the subtilisin type are preferred, proteases obtained from *Bacillus lentus* being particularly preferred. Enzyme mixtures, for example of protease and amylase or protease and lipase or protease and cellulase or of cellulase and lipase or of protease, amylase and lipase or of protease, lipase and cellulase, but especially cellulase-containing mixtures, are of particular interest. Peroxidases or oxidases have also proved to be suitable in some cases. The enzymes may be adsorbed to supports and/or encapsulated in membrane materials to protect them against premature decomposition. The percentage content of enzymes, enzyme mixtures or enzyme granules in the tablets according to the invention may be, for example, from about 0.1 to 5% by weight and is preferably from 0.1 to about 2% by weight. The most commonly used enzymes include lipases, amylases, cellulases and proteases. Preferred proteases are, for example BLAP® 140 (Biozym), Optimase®-M-440 and Opticlean®-M-250 (Solvay Enzymes); Maxacal® CX and Maxapem® or Esperase® (Gist Brocades) or even Savinase® (Novo). Particularly suitable cellulases and lipases are Celluzym® 0.7 T and Lipolase® 30 T (Novo Nordisk) while particularly suitable amylases are Duramyl® and Termamyl® 60 T and Termamyl® 90 T (Novo), Amylase-LT® (Solvay Enzymes) or Maxamyl® P5000 (Gist Brocades). Other enzymes may also be used.

In addition, the detergents according to the invention may also contain components with a positive effect on the removability of oil and fats from textiles by washing (so-called soil repellents). This effect becomes particularly clear when a textile which has already been repeatedly washed with a detergent according to the invention containing this oil- and fat-dissolving component is soiled. Preferred oil- and fat-dissolving components include, for example, nonionic cellulose ethers, such as methyl cellulose and methyl hydroxypropyl cellulose containing 15 to 30% by weight of methoxyl groups and 1 to 15% by weight of hydroxypropoxyl groups, based on the nonionic cellulose ether, and the polymers of phthalic acid and/or terephthalic acid known from the prior art or derivatives thereof, more particularly polymers of ethylene terephthalates and/or polyethylene glycol terephthalates or anionically and/or nonionically modified derivatives thereof. Of these, the sulfonated derivatives of phthalic acid and terephthalic acid polymers are particularly preferred.

The detergents may contain derivatives of diaminostilbenedisulfonic acid or alkali metal salts thereof as optical brighteners. Suitable optical brighteners are, for example, salts of 4,4'-bis-(2-anilino-4-morpholino-1,3,5-triazinyl-6-amino)-stilbene-2,2'-disulfonic acid or compounds of similar composition which contain a diethanolamino group, a methylamino group, an anilino group or a 2-methoxyethylamino group instead of the morpholino group. Brighteners of the substituted diphenyl styryl type, for example alkali metal salts of 4,4'-bis-(2-sulfostyryl)-diphenyl, 4,4'-bis-(4-chloro-3-sulfostyryl)-diphenyl or 4-(4-chlorostyryl)-4'-(2-sulfostyryl)-diphenyl, may also be present. Mixtures of the brighteners mentioned above may also be used.

In order to improve their aesthetic impression, the detergents according to the invention may be colored with suitable dyes. Preferred dyes, which are not difficult for the expert to choose, have high stability in storage, are not affected by the other ingredients of the detergents or by light and do not have any pronounced substantivity for textile fibers so as not to color them.

Dishwashing detergents according to the invention may contain corrosion inhibitors to protect the tableware or the machine itself, silver protectors being particularly important for dishwashing machines. Above all, silver protectors selected from the group of triazoles, benzotriazoles, bisbenzotriazoles, aminotriazoles, alkylaminotriazoles and the transition metal salts or complexes may generally be used.

Benzotriazole and/or alkylaminotriazole is/are particularly preferred. In addition, dishwashing formulations often contain corrosion inhibitors containing active chlorine which are capable of distinctly reducing the corrosion of silver surfaces. Chlorine-free dishwashing detergents contain in particular oxygen- and nitrogen-containing organic redox-active compounds, such as dihydric and trihydric phenols, for example hydroquinone, pyrocatechol, hydroxyhydroquinone, gallic acid, phloroglucinol, pyrogallol and derivatives of these compounds. Salt-like and complex-like inorganic compounds, such as salts of the metals Mn, Ti, Zr, Hf, V, Co and Ce are also frequently used. Of these, the transition metal salts selected from the group of manganese and/or cobalt salts and/or complexes are preferred, cobalt (ammine) complexes, cobalt(acetate) complexes, cobalt(carbonyl) complexes, chlorides of cobalt or manganese and manganese sulfate being particularly preferred. Zinc compounds may also be used to prevent corrosion of tableware.

Particular ingredients which may be used in compositions according to the invention for machine dishwashing or for cleaning hard surfaces are substances which prevent the re-soiling of surfaces and/or facilitate the removal of soil after a single application ("soil release compounds").

Suitable soil release compounds are any of the compounds known in the prior art. Particularly suitable are cationic polymers such as, for example, hydroxypropyl trimethylammonium guar, copolymers of aminoethyl methacrylate and acrylamide and copolymers of dimethyl diallyl ammonium chloride and acrylamide, polymers containing imino groups, cationic cellulose derivatives, cationic homo- and/or copolymers (monomer units; quaternized ammonium alkyl methacrylate groups).

Particularly preferred soil release compounds are cationic polymers selected from cationic polymers of copolymers of such monomers as trialkyl ammonium alkyl (meth)acrylate or acrylamide; dialkyl diallyl diammonium salts; polymer-analog reaction products of ethers or esters of polysaccharides containing lateral ammonium groups, more particularly guar, cellulose and starch derivatives; polyadducts of ethylene oxide with ammonium groups; quaternary ethyleneimine polymers and polyesters and polyamides containing quaternary side groups. Natural polyuronic acids and related substances, polyampholytes and hydrophobicized polyampholytes and mixtures of these substances are also very much preferred for the purposes of the present invention.

This list of ingredients of detergent/cleaning compositions is by no means complete but merely represents the most important typical ingredients of such compositions. More particularly, the compositions may also contain organic solvents where they are formulated as liquids or gels. The organic solvents used are preferably mono- or polyhydric $C_{1-4}$ alcohols. Preferred alcohols in such compositions are ethanol, 1,2-propanediol, glycerol and mixtures of these alcohols. In preferred embodiments, the compositions contain 2 to 12% by weight of such alcohols.

Basically, the compositions may assume various aggregate states. In a preferred embodiment, the detergent/cleaning compositions are liquid or gel-form compositions, more particularly liquid laundry detergents or liquid dishwashing detergents or cleaning gels including in particular gel-form cleaners for flush toilets.

Gel-form cleaners for flush toilets are described, for example, in German patent application DE-A-197 158 72. These cleaners are preferably gel-form, pseudoplastic cleaners with a viscosity of 30,000 to 150,000 mPas which contain a polysaccharide as the gel-forming component, a $C_{8-10}$ alkyl polyglycoside or $C_{12-14}$ alkyl polyglycoside as emulsifier and wetting component and perfume oil. Fatty alcohol ether sulfates (FAEOS) and fatty alcohol sulfates (FAS) may be present as co-surfactants. The APG:co-surfactant ratio is generally greater than 1, preferably between 50:1 and 1:1, more preferably between 10:1 and 1.5:1 and most preferably between 5:1 and 1.8:1. The cleaners in question are, more particularly, stable, gel-form, shear-diluting cleaners containing polysaccharide, a surfactant system and perfume components, characterized in that they contain a polysaccharide, preferably a xanthan gum, in quantities of 1 to 5% by weight, preferably 1 to 4% by weight, more preferably 1.5 to 3.5% by weight and most preferably 1.8 to 3% by weight, a $C_{8-22}$ alkyl polyglycoside in quantities of 3 to 25% by weight, preferably 4 to 20% by weight, more preferably 5 to 15% by weight and most preferably 5 to 12% by weight as one component of the surfactant system and the perfume component(s) in quantities of up to 15% by weight, preferably 2 to 12% by weight and more preferably 3 to 8% by weight and optionally other ingredients, such lime-dissolving agents, dyes, germ inhibitors, pearlizers, stabilizers, cleaning boosters and odor absorbers, the compositions having a viscosity of 30,000 to 150,000 mPas, as measured with a Brookfield Helipath RVT rotational viscosimeter with a TA spindle at 1 r.p.m./23° C.

Cleaning gels of the type in question are normally accommodated in containers designed to be placed in a lavatory bowl or in cisterns. A special container, which is particularly suitable for the gel-form cleaning compositions, is described in German patent application DE-A-195 201 45.

It has been found that visually attractive, translucent or clear pseudoplastic gel structures, which are as stable as solid rim blocks in suitable containers, can be obtained with polysaccharides in the described combinations, depending on the types selected with high perfume and APG concentrations.

Other standard gel formers such as, for example, polyacrylic acid (Carbopol), surfactant-thickened systems, MHPC (Natrosol) or sodium-chloride- or electrolyte-thickened surfactant systems do not show adequate gel stability where the high surfactant and perfume levels required are used and accordingly are less preferred. These formulations are often not sufficiently pseudoplastic, are diluted by water flowing over them and, on account of their inadequate viscosity behavior, drip uncontrollably into the lavatory bowl despite suitable containers. By contrast, the formulations according to the invention are decidedly pseudoplastic and withstand the water flowing over them to the extent that only small amounts are released and the required stability is obtained. This is because the compositions should also not dissolve too readily in the water penetrating into their containers, otherwise they would be dissolved and therefore exhausted after only a small number of flushes.

A particularly preferred embodiment is characterized in that, under certain conditions in the production process, air bubbles are introduced into the compositions according to the invention and retain their shape and size over a period of several weeks so that the end product becomes even more attractive to the consumer.

The size of the air bubbles, which can be controlled for example through the stirring rate in the production process and through the viscosity of the compositions, should be neither too large nor too small. In addition, the quantity of air bubbles should only be selected in a preferred range. If, therefore, the presence of air bubbles should be desirable, no more than 30% volume of air should be present, air volumes of 2 to 25% by volume being preferred and air volumes of 5 to 20% by volume being particularly preferred. Particularly preferred embodiments contain air bubbles between 0.1 mm and 20 mm in diameter, air bubbles between 1 mm and 15 mm diameter being most particularly preferred.

However, the viscosity of the preferred compositions also enables the air bubbles already introduced in the production process to be removed by brief application of a reduced pressure which may be in a range just below ambient pressure to approaching a vacuum. The duration of the reduced pressure treatment will depend on the strength of the reduced pressure. If a relatively strong reduced pressure is applied, the treatment need not be continued for very long. However, the expert also knows that an excessive reduced pressure can result in unwanted side effects including, for example, the intensified evaporation of readily volatile perfume components and, in some cases, problems affecting the stirrability of the system. Although the compositions according to the invention can be degassed by treatment in a centrifuge or by ultrarapid stirring, such treatments are not preferred.

The formulations according to the invention may be produced in various ways and in various batch sizes up to, and including, several tonnes. Normally, water is introduced into a commercially available mixer, for example a Beco-Mix, and the dye is stirred in. The xanthan gum used is separately suspended with solvent, preferably ethanol, and the required perfume oil. The suspension is then added and the whole is stirred at low speed, for example at 30 r.p.m. Investigations have shown that, after all the components have been added, a time of a few minutes to a few hours is required to reach the consistency according to the invention. In the present case, the surfactant (alkyl polyglycoside) was slowly added after 30 minutes. The other components are then added. If a bubble-free gel is to be guaranteed, the mixture has to be placed under a reduced pressure or under a vacuum, as described above, in a suitable container in dependence upon its viscosity, but generally for a short time, for example 15 minutes.

However, other procedures may be adopted. This is advisable, for example, where disinfectants are to be included. In this case, water is normally introduced into a commercially available mixer, for example a Beco-Mix, and the xanthan gum used is then stirred in. The suspension is then added and the whole is stirred at low speed, for example at 30 r.p.m., before the surfactant mixture (alkyl polyglycol/ fatty alcohol ether sulfate) is slowly added after 30 minutes. The dye is then added before a solution of the perfume in ethanol is introduced.

The disinfectant, preferably selected from the group of isothiazolines, benzoates or salicylic acid or salicylates, is added next. In this case, the composition can be packed in commercially available measuring bottles, for example in a rotary bottle filling machine.

Particular care has to be taken when substances are added to the prepared and swollen water-containing xanthan gel to allow the structure according to the invention to form. If these substances are added too quickly, phase separation problems can arise. In addition, no surfactant should be present during the preparation of the xanthan gel component because it would prevent gel formation. Accordingly, it is very much preferred to add the surfactant components after formation of the gel.

Viscosity may be measured by any of the methods normally used. Brookfield viscosimeters which have a spindle specially designed for gels were used in the present case. The viscosities according to the invention were measured with this Helipath spindle.

In one basic formulation, the preferred gel formulations may contain the following components:
  1.0–5.0% by weight of polysaccharide
  3.0–25.0% by weight of $C_{8-22}$ alkyl polyglycoside
  0–15.0% by weight of co-surfactants (FAS, FAEOS)
  0–5.0% by weight of citric acid
  0–5.0% by weight of complexing agent
  up to 15% by weight, preferably 2.0 to 12.0% by weight of perfume
  up to 5.0% by weight and preferably from 0.01 to 4% by weight of solvent, for example ethanol
  0–1.0% by weight of preservative
  0–10.0% by weight of dye
  0–5.0% by weight and preferably 0.01 to 3% by weight of germ inhibitor.

In the context of the present invention, a polysaccharide is understood, for example, to be a xanthan gum or a guar gum or a mixture of polysaccharides. Xanthan is formed from a chain with β-1,4-linked glucose (cellulose) with side chains. The structure of the sub-groups consists of glucose, mannose, glucuronic acid, acetate and pyruvate. Xanthan is produced by Xanthonomas campestris under aerobic conditions with a molecular weight of $2-15\times10^6$. Xanthan is produced inter alia in bath cultures and, after destruction of the culture and precipitation with propanol, is dried and ground. Other suitable methods are also described in the literature.

Alkyl polyglycosides are surfactants which may be obtained by reacting sugars and alcohols using the relevant methods of preparative organic chemistry. A mixture of monoalkylated, oligomeric or polymeric sugars is obtained according to the particular method of production used. Preferred alkyl polyglycosides are alkyl polyglucosides. In a particularly preferred embodiment, the alcohol is a long-chain fatty alcohol with alkyl chain lengths of $C_8$ to $C_{22}$, preferably from $C_8$ to $C_{16}$ and more preferably from $C_8$ to $C_{12}$ or a mixture of long-chain fatty alcohols. The degree of oligomerization of the sugars which is a calculated quantity, i.e. is generally not a whole number, is between 1 and 10, preferably between 1.1 and 5, more preferably between 1.2 and 3 and most preferably between 1.3 and 2.5.

According to the invention, anionic co-surfactants include aliphatic sulfates, such as fatty alcohol sulfates, fatty alcohol ether sulfates, dialkyl ether sulfates, monoglyceride sulfates, and aliphatic sulfonates, such as alkane sulfonates, olefin sulfonates, ether sulfonates, n-alkyl ether sulfonates, ester sulfonates and lignin sulfonates. Other anionic co-surfactants which may be used in accordance with the invention, but are not preferred, include fatty acid cyanamides, sulfosuccinic acid esters, fatty acid isethionates, acylaminoalkane sulfonates (fatty acid taurides), fatty acid sarcosinates, ether carboxylic acids and alkyl (ether)phosphates. Fatty alcohol sulfates and fatty alcohol ether sulfates are preferably used. Hitherto, less favorable results were obtained with alkyl benzenesulfonates.

However, nonionic co-surfactants may also be used. Nonionic surfactants in the context of the present invention include alkoxylated alcohols, such as polyglycol ethers, fatty alcohol polyglycol ethers, alkylphenol polyglycol ethers, end-capped polyglycol ethers, mixed ethers and hydroxy mixed ethers and fatty acid polyglycol esters. Ethylene oxide, propylene oxide, block polymers and fatty acid alkanolamides and fatty acid polyglycol ethers may also be used.

Alkoxylated alcohols are generally understood to be the reaction products of alkylene oxide, preferably ethylene oxide, with alcohols, preferably relatively long-chain alcohols. Depending on the reaction conditions, a complex mixture of addition products with different degrees of ethoxylation is generally formed from n mol of ethylene oxide and 1 mol of alcohol. Another embodiment is characterized by the use of mixtures of alkylene oxides, preferably a mixture of ethylene oxide and propylene oxide. If desired, "capped" alcohol ethoxylates, which may also be used for the purposes of the invention, can also be obtained by etherification with short-chain alkyl groups, preferably butyl groups, in a concluding step. According to the invention, highly ethoxylated fatty alcohols or mixtures thereof with end-capped fatty alcohol ethoxylates are most particularly preferred.

The formulations may advantageously contain lime-dissolving acids, such as citric acid, acetic acid, lactic acid or water-soluble salts thereof, in a quantity of 1 to 12%. Contents of 2 to 5% by weight are particularly preferred.

The gels preferably contain dye either for coloring the product or for coloring the liquid circulating around the container. In a preferred embodiment, the content of water-soluble dyes is below 1% by weight and is intended to improve the appearance of the product. If an additional color signal is required during flushing, the content of water-soluble dyes may be increased to 5% by weight.

Although the gels according to the invention already have an excellent cleaning effect without this component, the hygienic effect can be enhanced by the addition of germ inhibitors. The quantity of germ inhibitor used is governed to a large extent by the effectiveness of the particular compound and may be as much as 5% by weight. A quantity of more than 0.01% by weight is preferably incorporated in the gels, quantities of 0.01% by weight to 3% by weight being particularly preferred. Isothiazoline mixtures, sodium benzoate or salicylic acid are particularly suitable.

The perfume oils, which may be present in preferred gels in quantities of up to 15% by weight, preferably 2 to 12% by weight and more particularly 3 to 8% by weight, include the compounds described in the foregoing. According to the invention, these perfume oils contain the described silicic acid esters. The perfume oil may consist entirely of such silicic acid esters or may contain silicic acid esters in admixture with other perfumes.

Suitable solubilizers, for example for dyes and perfume oils, include for example alkanolamines, polyols, such as ethylene glycol, propylene glycol, glycerol and other monohydric and polyhydric alcohols and also alkyl benzenesulfonates with 1 to 3 carbon atoms in the alkyl moiety. The group of lower alcohols is particularly preferred, ethanol being most particularly preferred.

Conventional thickeners, which could also be used if required, include urea, sodium chloride, sodium sulfate, magnesium sulfate, ammonium chloride and magnesium chloride and combinations thereof. However, the use of these additional thickeners is not preferred.

The gels according to the invention may optionally contain water-soluble and water-insoluble builders. Water-soluble builders are preferred because they are generally not as prone to form insoluble residues on hard surfaces. Conventional builders or complexing agents which may be present in accordance with the invention include low molecular weight polycarboxylic acids and salts thereof, homopolymeric and copolymeric polycarboxylic acids and salts thereof, citric acid and salts thereof, carbonates, phosphates and silicates. Water-insoluble builders include zeolites, which may also be used, and mixtures of the builders mentioned above. The group of citrates is particularly preferred.

Other typical cleaners which may contain the silicic acid esters according to the invention are liquid or gel-form cleaners for hard surfaces, more particularly so-called multipurpose cleaners, glass cleaners, floor and bathroom cleaners and special embodiments of such cleaners, including acidic and alkaline forms of multipurpose cleaners and glass cleaners with a so-called anti-rain effect. These liquid cleaners may be present in one or more phases. In a particularly preferred embodiment, the cleaners have two different phases.

Cleaners in the broadest sense are—generally surfactant-containing—formulations with a very wide range of applications and, dependent thereon, very different compositions. The most important market segments are domestic cleaners, industrial (technical) and institutional cleaners. Cleaners are divided into alkaline, neutral and acidic types according to their pH and into liquid and solid cleaners (including tablets) according to their supply form. In contrast for example to dishwashing detergents, which also belong to the product group of cleaners, so-called hard surface cleaners are intended to show an optimal performance profile both in concentrated form and after dilution with water in conjunction with mechanical energy. Cold cleaners develop their effect without elevated temperature. The cleaning effect is critically determined above all by surfactants and/or alkali carriers or acids and, optionally, even solvents, such as glycolethers and lower alcohols. In general, the formulations also contain builders and, depending on the type of cleaner, bleaching agents, enzymes, germ-reducing or disinfecting additives and perfume oils and dyes. Cleaners may also be formulated as microemulsions. The cleaning result depends to a large extent on the type of soil, which is also geographically very different, and on the properties of the surfaces to be cleaned.

Household cleaners may be formulated as universal cleaners or as special cleaners for inter alia ceramics, tiles, windows, plastics, carpets, cookers, ovens, microwave ovens, as sanitary cleaners or lavatory cleaners. Pipe cleaners are alkalized and consist, for example, of solid sodium hydroxide and aluminium powder which, on dissolving, provides the hydrogen for creating the necessary turbulence in the pipe segments to be unblocked. Besides surfactant and builder, sanitary cleaners contain above all germ-reducing active ingredients, the sodium hypochlorite previously used being partly replaced by hydrogen peroxide or other peroxygen compounds. Lavatory cleaners are mainly acidic, occasionally even alkaline. In the former case, the phosphoric acid originally used and the sodium hydrogen sulfate are largely replaced by organic acids, above all citric acid. Speciality cleaners in the DIY sector include car cleaners, windscreen cleaners, rim cleaners, engine cleaners and paint applicator cleaners.

Institutional cleaners are used for operational cleaning and hygiene, for example in schools, offices, hotels, guesthouses and hospitals. In the last case, safe surface disinfection is a particular requirement the products are expected to satisfy. Institutional cleaners are available in large containers (large consumer products). The products and associated services using specially developed cleaning equipment are marketed as system solutions.

Industrial cleaners are used above all in the beverage, food, cosmetic and pharmaceutical industries and also in the metal industry for degreasing. The product group also includes cleaners for car washes, tanker and aircraft cleaners. In view of the necessary productivity, for example in bottle washing, these cleaners have to be formulated with low-foam surfactants, for which purpose special nonionic surfactants, such as ethylene, oxide/propylene oxide block copolymers and so-called end-capped alkyl ethoxylates are suitable.

A preferred multiphase multipurpose cleaner is a water-containing, liquid, multiphase, surfactant-containing cleaner with at least two continuous phases which comprises at least one lower aqueous phase I and an upper aqueous phase II immiscible with phase I, which can be temporarily converted into an emulsion by shaking and which contains 0 to 5% by weight of sodium hexametaphosphate. The sodium hexametaphosphate is a mixture of condensed orthophosphates, the degree of condensation being on average about 12.

One such cleaner is described in earlier German patent application DE-A-198 11 386. According to the invention, this cleaner contains perfumes, the perfume oils present being at least partly present in the form of the silicic acid esters according to the invention.

In the most simple case, the cleaner in question comprises a lower continuous phase consisting of the entire phase I and an upper continuous phase consisting of the entire phase II. However, one or more continuous phases of the cleaner may also contain parts of another phase in emulsified form, so that in a cleaner such as this part of phase I for example is present as continuous phase I, which represents the lower continuous phase of the cleaner, while another part is emulsified as discontinuous phase I in the upper continuous phase II. The same applies to phase II and other continuous phases.

Temporary means that 90% of the separation of the emulsion formed by shaking into the separate phases takes place over a period of 2 minutes to 10 hours at temperatures of about 20° C. to about 40° C., the remaining 2% of the separation into the phase state before shaking taking place over another 15 minutes to 50 hours.

The cleaners in question are distinguished by an unusually high cleaning performance against obstinate fatty soils in undiluted form. In addition, they show favorable residue behavior. The individual phases in the cleaner remain stable for long periods without forming deposits, for example, and the conversion into a temporary emulsion remains reversible even after frequent shaking. In addition, the separation of ingredients into separate phases can promote the chemical stability of the cleaner.

In one preferred embodiment of the invention, continuous phases I and II are separated from one another by a clearly defined phase boundary.

In another preferred embodiment of the invention, one or both of the continuous phases I and II contain(s) parts, preferably 0.1 to 25% by volume and more preferably 0.2 to 15% by volume, based on the volume of the particular continuous phase, of the other phase as dispersant. In this embodiment, the continuous phase I or II is reduced by that part by volume which is distributed as dispersant in the other phase. Particularly preferred compositions are those in which phase I is emulsified into phase II in quantities of 0.1 to 25% by volume and preferably in quantities of 0.2 to 15% by volume, based on the volume of phase II.

In another preferred embodiment of the invention, part of the two phases—in addition to the continuous phases I and II—is present as an emulsion of one of the two phases in the other phase, this emulsion being separated from those parts of phases I and II which are not involved in the emulsion by two clearly defined phase boundaries, namely an upper and a lower phase boundary.

In a particularly advantageous embodiment, the cleaners contain one or more hydrophobic components. Suitable hydrophobic components are, for example, dialkyl ethers with like or different $C_{4-14}$ alkyl groups, more particularly dioctyl ethers; hydrocarbons with a boiling range of 100 to 300° C., more particularly 140 to 280° C., for example aliphatic hydrocarbons with a boiling range of 145 to 200° C., isoparaffins with a boiling range of 200 to 260° C.; essential oils, more particularly limonene and the pine oil extracted from pine roots and stubs; and also mixtures of these hydrophobic components, more particularly mixtures of two or three of the hydrophobic components mentioned. Preferred mixtures of hydrophobic components are mixtures of various dialkyl ethers, of dialkyl ethers and hydrocarbons, of dialkyl ethers and essential oils, of hydrocarbons and essential oils, of dialkyl ethers and hydrocarbons and essential oils and of these mixtures. The cleaners contain hydrophobic components in quantities, based on the composition, of 0 to 20% by weight, preferably 0.1 to 14% by weight, more preferably 0.5 to 14% by weight, most preferably 0.5 to 10% by weight and, in one particularly advantageous embodiment, 0.8 to 7% by weight.

The cleaners may additionally contain one or more phase separation auxiliaries. Suitable phase separation auxiliaries are, for example, alkali metal and alkaline earth metal chlorides and sulfates, more especially sodium and potassium chloride and sulfate, and ammonium chloride and sulfate and mixtures thereof. The salts mentioned, as strong electrolytes, assist phase separation through the salt effect. Builder salts as electrolytes have the same effect and accordingly are also suitable as phase separation auxiliaries. The cleaners contain phase separation auxiliaries in quantities, based on the composition, of 0 to 30% by weight, preferably 1 to 20% by weight, more preferably 3 to 15% by weight and most preferably 5 to 12% by weight.

The cleaners may contain anionic, nonionic, amphoteric or cationic surfactants or surfactant mixtures of one, several or all of these surfactant classes as their surfactant component. The cleaners contain surfactants in quantities, based on the composition, of 0.01 to 30% by weight, preferably 0.1 to 20% by weight, more preferably 1 to 14% by weight and most preferably 3 to 10% by weight.

Suitable nonionic surfactants in the multipurpose cleaners are, for example, $C_{8-18}$ alkyl alcohol polyglycol ethers, alkyl polyglycosides and nitrogen-containing surfactants and mixtures thereof, more especially mixtures of the first two. The cleaners contain nonionic surfactants in quantities, based on the composition, of 0 to 30% by weight, preferably 0.1 to 20% by weight, more preferably 0.5 to 14% by weight and most preferably 1 to 10% by weight.

$C_{8-18}$ alkyl alcohol polypropylene glycol/polyethylene glycol ethers are preferred known nonionic surfactants. They may be described by the formula $R^1O-(CH_2CH(CH_3)O)_p(CH_2CH_2O)_e-H$, in which $R^1$ is a linear or branched, aliphatic alkyl and/or alkenyl group containing 8 to 18 carbon atoms, p is 0 or a number of 1 to 3 and e is a number of 1 to 20. The $C_{8-18}$ alkyl alcohol polyglycol ethers may be obtained by addition of propylene oxide and/or ethylene oxide onto alkyl alcohols, preferably onto fatty alcohols. Typical examples are polyglycol ethers in which $R^1$ is an alkyl group containing 8 to 18 carbon atoms, p=0 to 2 and e is a number of 2 to 7. Preferred representatives are, for example $C_{10-14}$ fatty alcohol+1PO+6EO ether (p=1, e=6) and $C_{12-18}$ fatty alcohol+7EO ether (p=0, e=7) and mixtures thereof.

End-capped $C_{8-18}$ alkyl alcohol polyglycol ethers, i.e. compounds in which the free OH group is etherified, may also be used. The end-capped $C_{8-18}$ alkyl alcohol polyglycol ethers may be obtained by relevant methods of preparative organic chemistry. Preferably, $C_{8-18}$ alkyl alcohol polyglycol ethers are reacted with alkyl halides, more especially butyl or benzyl chloride, in the presence of bases. Typical examples are mixed ethers in which $R^1$ is a technical fatty alcohol moiety, preferably a $C_{12/14}$ cocoalkyl moiety, p=0 and e=5 to 10, which are end-capped with a butyl group.

Other preferred nonionic surfactants are the alkyl polyglycosides described in the foregoing.

Other suitable nonionic surfactants are nitrogen-containing surfactants, for example fatty acid polyhydroxyamides, for example glucamides, and ethoxylates of alkyl amines, vicinal diols and/or carboxylic acid amides containing alkyl groups with 10 to 22 carbon atoms and preferably 12 to 18 carbon atoms. The degree of ethoxylation of these compounds is generally between 1 and 20 and preferably between 3 and 10. Ethanolamide derivatives of alkanoic acids containing 8 to 22 carbon atoms and preferably 12 to 16 carbon atoms are preferred. Particularly suitable compounds include lauric acid, myristic acid and palmitic acid monoethanolamides.

Anionic surfactants suitable for multipurpose cleaners are $C_{8-18}$ alkyl sulfates, $C_{8-18}$ alkyl ether sulfates, i.e. the sulfation products of alcohol ethers, and/or $C_{8-18}$ alkyl benzenesulfonates and also $C_{8-18}$ alkanesulfonates, $C_{8-18}$-$\alpha$-olefin sulfonates, sulfonated $C_{8-18}$ fatty acids, more particularly dodecyl benzenesulfonate, $C_{8-22}$ carboxylic acid amide ether sulfates, sulfosuccinic acid mono- and di-$C_{1-12}$-alkyl esters, $C_{8-18}$ alkyl polyglycol ether carboxylates, $C_{8-18}$-N-acyl taurides, $C_{8-18}$-N-sarconsinates and $C_{8-18}$ alkyl isethionates and mixtures thereof. The anionic surfactants are used in the form of their alkali metal and alkaline earth metal salts, more especially sodium, potassium and magnesium salts, their ammonium and mono-, di-, tri- or tetraalkyl ammonium salts and—in the case of the sulfonates—also in the form of the corresponding acid, for example dodecyl benzene sulfonic acid. The cleaners contain anionic surfactants in quantities, based on the composition, of 0 to 30% by weight, preferably 0.1 to 20% by weight, more preferably 1 to 14% by weight and most preferably 2 to 10% by weight.

By virtue of their foam-suppressing properties, the compositions according to the invention may also contain soaps, i.e. alkali metal or ammonium salts of saturated or unsaturated $C_{6-22}$ fatty acids. The soaps may be used in a quantity of up to 5% by weight and preferably in a quantity of 0.1 to 2% by weight.

Suitable amphoteric surfactants are, for example, betaines corresponding to the formula $(R^{ii})(R^{iii})(R^{iv})N^+CH_2COO^-$, in which $R^{ii}$ is a $C_{8-25}$ and preferably $C_{10-21}$ alkyl group optionally interrupted by hetero atoms or hetero atom groups and $R^{iii}$ and $R^{iv}$ may be the same or different and represent alkyl groups containing 1 to 3 carbon atoms, more especially $C_{10-18}$ alkyl dimethyl carboxymethyl betaine and $C_{11-17}$ alkylamidopropyl dimethyl carboxymethyl betaine. The cleaners contain amphoteric surfactants in quantities, based on the composition, of 0 to 15% by weight, preferably 0.01 to 10% by weight and more preferably 0.1 to 5% by weight.

Suitable cationic surfactants are inter alia quaternary ammonium compounds with the formula $(R^v)(R^{vi})(R^{vii})(R^{viii})N^+ X^-$, in which $R^v$ to $R^{viii}$ stand for four identical or different, more especially two long-chain and two short-chain, alkyl groups and X) is an anion, more particularly a halide ion, for example didecyl dimethyl ammonium chloride, alkyl benzyl didecyl ammonium chloride and mixtures thereof. The compositions contain cationic surfactants in quantities, based on the composition, of 0 to 10% by weight, preferably 0.01 to 5% by weight and more preferably 0.1 to 3% by weight.

In another preferred embodiment, the cleaners contain anionic and nonionic surfactants together, preferably $C_{8-18}$ alkyl benzenesulfonates, $C_{8-18}$ alkyl sulfates and/or $C_{8-18}$ alkyl ether sulfates in conjunction with $C_{8-18}$ alkyl alcohol polyglycol ethers and/or alkyl polyglycosides, more particularly $C_{8-18}$ alkyl benzenesulfonates together with $C_{8-18}$ alkyl alcohol polyglycol ethers.

The cleaners according to the invention may also contain builders. Suitable builders are, for example, alkali metal gluconates, citrates, nitrilotriacetates, carbonates and bicarbonates, more especially sodium gluconate, citrate and nitrilotriacetate and sodium and potassium carbonate and bicarbonate, and alkali metal and alkaline earth metal hydroxides, more especially sodium and potassium hydroxide, ammonia and amines, more especially mono- and triethanolamine, and mixtures thereof. Other suitable builders are the salts of glutaric acid, succinic acid, adipic acid, tartaric acid and benzenehexacarboxylic acid and also phosphonates and phosphates. The cleaners contain builders in quantities, based on the composition, of 0 to 20% by weight, preferably 0.01 to 12% by weight, more preferably 0.1 to 8% by weight and most preferably 0.3 to 5% by weight, the quantity of sodium hexametaphosphate being limited to 0 to 5% by weight except in the cleaners used in accordance with the invention. As electrolytes, the builder salts also act as phase separation auxiliaries.

Besides the components mentioned, the cleaners according to the invention may contain other auxiliaries and additives of the type typically present in such compositions. These include in particular polymers, soil release agents, solvents (for example ethanol, isopropanol, glycol ether), solubilizers, hydrotropes (for example sodium cumenesulfonate, octyl sulfate, butyl glucoside, butyl glycol), cleaning boosters, viscosity adjusters (for example synthetic polymers, such as polysaccharides, polyacrylates, naturally occurring polymers and derivatives thereof, such as xanthan gum, other polysaccharides and/or gelatine), pH adjusters (for example citric acid, alkanolamines or NaOH), disinfectants, antistatic agents, preservatives, bleaching systems, enzymes, dyes and also opacifiers or even skin care agents as described in EP-A-0 522 556. The quantity in which such additives are present in the cleaning composition is normally not more than 12% by weight. The lower limit depends upon the nature of the auxiliary/additive and, in the case of dyes for example, may be at 0.001% by weight or lower. The auxiliaries/additives are preferably present in a quantity of 0.01 to 7% by weight and more preferably in a quantity of 0.1 to 4% by weight.

The pH value of the multipurpose cleaners may be varied over a broad range but is preferably in the range from 2.5 to 12 and more particularly in the range from 5 to 10.5. In the context of the invention, the pH value is understood to be the pH value of the cleaner in the form of the temporary emulsion.

Multipurpose cleaners of the type in question can be modified for any purposes. One particular embodiment are glass cleaners. A key aspect of glass cleaners is that stains or edges should not be left behind. A particular problem is that, after cleaning, water condenses on the cleaned surfaces and leads to the so-called film effect. It is equally undesirable for so-called rain marks to be left behind on glass surfaces exposed to rain. This effect is known as the rain effect or anti-rain effect. These effects can be prevented by suitable additives in glass cleaners.

WO-A-96/04358 describes cleaning compositions which are capable of cleaning glass without leaving behind any troublesome stains and/or films and which contain an effective quantity of a substantive polymer containing hydrophilic groups which provides the glass with relatively high and long-lasting hydrophilia, so that, the next three times at least the glass is wetted, for example by rain, the water drains from the glass surface and few stains are left behind after drying. Substantive polymers are, in particular, polycarboxylates, such as poly(vinyl pyrrolidone-co-acrylic acid), but also poly(styrene sulfonate), cationic sugar and starch derivatives and block copolymers of ethylene oxide and propylene oxide, the latter polyethers in particular having relatively little substantivity.

WO 94/22800 describes epoxy-end-capped polyalkoxylated alcohols corresponding to formula VII:

$$R^{I}O[CH_2CH(CH)_3O]_x[CH_2CH_2O]_y[CH_2CH(R^{II})O]_zH \qquad (VII)$$

in which $R^{I}$ is a linear aliphatic hydrocarbon radical containing about 4 to about 18 carbon atoms or a mixture of various such radicals, $R^{II}$ is a linear, aliphatic hydrocarbon radical containing about 2 to about 26 carbon atoms or a mixture of various such radicals, x is a number of 1 to about 3, y is a number of 5 to about 30 and z is a number of 1 to about 3.

The alcohols corresponding to formula VII may be incorporated in powder-form and liquid dishwasher detergents or cleaning compositions for hard surfaces. In dishwasher detergents, they reduce stain and film formation.

WO 96/12001 describes epoxy-end-capped polyalkoxylated alcohols corresponding to formula VIII:

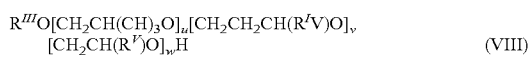
$$R^{III}O[CH_2CH(CH)_3O]_u[CH_2CH_2CH(R^{V})O]_v[CH_2CH(R^{V})O]_wH \qquad (VIII)$$

in which $R^{III}$ is a linear aliphatic hydrocarbon radical containing about 4 to about 18 carbon atoms or a mixture of various such radicals, $R^{IV}$ is a hydrogen atom or a lower alkyl group containing 1 to 6 carbon atoms, $R^{V}$ is a linear aliphatic hydrocarbon radical containing about 2 to about 14 carbon atoms or a mixture of various such radicals, u is a number of 1 to about 5, v is a number of 1 to about 30 and w is a number of 1 to about 3.

The alcohols corresponding to formula VIII may be incorporated individually or together with alcohols corresponding to formula VII in powder-form and liquid dishwasher detergents or cleaning compositions for hard surfaces, such as bathroom tiles. In dishwasher detergents, they reduce stain and film formation.

In one particular embodiment, the end-capped polyalkoxylated alcohols described in DE-A-198 56 529 which correspond to formulae IX and X:

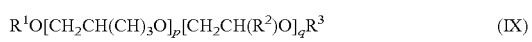
$$R^{1}O[CH_2CH(CH)_3O]_p[CH_2CH(R^2)O]_qR^3 \qquad (IX)$$

where $R^1$ is a linear aliphatic hydrocarbon radical containing 1 to about 22 carbon atoms or a mixture of various such radicals, $R^2$ is a hydrogen atom or a lower alkyl group containing 1 to 6 carbon atoms, $R^3$ is a linear or branched, saturated or unsaturated, aliphatic, optionally aryl-substituted, acyclic or cyclic hydrocarbon radical containing 1 to about 78 carbon atoms and optionally one or more hydroxy groups and/or ether groups —O— or a mixture of various such radicals, p is a number of 0 to about 15 and q is a number of 0 to about 50, the sum of p and q being at least 1, are used in a composition for cleaning hard surfaces to reduce the rain effect and/or the film effect.

The content of one or more end-capped polyalkoxylated alcohols corresponding to formulae IX and X in the glass cleaner is from 0.001 to 20% by weight, preferably from 0.01 to 10% by weight, more preferably from 0.05 to 5% by weight, most preferably from 0.1 to 2.5% by weight and, in one particularly advantageous embodiment, from 0.2 to 2.0% by weight.

Examples of the end-capped polyalkoxylated alcohols are those corresponding to formulae IX and X in which (a) $R^1=C_{12-18}$ or $C_{12/14}$ fatty alkyl group, $R^2=H$, $R^3=$butyl group, p=0, q=10, (b) $R^1=C_{12-18}$ fatty alkyl group, $R^2=H$, $R^3=$butyl group, p=0, q=5, (c) $R^1=CH_3$, $R^2=H$, $R^3=C_{12/14}$ fatty alkyl group, p=3, q=5 or (d) $R^1=C_8$ fatty alkyl group, $R^2=H$, $R^3=$butyl group, p=0, q=5.

Preferred end-capped polyalkoxylated alcohols are those corresponding to formulae IX and X, in which p and q are both at least 1 and/or $R^2$ is a hydrogen atom and/or $R^3$ represents at least one hydroxy group, more particularly in the α-position, i.e. $R^3$ is a group —CH_2CH(OH)—R. End-capped polyalkoxylated alcohols corresponding to formulae IX and X, in which $R^3$ is a group —CH_2CH(OH)—R, are known for example from DE 37 23 323.

Particularly preferred end-capped polyalkoxylated alcohols are epoxy-end-capped polyalkoxylated alcohols corresponding to formula IX and X, in which $R^1$ is a linear aliphatic hydrocarbon radical containing about 4 to about 18 and preferably about 4 to about 12 carbon atoms, more particularly a butyl, hexyl, octyl or decyl radical or mixtures thereof, or a mixture of various such radicals, $R^2$ is a hydrogen atom or a lower alkyl group containing 1 to 6 carbon atoms, preferably a hydrogen atom, $R^3$ is a group $[CH_2CH(R^4)O]_rH$, where $R^4$ is a linear aliphatic hydrocarbon radical containing about 2 to about 26, preferably about 4 to about 18 and more preferably about 6 to about 14 carbon atoms or a mixture of various such radicals and r is a number of 1 to about 3, preferably 1 to about 2, more preferably 1, p is a number of 1 to about 5, preferably 1 to about 2 and more preferably 1 and q is a number of 1 to about 30, preferably about 4 to about 26 and more preferably about 10 to about 24, for example with $R^1=C_{8/10}$ alkyl group, $R^2=H$, $R^3=[CH_2CH(R^4)O]_rH$ with $R^4=C_8$ alkyl group and r=1, u=1 and v=22.

Corresponding epoxy-end-capped polyalkoxylated alcohols and methods for their preparation are known, for example, from WO 94/22800 A1 and WO 96/12001 A1. Preferred end-capped alcohols are obtainable, for example, under the name of Dehypon® from Cognis GmbH or under the name of Poly Tergent® from Olin Corporation, for example Dehypon® LT 104, Dehypon® LS 104, Dehypon®

LT 54, Dehypon® LS 531 or Dehypon® O 54 and Poly Tergent® SLF 18 B48, Poly Tergent® SLF 18 B 45 or Poly Tergent® SL 62.

In another preferred embodiment, the detergent compositions are powder-form or granular compositions. The compositions according to the invention may have any bulk density. The range of possible bulk densities extends from low values below 600 g/l, for example 300 g/l, via medium-range values of 600 to 750 g/l to high values of at least 750 g/l. In a preferred variant of the high bulk density compositions according to the invention, however, the bulk density is even above 800 g/l, bulk densities above 850 g/l being particularly advantageous. With supercompactates such as these, the advantages of the soluble builder system are particularly relevant because corresponding compact compositions impose particular demands on their ingredients if they are to be dispersible. In addition, the low-dose builder system—irrespective of the bulk density—leads to additional advantages by saving on pack volume and reduces the chemicals introduced into the environment per wash cycle.

Compositions of the type in question may be produced by any methods known from the prior art.

They are preferably produced by mixing together various particulate components containing detergent ingredients which together make up at least 60% by weight of the detergent as a whole.

The particulate components may be produced by spray drying, simple mixing or complex granulation processes, for example fluidized-bed granulation. In one particularly preferred embodiment, at least one surfactant-containing component is produced by fluidized-bed granulation.

In another particularly preferred embodiment, aqueous preparations of the alkali metal silicate and alkali metal carbonate are sprayed in a dryer together with other detergent ingredients, drying optionally being accompanied by granulation.

The dryer into which the aqueous preparation is sprayed can be any type of dryer.

In one preferred embodiment of the process, drying is carried out by spray drying in a drying tower. In this case, the aqueous preparations are exposed in known manner to a stream of drying gas in fine-particle form. Applicants describe an embodiment of spray drying using superheated steam in a number of publications. The operating principle disclosed in those publications is hereby specifically included as part of the disclosure of the present invention. Reference is made in particular to the following publications: DE-A-40 30 688 and the further developments according to DE-A-42 04 035; DE-A-42 04 090; DE-A-42 06 050; DE-A42 06 521; DE-A-42 06 495; DE-A-42 08 773; DE-A-42 09 432 and DE-A-42 34 376.

In another preferred variant, particularly where detergents of high bulk density are to be obtained, the mixtures are subsequently subjected to a compacting step, other ingredients being added to the detergents after this compacting step.

In one preferred embodiment of the invention, the ingredients are compacted in a press agglomeration process. The press agglomeration process to which the solid premix (dried basic detergent) is subjected may be carried out in various agglomerators. Press agglomeration processes are classified according to the type of agglomerator used. The four most common press agglomeration processes—which are preferred to the purposes of the invention—are extrusion, roll compacting, pelleting and tabletting, so that preferred agglomeration processes for the purposes of the present invention are extrusion, roll compacting, pelleting and tabletting processes.

One feature common to all these processes is that the premix is compacted and plasticized under pressure and the individual particles are pressed against one another with a reduction in porosity and adhere to one another. In all the processes (but with certain limitations in the case of tabletting), the tools may be heated to relatively high temperatures or may be cooled to dissipate the heat generated by shear forces.

In all the processes, a binder may be used as a compacting auxiliary. In the interests of simplicity, the specification will hereinafter refer only to a binder or to the binder. However, it must be made clear at this juncture that, basically, several different binders and mixtures of various binders may also be used. A preferred embodiment of the invention is characterized by the use of a binder which is completely in the form of a melt at temperatures of only at most 130° C., preferably at most 100° C. and more preferably up to 90° C. In other words, the binder will be selected according to the process and the process conditions or, alternatively, the process conditions and, in particular, the process temperature will have to be adapted to the binder if it is desired to use a particular binder.

The actual compacting process is preferably carried out at processing temperatures which, at least in the compacting step, at least correspond to the temperature of the softening point if not to the temperature of the melting point of the binder. In one preferred embodiment of the invention, the process temperature is significantly above the melting point or above the temperature at which the binder is present as a melt. In a particularly preferred embodiment, however, the process temperature in the compacting step is no more than 20° C. above the melting temperature or the upper limit to the melting range of the binder. Although, technically, it is quite possible to adjust even higher temperatures, it has been found that a temperature difference in relation to the melting temperature or to the softening temperature of the binder of 20° C. is generally quite sufficient and even higher temperatures do not afford additional advantages. Accordingly it is particularly preferred, above all on energy grounds, to carry out the compacting step above, but as close as possible to, the melting point or rather to the upper temperature limit of the melting range of the binder. Controlling the temperature in this way has the further advantage that even heat-sensitive raw materials, for example peroxy bleaching agents, such as perborate and/or percarbonate, and also enzymes, can be processed increasingly without serious losses of active substance. The possibility of carefully controlling the temperature of the binder, particularly in the crucial compacting step, i.e. between mixing/homogenizing of the premix and shaping, enables the process to be carried out very favorably in terms of energy consumption and with no damaging effects on the heat-sensitive constituents of the premix because the premix is only briefly exposed to the relatively high temperatures. In preferred press agglomeration processes, the working tools of the press agglomerator (the screw(s) of the extruder, the roller(s) of the roll compactor and the pressure roller(s) the pellet press) have a temperature of at most 150° C., preferably of at most 100° C. and, in a particularly preferred embodiment, at most 75° C., the process temperature being 30° C. and, in a particularly preferred embodiment, at most 20° C. above the melting temperature or rather the upper temperature limit to the melting range of the binder. The heat exposure time in the compression zone of the press agglomerators is preferably at most 2 minutes and, more preferably, between 30 seconds and 1 minute.

Preferred binders which may be used either individually or in the form of mixtures with other binders are polyethylene glycols, 1,2-polypropylene glycols and modified polyethylene glycols and polypropylene glycols. The modified polyalkylene glycols include, in particular, the sulfates and/or the disulfates of polyethylene glycols or polypropylene glycols with a relative molecular weight of 600 to 12,000 and, more particularly, in the range from 1,000 to 4,000. Another group consists of mono- and/or disuccinates of polyalkylene glycols which, in turn, have relative molecular weights of 600 to 6,000 and, preferably, in the range from 1,000 to 4,000. A more detailed description of the modified polyalkylene glycol ethers can be found in the disclosure of International patent application WO-A-93/02176. In the context of the invention, polyethylene glycols include polymers which have been produced using $C_{3-5}$ glycols and also glycerol and mixtures thereof as starting molecules. In addition, they also include ethoxylated derivatives, such as trimethylol propane containing 5 to 30 EO. The polyethylene glycols preferably used may have a linear or branched structure, linear polyethylene glycols being particularly preferred. Particularly preferred polyethylene glycols include those having relative molecular weights in the range from 2,000 to 12,000 and, advantageously, around 4,000. Polyethylene glycols with relative molecular weights below 3,500 and above 5,000 in particular may be used in combination with polyethylene glycols having a relative molecular weight of around 4,000. More than 50% by weight of such combinations may advantageously contain polyethylene glycols with a relative molecular weight of 3,500 to 5,000, based on the total quantity of polyethylene glycols. However, polyethylene glycols which, basically, are present as liquids at room temperature/1 bar pressure, above all polyethylene glycol with a relative molecular weight of 200, 400 and 600, may also be used as binders. However, these basically liquid polyethylene glycols should only be used in the form of a mixture with at least one other binder, this mixture again having to satisfy the requirements according to the invention, i.e. must have a melting point or softening point at least above 45° C.

Other suitable binders are low molecular weight polyvinyl pyrrolidones and derivatives thereof with relative molecular weights of up to at most 30,000. Relative molecular weight ranges of 3,000 to 30,000, for example around 10,000, are preferred. Polyvinyl pyrrolidones are preferably not used as sole binder, but in combination with other binders, more particularly in combination with polyethylene glycols.

Other suitable binders are raw materials which, as raw materials, basically exhibit washing- or cleaning-active properties, i.e. for example nonionic surfactants with melting points of at least 45° C. or mixtures of nonionic surfactants and other binders. Preferred nonionic surfactants include alkoxylated fatty or oxoalcohols, more particularly $C_{12-18}$ alcohols. Degrees of alkoxylation, more particularly degrees of ethoxylation, of on average 18 to 80 AO, more particularly EO, per mol of alcohol and mixtures thereof have proved to be particularly advantageous. Above all, fatty alcohols containing on average 18 to 35 EO and, more particularly, an average of 20 to 25 EO show advantageous binder properties in the context of the present invention. Binder mixtures may also contain ethoxylated alcohols containing on average fewer EO units per mol of alcohol, for example tallow fatty alcohol containing 14 EO. However, these alcohols with a relatively low degree of ethoxylation are preferably used solely in admixture with alcohols having a relatively high degree of ethoxylation. The binders advantageously contain less than 50% by weight and, more particularly, less than 40% by weight, based on the total quantity of binder used, of alcohols with a relatively low degree of ethoxylation. Above all, nonionic surfactants typically used in detergents, such as $C_{12-18}$ alcohols containing on average 3 to 7 EO, which are basically liquid at room temperature, are preferably present in the binder mixtures in only such quantities that less than 2% by weight of these nonionic surfactants, based on the end product of the process, are available. As described above, however, it is by no means preferred to use nonionic surfactants liquid at room temperature in the binder mixtures. In one particularly advantageous embodiment, therefore, nonionic surfactants of the type in question do not form part of the binder mixture because not only do they reduce the softening point of the mixture, they can also contribute towards tackiness of the end product and, because of their tendency to gel on contact with water, often fail adequately to satisfy the requirement that the binder/partition in the end product should dissolve quickly. In addition, the binder mixture preferably does not contain the anionic surfactants typically encountered in detergents or their precursors, namely anionic surfactant acids. Other nonionic surfactants suitable as binders are the fatty acid methyl ester ethoxylates with no tendency to gel, more particularly those containing on average 10 to 25 EO (for a more detailed description of this group of substances, see below). Particularly preferred representatives of this group of substances are methyl esters based predominantly on $C_{16-18}$ fatty acids, for example hydrogenated beef tallow methyl ester containing on average 12 EO or 20 EO. One preferred embodiment of the invention is characterized by the use as binder of a mixture containing $C_{12-18}$ cocofatty alcohol or tallow fatty alcohol with on average 20 EO and polyethylene glycol with a relative molecular weight of 400 to 4,000. Another preferred embodiment of the invention is characterized by the use as binder of a mixture containing predominantly $C_{16-18}$-fatty-acid-based methyl ester with on average 10 to 25 EO, more particularly hydrogenated beef tallow methyl ester with on average 12 EO or 20 EO, and a $C_{12-18}$ cocofatty alcohol or tallow fatty alcohol with on average 20 EO and/or polyethylene glycol with a relative molecular weight of 400 to 4,000.

Binders based either solely on polyethylene glycols with a relative molecular weight of around 4,000 or on a mixture of $C_{12-18}$ cocofatty alcohol or tallow fatty alcohol with on average 20 EO and one of the above-described fatty acid methyl ester ethoxylates or on a mixture of $C_{12-18}$ cocofatty alcohol or tallow fatty alcohol with on average 20 EO, one of the above-described fatty acid methyl ester ethoxylates and a polyethylene glycol, more particularly with a relative molecular weight of around 4,000, have proved to be particularly advantageous embodiments of the invention.

Besides the substances mentioned here, other suitable substances may be present in the binder in small quantities.

Immediately after leaving the production unit, the compacted material preferably has temperatures of not more than 90° C., temperatures of 35 to 85° C. being particularly preferred. It has been found that exit temperatures—above all in the extrusion process—of 40 to 80° C., for example up to 70° C., are particularly advantageous.

In one preferred embodiment of the invention, the process according to the invention is carried out by extrusion as described, for example in European patent EP-B-0 486 592 or International patent applications WO 93/02176 and WO 94/09111 or WO 98/12299. In this extrusion process, a solid premix is extruded under pressure to form a strand and, after emerging from the multiple-bore extrusion die, the strands are cut into granules of predetermined size by means of a cutting unit. The solid, homogeneous premix contains a plasticizer and/or lubricant of which the effect is to soften the premix under the pressure applied or under the effect of specific energy, so that it can be extruded. Preferred plasticizers and/or lubricants are surfactants and/or polymers.

Particulars of the actual extrusion process can be found in the above-cited patents and patent applications to which reference is hereby expressly made. In one preferred embodiment of the invention, the premix is delivered, preferably continuously, to a planetary roll extruder or to a twin-screw extruder with co-rotating or contra-rotating screws, of which the barrel and the extrusion/granulation head can be heated to the predetermined extrusion temperature. Under the shear effect of the extruder screws, the premix is compacted under a pressure of preferably at least 25 bar or—with extremely high throughputs—even lower, depending on the apparatus used, plasticized, extruded in the form of fine strands through the multiple-bore extrusion die in the extruder head and, finally, size-reduced by means of a rotating cutting blade, preferably into substantially spherical or cylindrical granules. The bore diameter of the multiple-bore extrusion die and the length to which the strands are cut are adapted to the selected granule size. In this embodiment, granules are produced in a substantially uniformly predeterminable particle size, the absolute particle sizes being adaptable to the particular application envisaged. In general, particle diameters of up to at most 0.8 cm are preferred. Important embodiments provide for the production of uniform granules in the millimeter range, for example in the range from 0.5 to 5 mm and more particularly in the range from about 0.8 to 3 mm. In one important embodiment, the length-to-diameter ratio of the primary granules is in the range from about 1:1 to about 3:1. In another preferred embodiment, the still plastic primary granules are subjected to another shaping process step in which edges present on the crude extrudate are rounded off so that, ultimately, spherical or substantially spherical extrudate granules can be obtained. If desired, small quantities of drying powder, for example zeolite powder, such as zeolite NaA powder, can be used in this step. This shaping step may be carried out in commercially available spheronizing machines. It is important in this regard to ensure that only small quantities of fines are formed in this stage. According to the present invention, drying—which is described as a preferred embodiment in the prior art documents cited above—may be carried out in a subsequent step but is not absolutely essential. It may even be preferred not to carry out drying after the compacting step.

Alternatively, extrusion/compression steps may also be carried out in low-pressure extruders, in a Kahl press (manufacturer: Amandus Kahl) or in a so-called Bextruder (manufacturer: Bepex).

In one particularly preferred embodiment of the invention, the temperature prevailing in the transition section of the screw, the pre-distributor and the extrusion die is controlled in such a way that the melting temperature of the binder or rather the upper limit to the melting range of the binder is at least reached and preferably exceeded. The temperature exposure time in the compression section of the extruder is preferably less than 2 minutes and, more particularly, between 30 seconds and 1 minute.

In another preferred embodiment of the present invention, the process according to the invention is carried out by roll compacting. In this variant, the premix is introduced between two rollers—either smooth or provided with depressions of defined shape—and rolled under pressure between the two rollers to form a sheet-like compactate. The rollers exert a high linear pressure on the compound and may be additionally heated or cooled as required. Where smooth rollers are used, smooth untextured compactate sheets are obtained. By contrast, where textured rollers are used, correspondingly textured compactates, in which for example certain shapes can be imposed in advance on the subsequent detergent particles, can be produced. The sheet-like compactate is then broken up into smaller pieces by a chopping and size-reducing process and can thus be processed to granules which can be further refined and, more particularly, converted into a substantially spherical shape by further surface treatment processes known per se.

In roll compacting, too, the temperature of the pressing tools, i.e. the rollers, is preferably at most 150° C., more preferably at most 100° C. and most preferably at most 75° C. Particularly preferred production processes based on roll compacting are carried out at temperatures 10° C. and, in particular, at most 5° C. above the melting temperature of the binder or the upper temperature limit of the melting range of the binder. The temperature exposure time in the compression section of the rollers—either smooth or provided with depressions of defined shape—is preferably at most 2 minutes and, more particularly, between 30 seconds and 1 minute.

In another preferred embodiment of the present invention, the process according to the invention is carried out by pelleting. In this process, the premix is applied to a perforated surface and is forced through the perforations and at the same time plasticized by a pressure roller. In conventional pellet presses, the premix is compacted under pressure, plasticized, forced through a perforated surface in the form of fine strands by means of a rotating roller and, finally, is size-reduced to granules by a cutting unit. The pressure roller and the perforated die may assume many different forms. For example, flat perforated plates are used, as are concave or convex ring dies through which the material is pressed by one or more pressure rollers. In perforated-plate presses, the pressure rollers may also be conical in shape. In ring die presses, the dies and pressure rollers may rotate in the same direction or in opposite directions. A press suitable for carrying out the process according to the invention is described, for example, in DE-OS 38 16 842. The ring die press disclosed in this document consists of a rotating ring die permeated by pressure bores and at least one pressure roller operatively connected to the inner surface thereof which presses the material delivered to the die space through the pressure bores into a discharge unit. The ring die and pressure roller are designed to be driven in the same direction which reduces the shear load applied to the premix and hence the increase in temperature which it undergoes. However, the pelleting process may of course also be carried out with heatable or coolable rollers to enable the premix to be adjusted to a required temperature.

In pelleting, too, the temperature of the pressing tools, i.e. the pressure rollers, is preferably at most 150° C., more preferably at most 100° C. and most preferably at most 75° C. Particularly preferred production processes based on pelleting are carried out at temperatures 10° C. and, in particular, at most 5° C. above the melting temperature of the binder or the upper temperature limit of the melting range of the binder.

Another press agglomeration process which may be used in accordance with the invention is tabletting. Shaped bodies of detergents are produced by this process. Accordingly, in another preferred embodiment of the invention, the detergents are present in the form of shaped bodies, preferably tablets which may consist of a single phase or of several, more particularly two or three, different phases.

In order to facilitate the disintegration of heavily compacted tablets, disintegration aids, so-called tablet disintegrators, may be incorporated in the basic tablets to shorten their disintegration times. According to Römpp (9th Edition, Vol. 6, page 4440) and Voigt "*Lehrbuch der pharmazeutischen Technologie*" (6th Edition, 1987, pages 182–184), tablet disintegrators or disintegration accelerators are auxiliaries which promote the rapid disintegration of tablets in water or gastric juices and the release of the pharmaceuticals in an absorbable form.

These substances, which are also known as "disintegrators" by virtue of their effect, are capable of undergoing an increase in volume on contact with water so that, on the one hand, their own volume is increased (swelling) and, on the other hand, a pressure can be generated through the release of gases which causes the tablet to disintegrate into relatively small particles. Well-known disintegrators are, for example, carbonate/citric acid systems, although other organic acids may also be used. Swelling disintegration aids are, for example, synthetic polymers, such as polyvinyl pyrrolidone (PVP), or natural polymers and modified natural substances, such as cellulose and starch and derivatives thereof, alginates or casein derivatives.

Preferred detergent tablets contain 0.5 to 10% by weight, preferably 3 to 7% by weight and more preferably 4 to 6% by weight of one or more disintegration aids, based on the weight of the tablet.

According to the invention, preferred disintegrators are cellulose-based disintegrators, so that preferred detergent tablets contain a cellulose-based disintegrator in quantities of 0.5 to 10% by weight, preferably 3 to 7% by weight and more preferably 4 to 6% by weight. Pure cellulose has the formal empirical composition $(C_6H_{10}O_5)_n$ and, formally, is a $\beta$-1,4-polyacetal of cellobiose which, in turn, is made up of two molecules of glucose. Suitable celluloses consist of ca. 500 to 5000 glucose units and, accordingly, have average molecular weights of 50,000 to 500,000. According to the invention, cellulose derivatives obtainable from cellulose by polymer-analog reactions may also be used as cellulose-based disintegrators. These chemically modified celluloses include, for example, products of esterification or etherification reactions in which hydroxy hydrogen atoms have been substituted. However, celluloses in which the hydroxy groups have been replaced by functional groups that are not attached by an oxygen atom may also be used as cellulose derivatives. The group of cellulose derivatives includes, for example, alkali metal celluloses, carboxymethyl cellulose (CMC), cellulose esters and ethers and aminocelluloses. The cellulose derivatives mentioned are preferably not used on their own, but rather in the form of a mixture with cellulose as cellulose-based disintegrators. The content of cellulose derivatives in mixtures such as these is preferably below 50% by weight and more preferably below 20% by weight, based on the cellulose-based disintegrator. In one particularly preferred embodiment, pure cellulose free from cellulose derivatives is used as the cellulose-based disintegrator.

The cellulose used as disintegration aid is preferably not used in fine-particle form, but is converted into a coarser form, for example by granulation or compacting, before it is added to and mixed with the premixes to be tabletted. Detergent tablets which contain granular or optionally co-granulated disintegrators are described in German patent applications DE 197 09 991 (Stefan Herzog) and DE 197 10 254 (Henkel) and in International patent application WO 98/40463 (Henkel). Further particulars of the production of granulated, compacted or co-granulated cellulose disintegrators can also be found in these patent applications. The particle sizes of such disintegration aids is mostly above 200 µm, preferably at least 90% by weight of the particles being between 300 and 1600 µm in size and, more particularly, between 400 and 1200 µm in size. According to the invention, the above-described relatively coarse-particle cellulose-based disintegrators described in detail in the cited patent applications are preferably used as disintegration aids and are commercially obtainable, for example under the name of Arbocel® TF-30-HG from Rettenmaier.

Microcrystalline cellulose may be used as another cellulose-based disintegration aid or as part of such a component. This microcrystalline cellulose is obtained by partial hydrolysis of the celluloses under conditions which only attack and completely dissolve the amorphous regions (ca. 30% of the total cellulose mass) of the celluloses, but leave the crystalline regions (ca. 70%) undamaged. Subsequent de-aggregation of the microfine celluloses formed by hydrolysis provides the microcrystalline celluloses which have primary particle sizes of ca. 5 µm and which can be compacted, for example, to granules with a mean particle size of 200 µm.

According to the invention, preferred detergent tablets additionally contain a disintegration aid, preferably a cellulose-based disintegration aid, preferably in granular, co-granulated or compacted form, in quantities of 0.5 to 10% by weight, preferably in quantities of 3 to 7% by weight and more preferably in quantities of 4 to 6% by weight, based on tablet weight.

The tablets according to the invention are produced in step a) by first dry-mixing the ingredients—which may be completely or partly pregranulated—and then shaping/forming, more particularly tabletting, the resulting mixture using conventional processes. To produce the tablets according to the invention, the premix is compacted between two punches in a die to form a solid compactate. This process, which is referred to in short hereinafter as tabletting, comprises four phases, namely metering, compacting (elastic deformation), plastic deformation and ejection.

The premix is first introduced into the die, the filling level and hence the weight and shape of the tablet formed being determined by the position of the lower punch and the shape of the die. Uniform dosing, even at high tablet throughputs, is preferably achieved by volumetric dosing of the premix. As the tabletting process continues, the top punch comes into contact with the premix and continues descending towards the bottom punch. During this compaction phase, the particles of the premix are pressed closer together, the void volume in the filling between the punches continuously diminishing. The plastic deformation phase in which the particles coalesce and form the tablet begins from a certain position of the top punch (and hence from a certain pressure on the premix). Depending on the physical properties of the premix, its constituent particles are also partly crushed, the premix sintering at even higher pressures. As the tabletting rate increases, i.e. at high throughputs, the elastic deformation phase becomes increasingly shorter so that the tablets formed can have more or less large voids. In the final step of the tabletting process, the tablet is forced from the die by the bottom punch and carried away by following conveyors. At this stage, only the weight of the tablet is definitively established because the tablets can still change shape and size as a result of physical processes (re-elongation, crystallographic effects, cooling, etc.).

The tabletting process is carried out in commercially available tablet presses which, in principle, may be equipped with single or double punches. In the latter case, not only is the top punch used to build up pressure, the bottom punch also moves towards the top punch during the tabletting process while the top punch presses downwards. For small production volumes, it is preferred to use eccentric tablet presses in which the punch(es) is/are fixed to an eccentric disc which, in turn, is mounted on a shaft rotating at a certain speed. The movement of these punches is comparable with the operation of a conventional four-stroke engine. Tabletting can be carried out with a top punch and a bottom punch, although several punches can also be fixed to a single eccentric disc, in which case the number of die bores is correspondingly increased. The throughputs of eccentric presses vary according to type from a few hundred to at most 3,000 tablets per hour.

For larger throughputs, rotary tablet presses are generally used. In rotary tablet presses, a relatively large number of dies is arranged in a circle on a so-called die table. The number of dies varies—according to model—between 6 and 55, although even larger dies are commercially available. Top and bottom punches are associated with each die on the die table, the tabletting pressures again being actively built up not only by the top punch or bottom punch, but also by both punches. The die table and the punches move about a common vertical axis, the punches being brought into the filling, compaction, plastic deformation and ejection positions by means of curved guide rails. At those places where the punches have to be raised or lowered to a particularly significant extent (filling, compaction, ejection), these curved guide rails are supported by additional push-down members, pull-down rails and ejection paths. The die is filled from a rigidly arranged feed unit, the so-called filling shoe, which is connected to a storage container for the premix. The pressure applied to the premix can be individually adjusted through the tools for the top and bottom punches, pressure being built up by the rolling of the punch shank heads past adjustable pressure rollers.

To increase throughput, rotary presses can also be equipped with two filling shoes so that only half a circle has to be negotiated to produce a tablet. To produce two-layer or multiple-layer tablets, several filling shoes are arranged one behind the other without the lightly compacted first layer being ejected before further filling. Given suitable process control, shell and bull's-eye tablets—which have a structure resembling an onion skin—can also be produced in this way. In the case of bull's-eye tablets, the upper surface of the core or rather the core layers is not covered and thus remains visible. Rotary tablet presses can also be equipped with single or multiple punches so that, for example, an outer circle with 50 bores and an inner circle with 35 bores can be simultaneously used for tabletting. Modern rotary tablet presses have throughputs of more than one million tablets per hour.

Tabletting machines suitable for the purposes of the invention can be obtained, for example, from the following companies: Apparatebau Holzwarth GbR, Asperg, Wilhelm Fette GmbH, Schwarzenbek, Hofer. GmbH, Weil, KILIAN, Cologne, KOMAGE, Kell am See, KORSCH Pressen GmbH, Berlin, Mapag Maschinenbau AG, Bern (Switzerland) and Courtoy N.V., Halle (BE/LU). One example of a particularly suitable tabletting machine is the model HPF 630 hydraulic double-pressure press manufactured by LAEIS, D.

The tablets can be made in certain shapes and certain sizes. Suitable shapes are virtually any easy-to-handle shapes, for example slabs, bars, cubes, squares and corresponding shapes with flat sides and, in particular, cylindrical forms of circular or oval cross-section. This last embodiment encompasses shapes from tablets to compact cylinders with a height-to-diameter ratio of more than 1.

The portioned pressings may be formed as separate individual elements which correspond to a predetermined dose of the detergent. However, it is also possible to form pressings which combine several such units in a single pressing, smaller portioned units being easy to break off in particular through the provision of predetermined weak spots. For the use of laundry detergents in machines of the standard European type with horizontally arranged mechanics, it can be of advantage to produce the portioned pressings as cylindrical or square tablets, preferably with a diameter-to-height ratio of about 0.5:2 to 2:0.5. Commercially available hydraulic presses, eccentric presses and rotary presses are particularly suitable for the production of pressings such as these.

The three-dimensional form of another embodiment of the tablets according to the invention is adapted in its dimensions to the dispensing compartment of commercially available domestic washing machines, so that the tablets can be introduced directly, i.e. without a dosing aid, into the dispensing compartment where they dissolve on contact with water. However, it is of course readily possible—and preferred in accordance with the present invention—to use the detergent tablets in conjunction with a dosing aid.

Another preferred tablet which can be produced has a plate-like or slab-like structure with alternately thick long segments and thin short segments, so that individual segments can be broken off from this "bar" at the predetermined weak spots, which the short thin segments represent, and introduced into the machine. This "bar" principle can also be embodied in other geometric forms, for example vertical triangles which are only joined to one another at one of their longitudinal sides.

In another possible embodiment, however, the various components are not compressed to form a single tablet, instead the tablets obtained comprise several layers, i.e. at least two layers. These various layers may have different dissolving rates. This can provide the tablets with favorable performance properties. If, for example, the tablets contain components which adversely affect one another, one component may be integrated in the more quickly dissolving layer while the other component may be incorporated in a more slowly dissolving layer so that the first component can already have reacted off by the time the second component dissolves. The various layers of the tablets can be arranged in the form of a stack, in which case the inner layer(s) dissolve at the edges of the tablet before the outer layers have completely dissolved. Alternatively, however, the inner layer(s) may also be completely surrounded by the layers lying further to the outside which prevents constituents of the inner layer(s) from dissolving prematurely.

In another preferred embodiment of the invention, a tablet consists of at least three layers, i.e. two outer layers and at least one inner layer, a peroxy bleaching agent being present in at least one of the inner layers whereas, in the case of the stack-like tablet, the two cover layers and, in the case of the envelope-like tablet, the outermost layers are free from peroxy bleaching agent. In another possible embodiment, peroxy bleaching agent and any bleach activators or bleach catalysts present and/or enzymes may be spatially separated from one another in one and the same tablet. Multilayer tablets such as these have the advantage that they can be used not only via a dispensing compartment or via a dosing unit which is added to the wash liquor, instead it is also possible in cases such as these to introduce the tablet into the machine in direct contact with the fabrics without any danger of spotting by bleaching agent or the like.

Similar effects can also be obtained by coating individual constituents of the detergent composition to be compressed or the tablet as a whole. To this end, the tablets to be coated may be sprayed, for example, with aqueous solutions or emulsions or a coating may be obtained by the process known as melt coating.

After pressing, the detergent tablets have high stability. The fracture resistance of cylindrical tablets can be determined via the diametral fracture stress. This in turn can be determined in accordance with the following equation:

$$= \frac{2P}{Dt}$$

where represents the diametral fracture stress (DFS) in Pa, P is the force in N which leads to the pressure applied to the tablet that results in fracture thereof, D is the diameter of the tablet in meters and t is its height.

The present invention also relates to cosmetic hair or skin care preparations which contain silicic acid ester mixtures containing silicic acid esters corresponding to the following formulae:

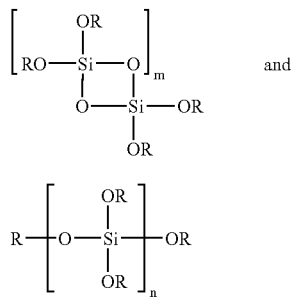

in which all the R's independently of one another are selected from the group consisting of H, linear or branched, saturated or unsaturated, substituted or unsubstituted $C_{1-6}$ hydrocarbon radicals and the perfume alcohols and biocide alcohols and m assumes a value of 1 to 20 and n a value of 2 to 100.

These cosmetic preparations preferably contain silicic acid esters corresponding to formulae I and II in quantities of 0.001 to 10% by weight, preferably 0.01 to 5% by weight, more preferably 0.02 to 3% by weight and most preferably 0.05 to 2% by weight, based on the detergent.

In a preferred embodiment, the cosmetic preparations are water-based preparations containing surface-active ingredients which are particularly suitable for the treatment of keratin fibers, more particularly human hair, or for the treatment of skin.

The hair treatment preparations mentioned are in particular preparations for treating human head hair. The most common preparations in this category may be divided in hair shampoos, hair care preparations, hair setting preparations and hair shaping preparations and also hair colorants and hair removers. Preferred preparations according to the invention containing surface-active ingredients are in particular hair care and washing preparations. A hair washing preparation or shampoo consists of 10 to 20 and, in some cases, as many as 30 ingredients. These water-containing preparations are generally present in liquid or paste-like form.

Fatty alcohol polyglycol ether sulfates (ether sulfates, alkyl ether sulfates), partly in combination with other, generally anionic surfactants, are mainly used for the most important group of ingredients, the surface-active ingredients or "washing-active" constituents. Besides good cleaning performance and immunity to water hardness, shampoo surfactants are intended to show dermatological and mucous membrane compatibility. Ready biodegradability is a legal requirement. Besides the alkyl ether sulfates, preferred preparations also contain other surfactants, such as alkyl sulfates, alkyl ether carboxylates, preferably with degree of ethoxylation of 4 to 10, and surface-active protein/fatty acid condensates. Protein/abietic acid condensate is particularly mentioned in this regard. Sulfosuccinic acid esters, amidopropyl betaines, amphoacetates and amphodiacetates and also alkyl polyglycosides are other preferred surfactants for hair shampoos. Another, very diverse group of ingredients are the auxiliaries. For example, large additions of nonionic surfactants, such as ethoxylated sorbitan esters or protein hydrolyzates, improve compatibility or have a germ-reducing effect, for example in baby shampoos; natural oils or synthetic fatty acid esters, for example, act as refatting agents for preventing excessive degreasing in the washing of hair; glycerol, sorbitol, propylene glycol (see propanediols), polyethylene glycols and other polyols act as moisturizers. Cationic surfactants, such as quaternary ammonium compounds for example, may be added to the shampoos to improve wet combability and reduce electrostatic charging of the hair after drying. Dyes and pearlizing pigments are added to obtain a colored, sparkling appearance. Thickeners belonging to various classes of compounds may be used to adjust the required viscosity. pH stability is achieved by buffers, for example based on citrate, lactate or phosphate. Preservatives, such as 4-hydroxybenzoic acid ester for example, are added to guarantee stability and storability. Ingredients sensitive to oxidation can be protected by addition of antioxidants, such as ascorbic acid, butyl methoxyphenol or tocopherol.

A third group of ingredients is formed by special active principles for special shampoos, for example oils, herb extracts, proteins, vitamins and lecithins in shampoos for greasy hair, for particularly dry hair, for damaged or stressed hair. Active principles in anti-dandruff shampoos mostly have a broad growth-inhibiting effect against fungi and bacteria. The fungistatic properties in particular, for example of pyrithione salts, were shown to be responsible for a good anti-dandruff effect. The shampoos contain perfume oils for a pleasant perfume note. The shampoos may exclusively contain the silicic acid esters according to the invention although, in another preferred embodiment, they contain not only these but also other perfumes. Any of the usual perfumes allowed in shampoos may be used.

The object of hair care preparations is to keep freshly regrown hair in its natural state for as long as possible and to restore it in the event of damage. Features which characterize this natural state are a silky luster, low porosity, bouncy and soft body and a pleasantly soft feel. An important requirement in this regard is a clean, dandruff-free and not too greasy scalp. Hair care preparations today include a number of different products of which the most important representatives are pretreatments, hair lotions, styling aids, rinses and conditioners and of which the composition—as with shampoos—is roughly divided into basic ingredients, auxiliaries and special active principles.

Basic ingredients include fatty alcohols, above all cetyl alcohol (1-hexadecanol) and stearyl alcohol (1-octadecanol), waxes, such as beeswax, wool wax (lanolin), spermaceti and synthetic waxes, paraffins, Vaseline, paraffin oil and—as solvents—above all ethanol, 2-propanol and water. Auxiliaries are emulsifiers, thickeners, preservatives, antioxidants, dyes and perfume oils. Today, the most important group of special active principles in hair care preparations are the quaternary ammonium compounds. These are divided into monomeric quaternary ammonium compounds (for example alkyl trimethylammonium halide with above all the lauryl, cetyl or stearyl group as the alkyl group) and polymeric quaternary ammonium compounds [for example quaternary cellulose ether derivatives or poly(N,N-dimethyl-3,4-methylenepyrrolidinium chloride)]. Their effect in hair care preparations is based on the fact that the positive charge of the nitrogen atoms of this compound can be added onto the negative charges of the hair keratin; through its higher cysteic acid content, damaged hair contains more negatively charged acid groups and, accordingly, can take up more quaternary ammonium compounds. These quaternary ammonium compounds—also known as "cationic hair care agents" because of their cationic character—have a smoothing effect on the hair, improve combability, reduce electrostatic charging and improve feel and luster. The polymeric quaternary ammonium compounds adhere to the hair so well that their effect is still in evidence after several washes. Organic acids, such as citric acid, tartaric-acid or lactic acid, are often used to establish an acidic medium. The water-soluble protein hydrolyzates are readily absorbed onto the hair keratin by virtue of their close chemical relationship. The largest group of special active principles in hair care preparations consists of various plant extracts and vegetable oils of which most have been in use for some time without their effectiveness having been attributed scientifically satisfactorily in every case to their particular effect. Similarly, the effectiveness of vitamins used in hair care preparations has only been established in individual cases. To avoid overrapid refatting, some hair lotions contain substances, such as certain tar ingredients, cysteic acid derivatives or glycyrrhizin; the intended reduction of sebaceous gland production has also not been clearly established. By contrast, the effectiveness of anti-dandruff agents has been satisfactorily demonstrated. Accordingly, they are used in corresponding hair lotions and other hair care preparations.

The water-based preparations for treating skin are, in particular, skin care preparations. Skin care begins with cleansing for which soaps are primarily used. Soaps are divided into solid soaps, usually bar soaps, and liquid soaps. In a preferred embodiment, therefore, the cosmetic preparations are present in the form of shaped bodies which contain surface-active ingredients. In one preferred embodiment, the most important ingredients of such shaped bodies are the alkali metal salts of the fatty acids of natural oils and fats, preferably with chains of 12 to 18 carbon atoms. Since lauric acid soaps foam particularly well, coconut oil and palm kernel oil soaps rich in lauric acid are preferred raw materials for the production of toilet soaps. The sodium salts of the fatty acid mixtures are solid and their potassium salts soft and paste-like. For saponification, the dilute sodium or potassium hydroxide solution is added to the fatty raw materials in a stoichiometric ratio so that a hydroxide excess of max. 0.05% is present in the final soap. In many cases, soaps today are no longer produced directly from the fats, but instead from the fatty acids obtained by lipolysis. Typical soap additives are fatty acids, fatty alcohols, lanolin, lecithin, vegetable oils, partial glycerides and other fat-like substances for refatting the cleansed skin, antioxidants, such as ascorbyl palmitate or tocopherol, for preventing autoxidation of the soap (rancidity), complexing agents, such as nitrilotriacetate, for binding traces of heavy metals which could catalyze autoxidative deterioration, perfume oils for obtaining the required perfume notes, dyes for coloring the bar soaps and optionally special additives.

The most important types of toilet soaps are:
  toilet soaps containing 20–50% coconut oil in the fatty component, up to 5% refatting agents and 0.5–2% perfume oil—they form the largest proportion of toilet soaps;
  luxury soaps containing up to 5% perfume oils, in some cases particularly expensive perfume oils;
  deodorant soaps with additions of deodorizing agents such as, for example, 3,4,4'-trichlorocarbanilide (Triclocarban);
  cream soaps with particularly high percentages of refatting and skin-creaming substances;
  baby soaps with good refatting and additional skin care ingredients such as, for example, camomile extracts, at best very weakly perfumed;
  skin protecting soaps with high percentages of refatting agents and other skin care and protecting additives, for example proteins;
  transparent soaps with additions of glycerine, sugars and the like which prevent the fatty acid salts from crystallizing in the solidified soap melt and are thus responsible for a transparent appearance;
  floating soaps with a density of <1 produced by air bubbles incorporated under control during the production process.

Soaps can also be provided with abrasive additives for cleaning particularly soiled hands. Where soap is used for washing, a pH of 8 to 10 is automatically established in the wash liquor. This alkalinity neutralizes the natural acid jacket of the skin (pH 5–6). Although this is reformed relatively quickly in the case of normal skin, irritation can occur in the case of sensitive or predamaged skin. Another disadvantage of soaps is the formation of insoluble lime soaps in hard water. These disadvantages do not arise with syndet soaps. They are based on synthetic anionic surfactants which may be processed with builders, refatting agents and other additives to form soap-like bars. Their pH value is variable within wide limits and is generally adjusted to a neutral pH of 7 or—in adaptation to the acid jacket of the skin—to a pH of 5.5. They have excellent cleaning performance, but foam in any water hardness and even in sea water. On account of their intensive cleaning and degreasing effect, the percentage of refatting additives has to be far higher than in normal soaps. The disadvantage of syndet soaps is their relatively high price.

Liquid soaps are based both on potassium salts of natural fatty acids and on synthetic anionic surfactants. They contain fewer washing-active substances than solid soaps in aqueous solution and have the usual additives, optionally with viscosity-regulating constituents and pearlizing additives. On account of their convenient and hygienic application from dispensers, they are mainly used in public toilets and the like. Wash lotions for particularly sensitive skin are based on mild-acting synthetic surfactants with additions of skin care substances and are adjusted to a neutral or mildly acidic pH (5.5).

There are a number of other preparations for mainly facial cleansing, including face lotions, cleansing lotions, milks, creams, pastes; face packs are used partly for cleaning, but mainly for invigorating and caring for facial skin. Face lotions are mostly water/alcohol solutions with low surfactant contents and other skin care agents. Cleansing lotions, milks, creams and pastes are mostly based on o/w emulsions with relatively small contents of fatty components and cleansing and skin-care additives. So-called scruffing and peeling preparations contain mildly keratolytic substances for removing the uppermost, dead horny layers of skin, in some cases with additions of abrasive powders. The almond paste long used as a mild skin cleanser is still often a constituent of such preparations. In addition, preparations for cleaning dirty skin contain antibacterial and anti-inflammatory substances because the accumulations of tallow in comedos (blackheads) form nutrient media for bacterial infections and tend towards inflammation. The broad range of various skin cleansing products available varies in composition and content of diverse active substances according to the various skin types and to special treatment goals.

The bath additives available for cleansing the skin in bathtubs or shower cubicles are widely used. Bath salts and bath tablets are intended to soften, color and perfume the bath water and generally contain no washing-active substances. By softening the bathwater, they enhance the cleansing power of soaps, but are primarily intended to have an invigorating effect and to add to the pleasure of bathing. Foam baths are relatively important. Where they have a relatively high content of refatting agents and skin care additives, they are also known as cream baths.

Shower baths have been successful on the market besides foam baths since about 1970 and, since 1986, have outstripped them in terms of production volume. They are similar in composition to liquid hair shampoos, but instead of hair care additives, contain special skin care additives. Combined preparations suitable for the skin and hair have also recently appeared on the market.

The care of the skin after cleansing has two key objectives: on the one hand, it is intended to return to the skin the ingredients removed uncontrollably during washing, such as horny cells, sebum lipids, acid formers and water, and to re-establish the natural equilibrium state, on the other hand it is intended to counteract above all the natural ageing process of the skin and the possible damage attributable to weather and environmental influences. Skin care and skin protecting preparations are available in large numbers and in many forms. The most important are skin creams, lotions, oils and gels. Creams and lotions are based on o/w (oil-in-water) emulsions or w/o (water-in-oil) emulsions. The main constituents of the oil or fatty or lipid phase are fatty alcohols, fatty acids, fatty acid esters, waxes, Vaseline, paraffins and other fatty and oil components of mainly natural origin. Besides water, the aqueous phase mainly contains moisture-regulating and moisture-sustaining substances as key skin care ingredients and also consistency or viscosity-regulating additives. Other additives, such as preservatives, antioxidants, complexing agents, perfume oils, colorants and special active principles, are incorporated in one of the two above-mentioned phases according to their solubility and their stability properties. The choice of the emulsifier system is crucial to the type of emulsion and its properties. The emulsifier system may be selected on the HLB principle.

Creams may be divided into "day creams" and "night creams" according to their range of application. Day creams are mostly built up as o/w emulsions and are quickly absorbed by the skin without leaving any greasiness behind. Because of this, they are also sometimes referred to as dry creams, matt creams or vanishing creams. Night creams are mostly w/o emulsions, are absorbed relatively slowly by the skin and often contain special active principles which are supposed to regenerate the skin during sleep. Some of these preparations are also known as "nourishing creams" although "nourishing" of the cell metabolism in the skin can only take place via the circulation; accordingly, the name "nourishing cream" is disputed. So-called cold creams are mixed o/w and w/o emulsions, the oil phase quantitatively predominating. With traditional cold creams, the unstably emulsified water was released during application and, by evaporating, produced a cooling effect which gave this preparation its name.

The many special ingredients used in skin care preparations and the effects attributed to them cannot be discussed in detail here. They include milk protein products, egg yolk, lecithins, lipoids, phosphatides, cereal germ oils, vitamins—especially vitamin F and the biotin formerly known as skin vitamin (vitamin H)—and hormone-free placenta extracts. Hormones sometimes previously used are no longer used because they are classified as medicinal active principles and cannot be used in cosmetic preparations.

Skin oils are one of the oldest forms of skin care products and are still used today. They are based on non-drying vegetable oils, such as almond oil or olive oil with additions of natural vitamin oils, such as wheat germ oil or avocado oil, and oily plant extracts from, for example, St. John's wort, camomile and the like. The addition of antioxidants against rancidity is essential; desired perfume notes are obtained by addition of perfume or essential oils; an addition of paraffin oil or liquid fatty acid esters optimizes the performance properties.

Skin gels are semisolid, transparent products which are stabilized by corresponding gel formers. They are divided into oleogels (water-free), hydrogels (oil-free) and oil/water gels. The type selected will depend on the desired application. The oil/water gels contain large amounts of emulsifier and have certain advantages over emulsions both from the aesthetic perspective and from the application perspective.

Footbaths are intended to have a cleansing, refreshing, circulation-promoting, invigorating and deodorizing effect and a softening effect on hard skin. Footbath additives are available as bath salts and foam baths. They consist, for example, of basic mixtures of sodium carbonate, sodium hydrogen carbonate and sodium perborate or sodium hexametaphosphate (see. condensed phosphates), sodium sulfate, sodium perborate and 1% sodium lauryl sulfate as the foam component with antihydrotic, deodorizing, optionally bactericidal and/or fungicidal additives and also dyes and perfumes. Foot powders—which are applied after washing of the feet and/or are scattered into stockings and shoes—are intended to have a skin-smoothing, cooling, moisture-absorbing, perspiration-inhibiting, antiseptic and deodorizing effect and a softening effect on hard skin. They generally consist of up to 85% talcum (see talcum) with additions of silica powder, aluminium hydroxychloride, salicylic acid and optionally bactericides, fungicides, deodorants and perfumes. Foot creams or foot balsams are used for skin care and for massaging foot and lower leg muscles. Foot creams are generally o/w emulsions of, for example, 30% isopropyl myristate, 10% polysorbate, 4.2% aluminium metahydroxide and 55.8% water as the basic formulation; foot balsams are mostly water-free and contain, for example, 85% Vaseline, 5% paraffin, 3% lanolin, 3% methyl salicylate, 2% camphor, 1% menthol and 1% eucalyptus oil. Hard skin removers such as, for example, "rubbing creams" are rubbed into the skin until the horny layer is removed in the form of crumbs. A basic formulation consists of 25% paraffin, 2% stearic acid, 2% beeswax, 2% spermaceti, 2% glycerol monostearate, 0.5% 2,2',2"-nitrilotriethanol, 1% perfume oil, 0.2% 4-hydroxybenzoic acid and 65.3% water. Nail groove tinctures are used to soften horny skin in the nail grooves and to keep the edges of ingrowing nails soft, mainly on the big toes. A basic formulation consists of 10% 2,2',2"-nitrilotriethanol, 15% urea, 0.5% fatty alcohol polyglycol ether and 74.5% water.

Other preferred cosmetic preparations according to the invention are preparations for influencing body odor, more especially deodorants. Deodorants are intended to mask, remove or destroy odors. Unpleasant body odors are formed by the bacterial decomposition of perspiration, particularly in the damp underarm region where microorganisms find good living conditions. Accordingly, the most important ingredients of deodorants are germ-inhibiting substances. Particularly preferred germ inhibitors are those which show largely selective activity against the bacteria responsible for body odor. However, preferred active principles merely have a bacteriostatic effect and do not kill off all the bacterial flora. Germ inhibitors are generally any suitable preservatives which act specifically against gram-positive bacteria. Examples include Irgasan DP 300 (Triclosan, 2,4,4'-trichloro-2'-hydroxydiphenylether), chlorhexidine (1,1'-hexamethylene-bis-(5-(4'-chlorophenyl)-biguanide) and 3,4,4'-trichlorocarbanilide. Quaternary ammonium compounds are also suitable in principle. In view of their strong antimicrobial activity, all these substances are preferably used in low concentrations of about 0.1 to 0.3% by weight. In addition, many perfumes also have antimicrobial properties. Accordingly, perfumes such as these with antimicrobial properties are preferably used in deodorants. Farnesol and phenoxyethanol are particularly mentioned in this connection. In a particularly preferred embodiment, therefore, the deodorants according to the invention contain bacteriostatic perfumes. The perfumes may again preferably be present in the form of silicic acid esters. However, these antibacterial perfumes need not be used in the form of silicic acid esters but rather in the form of mixtures with other perfumes present as silicic acid esters. Another group of key ingredients of deodorants are enzyme inhibitors which inhibit the decomposition of perspiration by enzymes such as, for example, citric acid triethyl ester or zinc glycinate. Other key ingredients of deodorants are antioxidants which are intended to prevent the ingredients of perspiration from oxidizing.

In another preferred embodiment of the invention, the cosmetic preparation is a hair setting preparation which contains polymers for setting. In a particularly preferred embodiment, at least one of the polymers is a polyurethane.

In a preferred embodiment, the preparations according to the invention may contain water-soluble polymers from the group of nonionic, anionic, amphoteric and zwitterionic polymers.

Water-soluble polymers in the context of the invention are polymers of which more than 2.5% by weight dissolves in water at room temperature.

According to the invention, preferred water-soluble polymers are nonionic. The following are examples of suitable nonionic polymers:

Polyvinyl pyrrolidones of the type marketed under the name of Luviskol® (BASF).

Vinyl pyrrolidone/vinyl ester copolymers of the type marketed, for example, under the trade mark Luviskol® (BASF). Luviskol® VA 64 and Luviskol® VA, both vinyl pyrrolidone/vinyl acetate copolymers, are particularly preferred nonionic polymers.

Cellulose ethers, such as the hydroxypropyl cellulose, hydroxyethyl cellulose and methyl hydroxypropyl cellulose marketed under the trade marks Culminal® and Benecel® (AQUALON).

Suitable amphoteric polymers are, for example, the octylacrylamide/methyl methacrylate/tert.butylaminoethyl methacrylate/2-hydroxypropyl methacrylate copolymers obtainable under the names of Amphomer® and Amphomer® LV-71 (DELFT NATIONAL).

Suitable zwitterionic polymers are, for example, the polymers disclosed in German patent applications DE 39 29 973, DE 21 50 557, DE 28 17 369 and DE 37 08 451. Acrylamidopropyl trimethyl ammonium chloride/(meth)acrylic acid copolymers and alkali metal and ammonium salts thereof are particularly preferred zwitterionic polymers. Other suitable zwitterionic polymers are the methacroyl ethyl betaine/methacrylate copolymers commercially obtainable under the name of Amersette® (AMERCHOL).

According to the invention, suitable anionic polymers are inter alia:

Vinyl acetate/crotonic acid copolymers as commercially obtainable, for example, under the names of Resyn® (National Starch), Luviset® (BASF) and Gafset® (GAF).

Vinyl pyrrolidone/vinyl acrylate copolymers obtainable, for example, under the name of Luviflex® (BASF). A preferred polymer is the vinyl pyrrolidone/acrylate terpolymer obtainable under the name of Luviflex® VBM-35 (BASF).

Acrylic acid/ethyl acrylate/N-tert.butyl acrylamide terpolymers marketed, for example, under the name of Ultrahold® strong (BASF).

In cases where the polyurethane contains ionic groups, it has proved to be useful for other water-soluble polymers to be nonionic or to have the same ionicity.

The hair treatment preparations according to the invention preferably contain water-soluble polymers in quantities of 0.01 to 20% by weight and more particularly in quantities of 0.1 to 10% by weight (based on the preparation as a whole) according to the particular type of hair treatment preparation.

The polyurethanes and the water-soluble polymers are preferably present in the preparations according to the invention in a quantity ratio of 1:10 to 10:1. A quantity ratio of 2:1 to 1:1 has proved to be particularly suitable in many cases.

The hair setting preparations according to the invention are in particular setting lotions, hair sprays and setting gels. Hair sprays are a particularly preferred embodiment of the hair setting preparations according to the invention.

In another preferred embodiment, the preparations according to the invention may also be formulated as a foam aerosol using a propellent.

Other constituents of the compositions according to the invention may be, for example:

anionic surfactants such as, for example, fatty alkyl sulfates and ether sulfates, cationic surfactants such as, for example, quaternary ammonium compounds, zwitterionic surfactants such as, for example, betaines, ampholytic surfactants, nonionic surfactants such as, for example, alkyl polyglycosides and ethoxylated fatty alcohols, structurants, such as glucose and maleic acid, hair-conditioning compounds, such as phospholipids, for example soya lecithin, egg lecithin and kephalins, and also silicone oils, protein hydrolyzates, more particularly elastin, collagen, keratin, milk protein, soya protein and wheat protein hydrolyzates, condensates thereof with fatty acids and quaternized protein hydrolyzates,
perfume oils containing the silicic acid esters according to the invention,
solubilizers, such as ethylene glycol, propylene glycol, glycerol and diethylene glycol,
dyes,
antidandruff agents, such as Piroctone Olamine and Zinc Omadine,
other substances for adjusting the pH value,
active substances, such as panthenol, allantoin, pyrrolidone carboxylic acids and salts thereof, plant extracts and vitamins,
UV filters,
consistency factors, such as sugar esters, polyol esters or polyol alkyl ethers,
fats and waxes, such as spermaceti, beeswax, montan wax, paraffins and fatty alcohols,
fatty acid alkanolamides,
complexing agents, such as EDTA, NTA and phosphonic acids,
swelling and penetration agents, such as glycerol, propylene glycol monoethyl ether, carbonates, hydrogen carbonates, guanidines, ureas and primary, secondary and tertiary phosphates,
propellents, such as propane/butane mixtures, $N_2O$, dimethyl ether, $CO_2$ and air,
antioxidants.

As already mentioned, the hair setting preparations according to the invention preferably also contain polymers from the class of polyurethanes. The polyurethanes consist of at least two different types of monomer,
a compound (A) containing at least 2 active hydrogen atoms per molecule and
a di- or polyisocyanate (B).

The compounds (A) may be, for example, diols, triols, diamines, triamines, polyetherols and polyesterols. The compounds containing more than 2 active hydrogen atoms are normally used in small quantities in combination with a large excess of compounds containing 2 active hydrogen atoms.

Examples of compounds (A) are ethylene glycol, 1,2- and 1,3-propylene glycol, butylene glycols, di-, tri-, tetra- and poly-ethylene and -propylene glycols, copolymers of lower alkylene oxides, such as ethylene oxide, propylene oxide and butylene oxide, ethylenediamine, propylenediamine, 1,4-diaminobutane, hexamethylenediamine and α,ω-diamines based on long-chain alkanes or polyalkylene oxides.

Polyurethanes where the compounds (A) are diols, triols and polyetherols may be preferred for the purposes of the invention. Polyethylene glycols and polypropylene glycols with molecular weights of 200 to 3,000 and more particularly in the range from 1,600 to 2,500 have proved to be particularly suitable in some cases.

Polyesterols are normally obtained by modification of compound (A) with dicarboxylic acids, such as phthalic acid, isophthalic acid and adipic acid.

Hexamethylene diisocyanate, 2,4- and 2,6-toluene diisocyanate, 4,4'-methylene di(phenylisocyanate) and, in particular, isophorone diisocyanate are mainly used as the compounds (B).

In addition, the polyurethanes used in accordance with the invention may contain structural elements such as diamines, for example, as chain extenders an hydroxycarboxylic acids.

Dialkylolcarboxylic acids such as dimethylolpropionic acid, for example, are particularly suitable hydroxy-carboxylic acids. So far as the other structural elements are concerned, there is no basic limitation, i.e. they may be nonionic, anionic or cationic structural elements.

Further information on the structure and production of polyurethanes can be found in articles in the relevant synoptic works, such as Römpps Chemie-Lexikon and Ullmanns Enzyklopädie der technischen Chemie.

Polyurethanes which have proved in many cases to be particularly suitable for the purposes of the invention may be characterized as follows:
only aliphatic groups in the molecule,
no free isocyanate groups in the molecule,
polyether and polyester polyurethanes,
anionic groups in the molecule.

It has also proved to be of advantage in some cases for the polyurethane to be stably dispersed and not dissolved in the system.

In addition, it has proved to be of advantage for the production of the preparations according to the invention if the polyurethanes are introduced in the form of aqueous dispersions, i.e. are not directly mixed with the other components. Such dispersions normally have a solids content of ca. 20–50% and more particularly ca. 35–45% and are even commercially obtainable.

The hair setting preparations according to the invention preferably contain the polyurethane in quantities of 0.1 to 15% by weight and more particularly 0.5 to 10% by weight, based on the preparation as a whole.

EXAMPLES

A Laundry Treatment Preparations/Laundry Detergents

15 Perfume oils with the compositions shown in Tables 1 to 3 were prepared. Perfume oils 1a, 2a and 3a contained three perfume alcohols in the form of their silicic acid esters according to the invention while comparison oils 1b, 2b and 3b contained equal quantities of the free perfume alcohols, i.e. were free from the compounds according to the invention. Examples 1c, 1d, 1e, 2c, 2d, 2e, 3c, 3d and 3e each contained two perfume alcohols and one perfume alcohol silicic acid ester according to the invention. The composition of the perfume oils (%o based on the, perfume oil as a whole) is shown in Tables 1 to 3.

TABLE 1

Perfume oils with a flowery, ozony perfume note (quantities in %)

| Ingredient | Formula 1a | Formula 1b | Formula 1c | Formula 1d | Formula 1e |
|---|---|---|---|---|---|
| Ethylene brassylate | 180 | 180 | 180 | 180 | 180 |
| ISO E Super | 135 | 135 | 135 | 135 | 135 |
| Hedione | 130 | 130 | 130 | 130 | 130 |
| Cyclohexyl salicylate Henkel | 100 | 100 | 100 | 100 | 100 |
| Lilial | 80 | 80 | 80 | 80 | 80 |
| Dihdyro-β-ionone | 60 | 60 | 60 | 60 | 60 |
| Troenan Henkel | 60 | 60 | 60 | 60 | 60 |
| Phenylethyl silicic acid ester | 45 | — | — | — | 45 |
| Phenylethyl alcohol | — | 45 | 45 | 45 | — |
| Geranyl silicic acid ester | 40 | — | — | 40 | — |
| Geraniol | — | 40 | 40 | — | 40 |
| Citronellyl silicic acid ester | 40 | — | 40 | — | — |
| Citronellol | — | 40 | — | 40 | 40 |
| Linalool | 37 | 37 | 37 | 37 | 37 |

TABLE 1-continued

Perfume oils with a flowery, ozony perfume note (quantities in %)

| Ingredient | Formula 1a | Formula 1b | Formula 1c | Formula 1d | Formula 1e |
|---|---|---|---|---|---|
| Helional | 34 | 34 | 34 | 34 | 34 |
| Eugenol pure | 10 | 10 | 10 | 10 | 10 |
| Canthoxal | 8 | 8 | 8 | 8 | 8 |
| Calone | 7 | 7 | 7 | 7 | 7 |
| Cyclovertal Henkel | 6 | 6 | 6 | 6 | 6 |
| Dimetol | 5 | 5 | 5 | 5 | 5 |
| Methyl anthranilate 10% in DPG | 5 | 5 | 5 | 5 | 5 |
| Decalactone Gamma | 4 | 4 | 4 | 4 | 4 |
| Phenylacetic acid | 3 | 3 | 3 | 3 | 3 |
| Damascenone 10% in DPG | 3 | 3 | 3 | 3 | 3 |
| Neroli Phase Oil | 3 | 3 | 3 | 3 | 3 |
| Cyclogalbanate | 2 | 2 | 2 | 2 | 2 |
| Indole | 1 | 1 | 1 | 1 | 1 |
| Isoeugenol methyl ether | 1 | 1 | 1 | 1 | 1 |
| Ambroxan Henkel | 1 | 1 | 1 | 1 | 1 |

TABLE 2

Perfume oils with fresh, rosy perfume note (quantities in %)

| Ingredient | Formula 2a | Formula 2b | Formula 2c | Formula 2d | Formula 2e |
|---|---|---|---|---|---|
| Hexyl cinnamaldehyde (Alpha) | 170 | 170 | 170 | 170 | 170 |
| Lilial | 170 | 170 | 170 | 170 | 170 |
| Ethyl linalool | 152 | 152 | 152 | 152 | 152 |
| Citronellyl silicic acid ester | 106 | — | — | — | 106 |
| Citronellol | — | 106 | 106 | 106 | — |
| Ethylene brassylate | 80 | 80 | 80 | 80 | 80 |
| Benzyl acetate | 41 | 41 | 41 | 41 | 41 |
| Cyclohexyl salicylate Henkel | 40 | 40 | 40 | 40 | 40 |
| Citronellyl acetate | 40 | 40 | 40 | 40 | 40 |
| Acetoacetic ester | 34 | 34 | 34 | 34 | 34 |
| Geranyl silicic acid ester | 30 | — | — | 30 | — |
| Geraniol | — | 30 | 30 | — | 30 |
| Phenylethyl silicic acid ester | 28 | — | 28 | — | — |
| Phenyl ethyl alcohol | — | 28 | — | 28 | 28 |
| Geranium oil Bourbon | 20 | 20 | 20 | 20 | 20 |
| Linalool | 14 | 14 | 14 | 14 | 14 |
| Isoraldein 70 | 10 | 10 | 10 | 10 | 10 |
| Indoflor | 5 | 5 | 5 | 5 | 5 |
| Ethyl vanillin 10% in DPG | 5 | 5 | 5 | 5 | 5 |
| Rose oxide R 10% in DPG | 5 | 5 | 5 | 5 | 5 |
| Muguet aldehyde 100% | 5 | 5 | 5 | 5 | 5 |
| Styrolyl acetate | 5 | 5 | 5 | 5 | 5 |
| Cuminaldehyde 10% in DPG | 5 | 5 | 5 | 5 | 5 |
| Calone 10% in DPG | 5 | 5 | 5 | 5 | 5 |
| Phenylacetal aldehyde dimethyl acetal | 5 | 5 | 5 | 5 | 5 |
| Cyclovertal 10% in DPG Henkel | 5 | 5 | 5 | 5 | 5 |
| Petit grain oil Parag. | 5 | 5 | 5 | 5 | 5 |
| Ethylphenyl acetate | 4 | 4 | 4 | 4 | 4 |
| Hexenyl acetate | 3 | 3 | 3 | 3 | 3 |
| Hexenol (Beta Gamma) | 3 | 3 | 3 | 3 | 3 |
| Hydratropa ald. Dim. Acetal. | 2 | 2 | 2 | 2 | 2 |
| Phenylethyl phenyl acetate | 1 | 1 | 1 | 1 | 1 |
| Cyclogalbanate | 1 | 1 | 1 | 1 | 1 |
| Ambroxan Henkel | 1 | 1 | 1 | 1 | 1 |

TABLE 3

Perfume oils with fresh, green perfume note (quantities in %)

| Ingredient | Formula 3a | Formula 3b | Formula 3c | Formula 3d | Formula 3e |
|---|---|---|---|---|---|
| Hexyl cinnamaldehyde (Alpha) | 274 | 274 | 274 | 274 | 274 |
| Dipropylene glycol | 200 | 200 | 200 | 200 | 200 |
| Phenylethyl silicic acid ester | 103 | — | — | — | 103 |
| Phenylethyl alcohol | — | 103 | 103 | 103 | — |
| Bergamot oil berg.-free | 100 | 100 | 100 | 100 | 100 |
| Cyclohexyl salicylate Henkel | 98.5 | 98.5 | 98.5 | 98.5 | 98.5 |
| Orange oil sweet ital. | 42 | 42 | 42 | 42 | 42 |
| Ethylene brassylate | 41 | 41 | 41 | 41 | 41 |
| Geranyl silicic acid ester | 35 | — | — | 35 | — |
| Geraniol | — | 35 | 35 | — | 35 |
| Citronellyl silicic acid ester | 24 | — | 24 | — | — |
| Citronellol | — | 24 | — | 24 | 24 |
| Linalyl acetate | 20 | 20 | 20 | 20 | 20 |
| Litsea cubeba oil | 15 | 15 | 15 | 15 | 15 |
| Linalool | 12 | 12 | 12 | 12 | 12 |
| Pinene beta P&F | 10 | 10 | 10 | 10 | 10 |
| Ionone beta synth. | 8 | 8 | 8 | 8 | 8 |
| Petit grain oil Parag. | 7 | 7 | 7 | 7 | 7 |
| Clary oil | 3 | 3 | 3 | 3 | 3 |
| Cyclovertal Henkel | 3 | 3 | 3 | 3 | 3 |
| Damascone beta | 2 | 2 | 2 | 2 | 2 |
| Allyl ionone (Cetone V) | 1 | 1 | 1 | 1 | 1 |
| Cedar leaf oil | 1 | 1 | 1 | 1 | 1 |
| Eucalytpus oil | 0.5 | 0.5 | 0.5 | 0.5 | 0.5 |

1% of perfume oils 1a and 1b were incorporated in a fabric softener concentrate containing 15% esterquat of which the composition is shown in Table 4. The laundry washed with perfume-free heavy-duty detergent was treated with quantities of 40 g of the fabric softeners in the final rinse cycle. After spin drying, the smell of the damp laundry was evaluated, after which the laundry was hung out on a line to dry. The smell of the dry laundry was evaluated 3 and 7 days after it had been taken off the line and stored in plastic bags.

The laundry "pairs" were evaluated for intensity=I and appeal=A by 8 experts (perfumists) in a direct comparison. The results of these preference tests are set out in Table 5. Similar tests were carried out for the comparison of perfume oils 1b/1d and 2b/2e. The results of these tests are set out in Tables 6 and 7.

TABLE 4

| Composition of the softener concentrate [% by weight] | |
|---|---|
| Dehyguart ® AU 46 | 15 |
| Perfume oil | 1 |
| Water, salts | Balance |

Dehyquart® AU 46

Dipalmitoleyloxyethyl hydroxyethyl methylammonium methoxysulfate, 90% in isopropanol, a product of Henkel KGaA, Düsseldorf

TABLE 5

Results of the fragrance tests on fabric-softened laundry (intensity preference I, appeal preference A), panel of 8 perfumists, perfume oil 1a/1b

|     | Damp laundry | | 1st Day | | Dry laundry 3rd Day | | 7th Day | |
| --- | --- | --- | --- | --- | --- | --- | --- | --- |
|     | I | A | I | A | I | A | I | A |
| 1a  | 4 | 6 | 5 | 7 | 7 | 6 | 8 | 8 |
| 1b  | 4 | 2 | 3 | 1 | 1 | 2 | 0 | 0 |

TABLE 6

Results of the fragrance tests on fabric-softened laundry (intensity preference I, appeal preference A), panel of 8 perfumists, perfume oil 1d/1b

|     | Damp laundry | | 1st Day | | Dry laundry 3rd Day | | 7th Day | |
| --- | --- | --- | --- | --- | --- | --- | --- | --- |
|     | I | A | I | A | I | A | I | A |
| 1d  | 3 | 4 | 6 | 6 | 8 | 5 | 8 | 6 |
| 1b  | 5 | 4 | 2 | 2 | 0 | 3 | 0 | 2 |

TABLE 7

Results of the fragrance tests on fabric-softened laundry (intensity preference I, appeal preference A), panel of 8 perfumists, perfume oil 2e/2b

|     | Damp laundry | | 1st Day | | Dry laundry 3rd Day | | 7th Day | |
| --- | --- | --- | --- | --- | --- | --- | --- | --- |
|     | I | A | I | A | I | A | I | A |
| 2e  | 5 | 6 | 4 | 5 | 7 | 7 | 8 | 7 |
| 2b  | 3 | 2 | 4 | 3 | 1 | 1 | 0 | 1 |

0.25% by weight of perfume oils 3a and 3b was added to a commercially available perfume-free laundry detergent. The laundry was washed at 60° C. with quantities of 150 g of this powder and rinsed three times with clear water. After spin drying, the smell of the damp laundry was evaluated, after which the laundry was hung out on a line to dry. The smell of the dry laundry was evaluated immediately, after 3 days and after 7 days, the laundry being stored in plastic bags.

The laundry "pairs" were evaluated for fragrance intensity=I and fragrance appeal=A by 7 experts (perfumists). The results of these tests are set out in Table 8; corresponding comparisons of perfume oils 3e/3b are shown in Table 9.

TABLE 8

Results of the fragrance tests on fabric-softened laundry (intensity preference I, appeal preference A), panel of 7 perfumists, perfume oil 3a/3b

|     | Damp laundry | | 1st Day | | Dry laundry 3rd Day | | 7th Day | |
| --- | --- | --- | --- | --- | --- | --- | --- | --- |
|     | I | A | I | A | I | A | I | A |
| 3a  | 6 | 5 | 4 | 3 | 6 | 5 | 7 | 6 |
| 3b  | 1 | 2 | 3 | 2 | 1 | 0 | 1 | 1 |

TABLE 9

Results of the fragrance tests on fabric-softened laundry (intensity preference I, appeal preference A), panel of 8 perfumists, perfume oil 3e/3b

|     | Damp laundry | | 1st Day | | Dry laundry 3rd Day | | 7th Day | |
| --- | --- | --- | --- | --- | --- | --- | --- | --- |
|     | I | A | I | A | I | A | I | A |
| 3e  | 5 | 5 | 4 | 3 | 6 | 5 | 7 | 6 |
| 3b  | 2 | 2 | 3 | 4 | 1 | 2 | 0 | 1 |

The results clearly show that even the partial replacement of the perfume alcohols by the silicic acid esters according to the invention leads to distinctly improved fragrance evaluations.

B Cleaners

B1 Acidic Cleaners

Perfume oils with compositions according to Table 10 were prepared. 10 A is a perfume oil according to the invention, 10 B a comparison perfume oil.

TABLE 10

Perfume oils for an acidic cleaner with an apple fragrance

| Ingredient | 10A Quantities in % | 10B Quantities in % |
| --- | --- | --- |
| Dynascone 10 | 5.0 | 5.0 |
| Cyclovertal | 7.5 | 7.5 |
| Hexyl acetate | 35.0 | 35.0 |
| Allyl heptanoate | 200.0 | 200.0 |
| Amyl butyrate | 5.0 | 5.0 |
| Prenyl acetate | 10.0 | 10.0 |
| Aldehyde C14 SOG | 70.0 | 70.0 |
| Manzanate | 15.0 | 15.0 |
| Melusate | 30.0 | 30.0 |
| Ortho tert.butyl cyclohexyl acetate | 200.0 | 200.0 |
| Cinnamaldehyde | 5.0 | 5.0 |
| Isobornyl acetate | 10.0 | 10.0 |
| Dihydrofloriffone TD | 2.5 | 2.5 |
| Floramat | 100.0 | 100.0 |
| Phenylethyl alcohol | 30.0 | 30.0 |
| Geranyl silicic acid ester | 105.0 | — |
| Geraniol | — | 105.0 |
| Cyclohexyl salicylate | 150.0 | 150.0 |
| Citronellol | 20.0 | 20.0 |

These perfume oils were incorporated in an acidic cleaner with a formulation according to Table 11. A bathroom (bathtub and wash basin) was then cleaned with the perfume-containing cleaner. The perfume impression of the cleaned surface was then evaluated for intensity and pleasure by 8 perfume experts (perfumists) on the following scale:

| Intensity | Appeal |
| --- | --- |
| 1 = no perfume | 1 = very poor |
| 2 = some perfume | 2 = poor |
| 3 = medium strong perfume | 3 = moderate |
| 4 = strong perfume | 4 = average |
| 5 = very strong perfume | 5 = good |
|  | 6 = very good |
|  | 7 = excellent |

TABLE 11

Formulation of the acidic cleaner [% by weight]

| | |
|---|---|
| ABS Acid | 4.0 |
| Fatty alcohol ethoxylate (EO = 7) | 2.0 |
| KOH | 5.5 |
| Citric acid × 1H$_2$O | 10.5 |
| Soda calc. | 0.05 |
| Glutaraldehyde | 1.5 |
| Perfume | 1.5 |
| Deionized water, sterilized | Balance |
| pH | 4.4 |

The results of the fragrance tests are set out in Table 12. Immediately afterwards and even after 3 hours, both perfume oils make comparable impressions. After only 6 hours and more so after 24 hours, a far more intensive perfume was noticeable in the case of cleaner 10A according to the invention and, in addition, also had a more pleasant effect on the perfume experts.

TABLE 12

Results of the fragrance tests after cleaning of bathtubs/wash basins

| | Perfume oil 10 A | | Perfume oil 10 B | |
|---|---|---|---|---|
| | Intensity | Appeal | Intensity | Appeal |
| Fresh | 4.5 | 4.6 | 4.7 | 4.5 |
| After 3 hours | 4.6 | 4.5 | 4.4 | 4.5 |
| After 6 hours | 4.4 | 4.6 | 3.8 | 4.3 |
| After 24 hours | 3.1 | 3.7 | 1.8 | 3.1 |

B2 Multipurpose Cleaner

Perfume oils with formulations according to Table 14 were incorporated in a multipurpose cleaner with a formulation according to Table 13 (two-phase cleaner). 14 A is the Example according to the invention, 14 B is the Comparison Example. A floor was cleaned with these cleaners after which the perfume impression was evaluated as in B1 by 8 perfume experts. The results in Table 15 again show comparable impressions immediately after cleaning and 3 hours afterwards, but a greater intensity and also a more pleasant impression after only 6 hours in the case of the Example according to the invention. The advantages of the cleaner according to the invention become particularly clear after 24 hours.

TABLE 13

Formulations of the multipurpose cleaner (two-phase cleaner); quantities in [% by weight]

| | |
|---|---|
| ABS Acid | 4 |
| Fatty alcohol ethoxylate (EO = 7) | 2 |
| KOH | 4.5 |
| Citric acid × 1H$_2$O | 4.75 |
| Cetiol OE | 4.5 |
| Soda calc. | 0.2 |
| Glutaraldehyde | 0.05 |
| Perfume | 1.6 |
| Deionized water, sterilized | Balance |
| pH | 10 |

TABLE 14

Perfume oils for a multipurpose cleaner with a lemon fragrance

| Ingredient | 14A Quantities in % | 14B Quantities in % |
|---|---|---|
| Dihydromyrcenol | 30.0 | 30.0 |
| Aldinyle 3881 | 5.0 | 5.0 |
| Citral AR | 15.0 | 15.0 |
| Geranonitrile | 56.0 | 56.0 |
| Tridecene-2-nitrile 10% in DPG | 3.0 | 3.0 |
| Methylpamplemousse | 5.0 | 5.0 |
| Vertacetal | 2.0 | 2.0 |
| Citronellal | 10.0 | 10.0 |
| Citrathal | 10.0 | 10.0 |
| Orange oil, distilled, white | 480.0 | 480.0 |
| Methylnaphthyl ketone crystallized | 5.0 | 5.0 |
| Aldehyde C08 | 10.0 | 10.0 |
| Aldehyde C09 | 6.0 | 6.0 |
| Aldehyde C10 | 15.0 | 15.0 |
| Cyclovertal | 7.0 | 7.0 |
| Hexenol (Beta Gamma) | 1.0 | 1.0 |
| Hexyl acetate | 6.0 | 6.0 |
| Camphor synthetic | 11.0 | 11.0 |
| Pine oil, French, 70 | 30.0 | 30.0 |
| Carvon L | 1.0 | 1.0 |
| Styrolyl acetate | 6.0 | 6.0 |
| Linaolool | 30.0 | 30.0 |
| Phenylethyl alcohol | 20.0 | 20.0 |
| Citronellol | 25.0 | 25.0 |
| Geranyl acetate | 3.0 | 3.0 |
| Geranyl silicic acid ester | 127.0 | — |
| Geraniol | — | 127.0 |
| Neryl acetate | 1.0 | 1.0 |
| Cyclohexyl salicylate | 70.0 | 70.0 |
| Sandelice | 5.0 | 5.0 |
| Boisambrene Forte | 3.0 | 3.0 |
| Ethyl vanillin 10% in DPG | 2.0 | 2.0 |

TABLE 15

Results of the fragrance tests after cleaning of floors

| | Perfume oil 14 A | | Perfume oil 14 B | |
|---|---|---|---|---|
| | Intensity | Appeal | Intensity | Appeal |
| Fresh | 4.2 | 4.3 | 4.3 | 4.3 |
| After 3 hours | 4.1 | 4.1 | 4.0 | 4.2 |
| After 6 hours | 3.6 | 4.0 | 3.2 | 3.6 |
| After 24 hours | 2.9 | 3.1 | 1.2 | 2.2 |

C Shower Bath

A shower bath is taken in the following as an example of a cosmetic skin care preparation. Table 16 shows the perfume oil composition which was used in the shower bath with a formulation according to Table 17. 16 A is the formulation according to the invention, 16 B the comparison formulation. The forearms of a volunteer were cleaned with the shower bath and the perfume was evaluated by 8 perfume experts using the same scale as in B1. As also observed with the cleaners, the perfume impression of the shower bath according to the invention lasts far longer and is also more pleasant on the senses, even after a prolonged period.

TABLE 16

Perfume oils with a fresh, flowery note

| Ingredient | 16A Quantities in % | 16B Quantities in % |
|---|---|---|
| Bergamot oil | 250.0 | 250.0 |
| Citrus oil Messina | 50.0 | 50.0 |
| Citronellal | 2.0 | 2.0 |
| Orange oil sweet | 50.0 | 50.0 |
| Lavender oil | 50.0 | 50.0 |
| Terpineol | 50.0 | 50.0 |
| Lilial | 100.0 | 100.0 |
| Phenylethyl alcohol | 80.0 | 80.0 |
| Citronellyl silicic acid ester | 100.0 | — |
| Citronellol | — | 100.0 |
| Geraniol | 20.0 | 20.0 |
| Benzyl acetate | 60.0 | 60.0 |
| Isoraldein 70 | 50.0 | 50.0 |
| Ylang | 30.0 | 30.0 |
| Ambroxan 10% in IPM | 1.0 | 1.0 |
| Heliotropin | 47.0 | 47.0 |
| Habanolide | 60.0 | 60.0 |

TABLE 17

Composition of the shower bath

| Ingredients | [% by weight] |
|---|---|
| $C_{12-14}$ fatty alcohol 2 EO sulfate | 8.0 |
| $C_{12-14}$ fatty alcohol sulfosuccinate | 4.0 |
| Cocoamide betaine | 2.0 |
| Coconut fatty acid monoglyceride 7 EO | 3.0 |
| Glycerol monolaurate | 2.0 |
| Protein hydrolyzate | 1.0 |
| Ethylene glycol distearate | 1.0 |
| Perfume oil | 1.0 |
| Water | Balance |

TABLE 18

Result of the fragrance tests after cleaning of the forearms with the shower bath

| | Perfume oil 16 A | | Perfume oil 16 B | |
|---|---|---|---|---|
| | Intensity | Appeal | Intensity | Appeal |
| Fresh | 4.2 | 5.1 | 4.4 | 5.2 |
| After 2 hours | 3.8 | 4.8 | 3.9 | 4.9 |
| After 5 hours | 3.5 | 4.5 | 3.3 | 4.2 |
| After 8 hours | 2.5 | 4.0 | 1.8 | 3.5 |

D Soap

A bar soap was produced with a composition according to Table 20. It contained the perfume composition 19A in the Example according to the invention and the perfume composition 19B in the Comparison Example (Table 19). After the forearms of a volunteer had been cleaned, fragrance was again evaluated by 8 perfume experts. The intensity of the fragrance impression and the appeal of the fragrance impression were again individually evaluated. The averaged judgements are shown in Table 21. In this case, too, the fragrance impressions immediately after washing and 2 hours thereafter were still comparable. However, the superiority of the Example according to the invention was again evident after 5 hours and very much so after 8 hours.

TABLE 19

Perfume oils with a fresh, flowery note

| Ingredient | 19 A Quantities in ‰ | 19 B Quantities in ‰ |
|---|---|---|
| Bergamot oil | 250.0 | 250.0 |
| Citrus oil Messina | 50.0 | 50.0 |
| Citronellal | 2.0 | 2.0 |
| Orange oil sweet | 50.0 | 50.0 |
| Lavender oil | 50.0 | 50.0 |
| Terpineol | 50.0 | 50.0 |
| Lilial | 100.0 | 100.0 |
| Phenylethyl alcohol | — | 80.0 |
| Phenylethyl silicic acid ester | 100.0 | — |
| Citronellol | 100.0 | 100.0 |
| Geraniol | 20.0 | 20.0 |
| Benzyl acetate | 60.0 | 60.0 |
| Isoraldein 70 | 50.0 | 50.0 |
| Ylang | 30.0 | 30.0 |
| Ambroxan 10% in IPM | 1.0 | 1.0 |
| Heliotropin | 47.0 | 47.0 |
| Habanolide | 60.0 | 60.0 |

TABLE 20

Composition of the bar soap [% by weight]

| Ingredient | [% by weight] |
|---|---|
| Tallow fatty acid soap | 60 |
| Coconut oil fatty acid soap | 27 |
| Glycerol | 2 |
| Perfume oil | 3 |
| Water | Balance |

TABLE 21

Result of the fragrance test after cleaning of the forearms with the soap from Table 20

| | Perfume oil 19 A | | Perfume oil 19 B | |
|---|---|---|---|---|
| | Intensity | Appeal | Intensity | Appeal |
| Fresh | 4.1 | 4.7 | 4.2 | 4.7 |
| After 2 hours | 3.6 | 4.3 | 3.5 | 4.1 |
| After 5 hours | 3.1 | 3.8 | 2.7 | 3.4 |
| After 8 hours | 2.4 | 3.2 | 1.6 | 2.6 |

E Deodorant

A perfume oil composition for a deodorant spray is shown in Table 22. 22 A is again the composition according to the invention, 22 B the comparison composition. To carry out the fragrance test, the deodorant is applied to a paper tissue which was stored in a beaker at 37° C. to simulate underarm conditions. The perfume impression was again evaluated for intensity and appeal by 8 perfume experts. The results are set out in Table 24. As in all preceding tests, it was found that the perfume oils according to the invention have distinct advantages in terms of perfume appeal and intensity of the remaining perfume impression.

TABLE 22

Perfume oils for a deodorant spray with a flowery note reminiscent of peonies

| Ingredient | 22 A Quantities in ‰ | 22 B Quantities in ‰ |
|---|---|---|
| Petit grain oil Paraguay | 5.0 | 5.0 |
| Cyclogalbanate | 1.0 | 1.0 |
| Hexenol (Beta Gamma) | 3.0 | 3.0 |
| Hexenyl acetate | 3.0 | 3.0 |
| Cyclovertal 10% in DPG | 5.0 | 5.0 |
| Phenylacetaldehyde dimethyl acetal | 5.0 | 5.0 |
| Calone 10% in DPG | 5.0 | 5.0 |
| Acetoacetic ester | 35.0 | 35.0 |
| Cuminaldehyde 10% in DPG | 5.0 | 5.0 |
| Styrolyl acetate | 5.0 | 5.0 |
| Bourgeonal | 6.0 | 6.0 |
| Cyclamen aldehyde extra L.G. | 4.0 | 4.0 |
| Floral 943160 | 62.0 | 62.0 |
| Hydroxycitronellal pure | 12.0 | 12.0 |
| Lilial | 37.0 | 37.0 |
| Lyral | 61.0 | 61.0 |
| Nerolidol | 4.0 | 4.0 |
| Ethyl linalool | 152.0 | 152.0 |
| Linalool | 14.0 | 14.0 |
| Rose oil Turkey | 2.0 | 2.0 |
| Rose Wardia | 10.0 | 10.0 |
| Phenylethyl alcohol | 28.0 | 28.0 |
| Citronellyl acetate | 40. | 40.0 |
| Citronellyl silicic acid ester | 106.0 | — |
| Citronellol | — | 106.0 |
| Geraniol | 10.0 | 10.0 |
| Phenylethyl acetate | 1.0 | 1.0 |
| Rose oxide R 10% in DPG | 5.0 | 5.0 |
| Geranium oil Bourbon | 20.0 | 20.0 |
| Benzyl acetate | 41.0 | 41.0 |
| Veloutone | 1.0 | 1.0 |
| Hedione | 100.0 | 100.0 |
| Hexyl cinnamaldehyde (Alpha) | 70.0 | 70.0 |
| Hydratropa aldehyde dim. acetal | 2.0 | 2.0 |
| Isoraldein | 9.0 | 9.0 |
| Cycloheyl salicylate | 75.0 | 75.0 |
| Hexenyl salicylate (CIS-3) | 21.0 | 21.0 |
| Ethyl vanillin 10% in DPG | 5.0 | 5.0 |
| Ethylphenyl acetate | 4.0 | 4.0 |
| Phenylethyl phenyl acetate | 1.0 | 1.0 |
| Ambrettolide | 3.0 | 3.0 |
| Cyclopentadecanolide | 2.0 | 2.0 |
| Ethylene brassylate | 15.0 | 15.0 |
| Indoflor | 5.0 | 5.0 |

TABLE 23

Formulation of the deodorant [% by weight]

| | |
|---|---|
| APG 600 | 0.050% by weight |
| APG 220 | 0.150% by weight |
| Cetiol OE | 0.030% by weight |
| Eutanol G | 0.007% by weight |
| Citric acid (cryst.) | 0.005% by weight |
| Perfume oil | 0.300% by weight |
| Aluminium hydroxychloride | 20.000% by weight |
| Boehmite (20%) | 4.000% by weight |
| Water | 75.460% by weight |

APG 600
Plantacare 1200 UP (Cognis GmbH)
Active substance: 50–53% by weight alkyl-$C_{12-16}$-oligo(1, 4)-glucoside APG 220
Plantacare 220 UP (Cognis GmbH)
Active substance: 62–65% by weight alkyl-$C_{8-10}$-oligo-(1, 5)-glucoside Cetiol OE
Dioctyl ether (Cognis GmbH)

Eutanol G
2-octyldodecanol (Cognis GmbH)

TABLE 24

Results of the fragrance test after spraying onto paper tissue stored in a beaker at 37° C.

| | Perfume oil 22 A | | Perfume oil 22 B | |
|---|---|---|---|---|
| | Intensity | Appeal | Intensity | Appeal |
| Fresh | 4.8 | 5.1 | 4.9 | 5.3 |
| After 2 hours | 4.3 | 5.0 | 4.3 | 4.9 |
| After 5 hours | 3.2 | 4.5 | 2.9 | 4.2 |
| After 8 hours | 2.8 | 4.1 | 1.8 | 3.1 |

F Hair Spray

Composition 25 A is a perfume oil according to the invention for a hair spray. 25 B is a comparison composition (Table 25). These perfume compositions were incorporated in a hair spray with the formulation shown in Table 26 and the perfume impression of hair tresses sprayed with the spray was evaluated by 8 perfume experts. The results are set out in Table 27. It was again found that the perfume intensity of the compositions according to the invention remains far greater than that of known compositions for longer periods.

TABLE 25

Perfume oils for a hair spray with a flowery, fresh, spicy note

| Ingredient | 25 A Quantities in ‰ | 25 B Quantities in ‰ |
|---|---|---|
| Linalyl acetate | 28.0 | 28.0 |
| Citrus oil Messina | 44.0 | 44.0 |
| Methylpamplemousse | 0.5 | 0.5 |
| Cyclocalbanate | 0.5 | 0.5 |
| Cyclovertal | 1.0 | 1.0 |
| Hexenol (Beta Gamma) | 2.0 | 2.0 |
| Hexenyl acetate | 1.0 | 1.0 |
| Precyclemone B | 5.0 | 5.0 |
| Peranat | 5.0 | 5.0 |
| Terpineol | 3.0 | 3.0 |
| Styrolyl acetate | 2.0 | 2.0 |
| Lilial | 50.0 | 50.0 |
| Troenan | 27.0 | 27.0 |
| Ethyl linalool | 106.0 | 106.0 |
| Linalool | 36.0 | 36.0 |
| Helional | 40.0 | 40.0 |
| Phenylethyl alcohol | 10.0 | 10.0 |
| Citronellyl acetate | 5.0 | 5.0 |
| Citronellol | 35.0 | 35.0 |
| Geranyl silicic acid ester | 100.0 | — |
| Geraniol | — | 100.0 |
| Geranium oil Bourbon | 10.0 | 10.0 |
| Jasmone-cis | 2.0 | 2.0 |
| Hedione | 157.0 | 157.0 |
| Hexyl cinnamaldehyde (Alpha) | 41.0 | 41.0 |
| Isoraldein 70 | 16.0 | 16.0 |
| Ionone beta synthetic | 14.0 | 14.0 |
| Liffarome | 1.0 | 1.0 |
| Cyclohexyl salicylate | 6.0 | 6.0 |
| Patchouli oil | 3.0 | 3.0 |
| Sandelice | 26.0 | 26.0 |
| Iso E Super | 109.0 | 109.0 |
| Ambroxan | 1.0 | 1.0 |
| Vanillin | 2.0 | 2.0 |
| Ethylene brassylate | 110.5 | 110.5 |
| Indole | 0.5 | 0.5 |

TABLE 26

| Formulation of the hair spray [% by weight] | |
|---|---|
| Alberdingk U ® 500 | 5.0 |
| Luviskol ® VA 64 | 3.0 |
| Panthenol | 0.5 |
| Perfume oil | 1.0 |
| Dimethyl ether | 40.0 |
| Water | to 100 |

Alberdingk U 500
Anionic polyether polyurethane dispersion (40% in water) (ALBERDINGK BOLEY)

Luviskol VA 64
Vinyl acetate/vinyl pyrrolidone copolymer (BASF)

TABLE 27

Result of the fragrance test after spraying of hair tresses with the hair spray from Table 25

| | Perfume oil 25 A | | Perfume oil 25 B | |
|---|---|---|---|---|
| | Intensity | Appeal | Intensity | Appeal |
| Fresh | 4.8 | 4.8 | 4.9 | 4.7 |
| After 2 hours | 4.0 | 4.4 | 3.9 | 4.4 |
| After 5 hours | 3.2 | 3.8 | 2.9 | 3.6 |
| After 8 hours | 2.4 | 3.2 | 1.8 | 2.8 |

The invention claimed is:

1. A composition comprising a mixture of silicic acid esters corresponding to the following formulae:

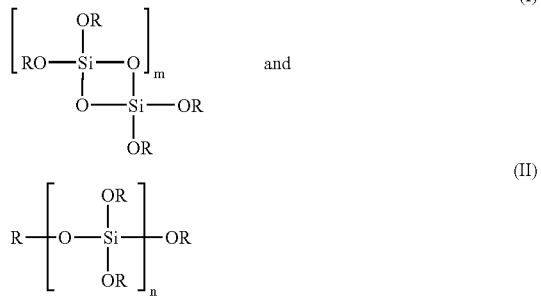

in which all R independently of one another are selected from the group consisting of H, linear or branched, saturated or unsaturated, substituted or unsubstituted $C_{1-6}$ hydrocarbon radicals, perfume alcohol radicals, and biocide alcohol radicals, m assumes a value of 1 to 20, and n assumes a value of 2 to 100, provided that at least one R is a perfume alcohol radical or a biocide alcohol radical.

2. The composition of claim 1, wherein at least some of the substituents R in formulae I and II are selected from the group consisting of methyl, ethyl, n-propyl, isopropyl, n-butyl, isobutyl, and tert-butyl.

3. The composition of claim 2, wherein at least 10 mol-% of the substituents R in formulae I and II are selected from the group consisting of 10-undecen-1-ol, 2,6-dimethylheptan-2-ol, 2-methylbutanol, 2-methylpentanol, 2-phenoxyethanol, 2-phenylpropanol, 2-tert-butyl cyclohexanol, 3,5,5-trimethylcyclohexanol, 3-hexanol, 3-methyl-5-phenyl pentanol, 3-octanol, 3-phenylpropanol, 4-heptenol, 4-isopropyl cyclohexanol, 4-tert-butyl cyclohexanol, 6,8-dimethyl-2-nonanol, 6-nonen-1-ol, 9-decen-1-ol, α-methyl benzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethyl benzyl carbinol, dimethyl heptanol, dimethyl octanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-methan-7-ol, phenyl ethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol.

4. The composition of claim 1, wherein at least 5 mol-% of the substituents R in formulae I and II are selected from the group consisting of methyl, ethyl, n-propyl, isopropyl, n-butyl, isobutyl, and tert-butyl.

5. The composition of claim 1, wherein at least 10 mol-% of the substituents R in formulae I and II are selected from the group consisting of 10-undecen-1-ol, 2,6-dimethylheptan-2-ol, 2-methylbutanol, 2-methylpentanol, 2-phenoxyethanol, 2-phenylpropanol, 2-tert-butyl cyclohexanol, 3,5,5-trimethylcyclohexanol, 3-hexanol, 3-methyl-5-phenyl pentanol, 3-octanol, 3-phenylpropanol, 4-heptenol, 4-isopropyl cyclohexanol, 4-tert-butyl cyclohexanol, 6,8-dimethyl-2-nonanol, 6-nonen-1-ol, 9-decen-1-ol, α-methyl benzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethyl benzyl carbinol, dimethyl heptanol, dimethyl octanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-methan-7-ol, phenyl ethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol.

6. The composition of claim 5, wherein at least 20 mol-% of the substituents R in formulae I and II are selected from the group consisting of 10-undecen-1-ol, 2,6-dimethylheptan-2-ol, 2-methylbutanol, 2-methylpentanol, 2-phenoxyethanol, 2-phenylpropanol, 2-tert-butyl cyclohexanol, 3,5,5-trimethylcyclohexanol, 3-hexanol, 3-methyl-5-phenyl pentanol, 3-octanol, 3-phenylpropanol, 4-heptenol, 4-isopropyl cyclohexanol, 4-tert-butyl cyclohexanol, 6,8-dimethyl-2-nonanol, 6-nonen-1-ol, 9-decen-1-ol, α-methyl benzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethyl benzyl carbinol, dimethyl heptanol, dimethyl octanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-methan-7-ol, phenyl ethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol.

7. The composition of claim 6, wherein at least 40 mol-% of the substituents R in formulae I and II are selected from the group consisting of 10-undecen-1-ol, 2,6-dimethylheptan-2-ol, 2-methylbutanol, 2-methylpentanol, 2-phenoxyethanol, 2-phenylpropanol, 2-tert-butyl cyclohexanol, 3,5,5-trimethylcyclohexanol, 3-hexanol, 3-methyl-5-phenyl pentanol, 3-octanol, 3-phenylpropanol, 4-heptenol, 4-isopropyl cyclohexanol, 4-tert-butyl cyclohexanol, 6,8-dimethyl-2-nonanol, 6-nonen-1-ol, 9-decen-1-ol, α-methyl benzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethyl benzyl carbinol, dimethyl heptanol, dimethyl octanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-methan-7-ol, phenyl ethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol.

8. The composition of claim 7, wherein at least 20 mol-% of the substituents R in formulae I and II are selected from the group consisting of 10-undecen-1-ol, 2,6-dimethylheptan-2-ol, 2-methylbutanol, 2-methylpentanol, 2-phenoxyethanol, 2-phenylpropanol, 2-tert-butyl cyclohexanol, 3,5,5-trimethylcyclohexanol, 3-hexanol, 3-methyl-5-phenyl pentanol, 3-octanol, 3-phenylpropanol, 4-heptenol, 4-isopropyl cyclohexanol, 4-tert-butyl cyclohexanol, 6,8-dimethyl-2-nonanol, 6-nonen-1-ol, 9-decen-1-ol, α-methyl benzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethyl benzyl carbinol, dimethyl heptanol, dimethyl octanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-methan-7-ol, phenyl ethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol.

9. The composition of claim 8, wherein at least 40 mol-% of the substituents R in formulae I and II are selected from the group consisting of 10-undecen-1-ol, 2,6-dimethylheptan-2-ol, 2-methylbutanol, 2-methylpentanol, 2-phenoxyethanol, 2-phenylpropanol, 2-tert-butyl cyclohexanol, 3,5,5-trimethylcyclohexanol, 3-hexanol, 3-methyl-5-phenyl pentanol, 3-octanol, 3-phenylpropanol, 4-heptenol, 4-isopropyl cyclohexanol, 4-tert-butyl cyclohexanol, 6,8-dimethyl-2-nonanol, 6-nonen-1-ol, 9-decen-1-ol, α-methyl benzyl alcohol, α-terpineol, amyl salicylate, benzyl alcohol, benzyl salicylate, β-terpineol, butyl salicylate, citronellol, cyclohexyl salicylate, decanol, dihydromyrcenol, dimethyl benzyl carbinol, dimethyl heptanol, dimethyl octanol, ethyl salicylate, ethyl vanillin, eugenol, farnesol, geraniol, heptanol, hexyl salicylate, isoborneol, isoeugenol, isopulegol, linalool, menthol, myrtenol, n-hexanol, nerol, nonanol, octanol, p-methan-7-ol, phenyl ethyl alcohol, phenol, phenyl salicylate, tetrahydrogeraniol, tetrahydrolinalool, thymol, trans-2-cis-6-nonadienol, trans-2-nonen-1-ol, trans-2-octenol, undecanol, vanillin, and cinnamyl alcohol.

10. The composition of claim 1, wherein m assumes a value of 2 to 10 and n assumes a value of 2 to 50.

11. The composition of claim 10, wherein m assumes a value of 2 to 3 and n assumes a value of 3 to 10.

12. The composition of claim 11, wherein n assumes a value of 4, 5, 6, 7 or 8.

13. The composition of claim 1, wherein the silicic acid ester corresponding to formula I comprises mixtures of silicic acid esters corresponding to at least one of the following formulae:

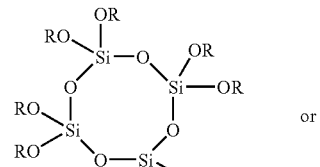

or

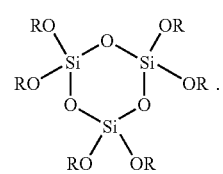

14. A liquid or solid detergent or cleaning composition comprising a surfactant and the composition of claim 1 as a fragrance or perfume.

15. The composition of claim 14, comprising 0.001% to 10% by weight of the silicic acid ester mixture.

16. The composition of claim 15, comprising 0.01% to 5% by weight of the silicic acid ester mixture.

17. The composition of claim 16, comprising 0.02% to 3% by weight of the silicic acid ester mixture.

18. The composition of claim 17, comprising 0.05% to 2% by weight of the silicic acid ester mixture.

19. The composition of claim 14, comprising an additional fragrance or perfume.

20. The composition of claim 14, comprising a liquid or gel-form laundry detergent, dishwashing detergent, or cleaner for flush toilets.

21. The composition of claim 14, comprising a liquid or gel-form cleaner for hard surfaces, glass, floors, or bathrooms.

22. The composition of claim 14, in the form of a liquid cleaner having more than one phase.

23. The composition of claim 14, having a powder or granular form.

24. The composition of claim 14, in the form of a shaped body.

25. The composition of claim 24, wherein the shaped body has the form of a tablet.

26. The composition of claim 24, wherein the shaped body has more than one phase.

27. A cosmetic skin or hair care composition comprising cosmetically acceptable carrier and the composition of claim 1 as a fragrance or perfume.

28. The composition of claim 27, comprising 0.001% to 10% by weight of the silicic acid ester mixture.

29. The composition of claim 28, comprising 0.01% to 5% by weight of the silicic acid ester mixture.

30. The composition of claim 29, comprising 0.02% to 3% by weight of the silicic acid ester mixture.

31. The composition of claim 30, comprising 0.05% to 2% by weight of the silicic acid ester mixture.

32. The composition of claim 27, comprising an additional fragrance or perfume.

33. A cosmetic hair or skin care preparation comprising silicic acid ester mixtures comprising silicic acid esters corresponding to the following formulae:

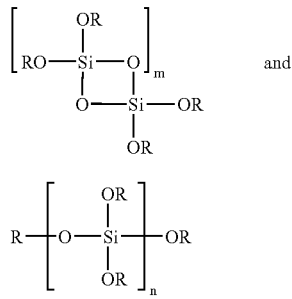

(I)

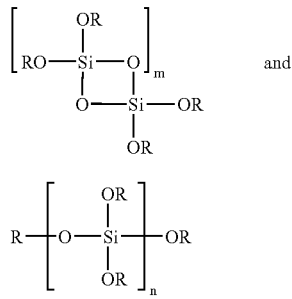

(II)

in which all R independently of one another are selected from the group consisting of H, linear or branched, saturated or unsaturated, substituted or unsubstituted $C_{1-6}$ hydrocarbon radicals, perfume alcohol radicals, and biocide alcohol radicals, m assumes a value of 1 to 20, and n assumes a value of 2 to 100, provided that at least one R is a perfume alcohol radical or a biocide alcohol radical.

34. The cosmetic preparation of claim 33, comprising 0.001% to 10% by weight of the silicic acid ester mixtures corresponding to formulae I and II.

35. The cosmetic preparation of claim 34, comprising 0.01% to 5% by weight of the silicic acid ester mixtures corresponding to formulae I and II.

36. The cosmetic preparation of claim 35, comprising 0.02% to 3% by weight of the silicic acid ester mixtures corresponding to formulae I and II.

37. The cosmetic preparation of claim 36, comprising 0.05% to 2% by weight of the silicic acid ester mixtures corresponding to formulae I and II.

38. The cosmetic preparation of claim 33, comprising water and a surfactant, and being suitable for the treatment of keratin fibers or for the treatment of skin.

39. The cosmetic preparation of claim 33, in the form of a shaped body that comprises surface-active ingredients.

40. The cosmetic preparation of claim 33, in the form of a deodorizing preparation.

41. The cosmetic preparation of claim 33, in the form of a hair setting preparation comprising one or more polymers.

42. The cosmetic preparation of claim 41, wherein the one or more polymers comprise at least one polyurethane.

43. A method of prolonging the perfume effect of a perfume in a cleaning or cosmetic composition comprising a perfume, comprising adding to the composition an effective amount of a silicic acid ester mixture comprising silicic acid esters corresponding to the following formulae:

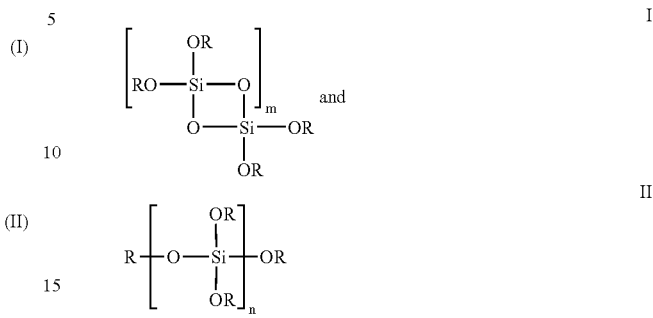

in which all R independently of one another are selected from the group consisting of H, linear or branched, saturated or unsaturated, substituted or unsubstituted $C_{1-6}$ hydrocarbon radicals, perfume alcohol radicals, and biocide alcohol radicals, m assumes a value of 1 to 20, and n assumes a value of 2 to 100, provided that at least one R is a perfume alcohol radical or a biocide alcohol radical.

44. A method of imparting biocidal properties to a cleaning or detergent composition or a cosmetic hair or skin care preparation, comprising adding to the composition or preparation an effective amount of a silicic acid ester mixture comprising silicic acid esters corresponding to the following formulae:

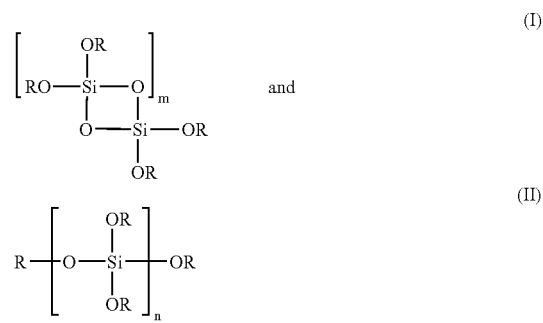

in which all R independently of one another are selected from the group consisting of H, linear or branched, saturated or unsaturated, substituted or unsubstituted $C_{1-6}$ hydrocarbon radicals, perfume alcohol radicals, and biocide alcohol radicals, m assumes a value of 1 to 20, and n assumes a value of 2 to 100, provided that at least one R is a perfume alcohol radical or a biocide alcohol radical.

* * * * *

UNITED STATES PATENT AND TRADEMARK OFFICE
CERTIFICATE OF CORRECTION

PATENT NO. : 7,098,178 B2 Page 1 of 1
APPLICATION NO. : 10/221890
DATED : August 29, 2006
INVENTOR(S) : Thomas Gerke et al.

It is certified that error appears in the above-identified patent and that said Letters Patent is hereby corrected as shown below:

Title Page,
Item (75) Inventors:
After "Neuss", delete "(GB)" and insert -- (DE) --.
After "Krefeld", delete "(GB)" and insert -- (DE) --.
After "Willich", delete "(GB)" and insert -- (DE) --.

Signed and Sealed this

Twenty-third Day of October, 2007

JON W. DUDAS
*Director of the United States Patent and Trademark Office*